(12) United States Patent
Durocher et al.

(10) Patent No.: US 11,261,466 B2
(45) Date of Patent: Mar. 1, 2022

(54) HOMOLOGOUS RECOMBINATION FACTORS

(71) Applicant: Sinai Health System, Toronto (CA)

(72) Inventors: Daniel Durocher, Toronto (CA); Alexandre Orthwein, Toronto (CA); Sylvie Noordermeer, Toronto (CA)

(73) Assignee: Sinai Health System, Toronto (CA)

( * ) Notice: Subject to any disclaimer, the term of this patent is extended or adjusted under 35 U.S.C. 154(b) by 0 days.

(21) Appl. No.: 15/554,042

(22) PCT Filed: Mar. 1, 2016

(86) PCT No.: PCT/CA2016/000057
§ 371 (c)(1),
(2) Date: Aug. 28, 2017

(87) PCT Pub. No.: WO2016/138574
PCT Pub. Date: Sep. 9, 2016

(65) Prior Publication Data
US 2018/0073039 A1    Mar. 15, 2018

Related U.S. Application Data

(60) Provisional application No. 62/127,013, filed on Mar. 2, 2015, provisional application No. 62/222,542, filed on Sep. 23, 2015.

(51) Int. Cl.
| | | |
|---|---|---|
| *C12N 15/00* | (2006.01) | |
| *C12N 15/09* | (2006.01) | |
| *C12N 15/113* | (2010.01) | |
| *C07K 14/47* | (2006.01) | |
| *C12N 15/90* | (2006.01) | |
| *A61K 31/713* | (2006.01) | |
| *C12N 15/10* | (2006.01) | |
| *C12Q 1/6886* | (2018.01) | |
| *C12N 15/63* | (2006.01) | |
| *C12N 9/00* | (2006.01) | |
| *C12N 15/67* | (2006.01) | |

(52) U.S. Cl.
CPC .......... *C12N 15/902* (2013.01); *A61K 31/713* (2013.01); *C07K 14/47* (2013.01); *C12N 9/00* (2013.01); *C12N 15/00* (2013.01); *C12N 15/09* (2013.01); *C12N 15/102* (2013.01); *C12N 15/113* (2013.01); *C12N 15/1138* (2013.01); *C12N 15/63* (2013.01); *C12N 15/67* (2013.01); *C12Q 1/6886* (2013.01); *C12N 15/90* (2013.01); *C12N 2310/14* (2013.01); *C12N 2310/141* (2013.01); *C12N 2310/20* (2017.05); *C12N 2310/531* (2013.01); *C12N 2501/065* (2013.01); *C12N 2800/80* (2013.01); *C12Q 2600/158* (2013.01); *C12Q 2600/178* (2013.01)

(58) Field of Classification Search
CPC ........ C07K 14/47; C12N 15/00; C12N 15/09; C12N 15/113; C12N 15/902; C12N 2310/11; C12N 2310/14; C12N 2310/141; C12N 2501/065
See application file for complete search history.

(56) References Cited

FOREIGN PATENT DOCUMENTS

| | | |
|---|---|---|
| WO | WO 2014/172458 | 10/2014 |
| WO | WO 2014/204725 | 12/2014 |
| WO | WO-2014/204725 A1 | 12/2014 |

OTHER PUBLICATIONS

Zhang et al, Current Biology 19:524-529, 2009.*
GenBank XP016881405, 2019.*
GenBank XP005258383, 2019.*
GenBank XP024307001, 2019.*
GenBank N976037.1, 2019.*
GenBank XP005258382, 2019.*
GenBank AAH30590.1, 2005.*
Kim et al, PNAS: e2949-e2955, 2012.*
Ma et al, ASM Molecular and Cellular Biology, DOI: 10.1128/MCB.06271-11, pp. 1506-1517, 2012.*
Thu, J. Thorac. Oncol. 6: 1521-1529, 2011.*
Volcic et al, Nucleic Acids Res. 40(1): 181-195, 2011.*
Escribano-Diaz et al, Molecular Cell 49(5): 872-883, available online Jan. 17, 2013.*
Mao et al, Cell Cycle 7(18): 2902-2906, 2008.*
Kim et al, Cellular Signaling 22: 1645-1654, 2010.*
Buisson et al, Nucleic Acids Res. 40(20): 10312-10323, 2012.*
Gandhi et al, Cell Cycle 12(4): 547-552, 2013.*
Choi et al, eLIFE 3:e02445, Apr. 30, 2014.*
Pauty et al, Biochem. J. 460: 331-342, 2014; available online Jun. 15, 2014.*
Tacconi et al, Chromosoma 124: 119-130, 2015; available online Nov. 29, 2014.*
Huertas et al, J. Biol. Chem. 284(14): 9558-9565, 2009.*
GenBank AC14371; *Homo sapiens* CTIP, 1998.*
Gonzalez-Rodriguez et al, Disease Models & Mechanisms 7(9): 1093-1100, available Sep. 1, 2014.*
Yaneva et al, Nucleic Acids Res. 33(16): 5320-5330, 2005.*
Kachhap et al (PLoS One 5(6): e11208, 12 pages, 2010).*
Sweetlove, Nature News doi:10.1038/news.2011.498; Aug. 2011.*

(Continued)

*Primary Examiner* — Kevin K Hill
(74) *Attorney, Agent, or Firm* — Howson & Howson LLP; Colleen M. Schaller

(57) ABSTRACT

The invention relates to factors that influence or regulate homologous recombination, methods to monitor these factors, the use of these factors to screen for agents that modulate homologous recombination, and methods to activate or modulate homologous recombination.

10 Claims, 27 Drawing Sheets
Specification includes a Sequence Listing.

(56) References Cited

OTHER PUBLICATIONS

Number of Mammalian species, en.wikipedia.org/wiki/Mammal, last visited Jul. 19, 2021.*
Number of organs, https://byjus.com/biology/what-are-the-78-organs-in-the-human-body/; last visited Jul. 19, 2021.*
Number of Cell Types, https://www.kenhub.com/en/library/anatomy/types-of-cells-in-the-human-body; last visited Jul. 19, 2021.*
Hsiao et al, J. Molecular Cell Biology 5: 157-165, 2013.*
Fukuda et al, Cancer Science 106(8): 1050-1056, Aug. 2015.*
Roy et al, BRCA1 and BRCA2: different roles in a common pathway of genome protection, Nat Rev Cancer, Dec. 23, 2011;12(1):68-78.
Ma et al, PALB2 interacts with KEAP1 to promote NRF2 nuclear accumulation and function, Mol Cell Biol. Apr. 2012;32(8):1506-17, Epub Feb. 13, 2012.
Jin et al, A family of diverse Cul4-Ddb1-interacting proteins includes Cdt2, which is required for S phase destruction of the replication factor Cdt1. Mol Cell. Sep. 1, 2006;23(5):709-21.
Canny et al, Inhibition of 53BP1 favors homology-dependent DNA repair and increases CRISPR-Cas9 genome-editing efficiency, Nat Biotechnol. Jan. 2018;36(1):95-102, doi: 10.1038/nbt.4021. Epub Nov. 27, 2017.
Zhang et al, PALB2 links BRCA1 and BRCA2 in the DNA-damage response, Curr Biol, Mar. 24, 2009; 19(6):524-9, doi: 10.1016/j.cub.2009.02.018. Epub Mar. 5, 2009.
Sy et al, PALB2 is an integral component of the BRCA complex required for homologous recombination repair, Proc Natl Acad Sci U S A. Apr. 28, 2009;106(17):7155-60, doi: 10.1073/pnas.0811159106, Epub Apr. 15, 2009.
Escribano-Diaz et al, A cell cycle-dependent regulatory circuit composed of 53BP1-RIF1 and BRCA1-CtIP controls DNA repair pathway choice, Mol Cell. Mar. 7, 2013;49(5):872-83, doi: 10.1016/j.molcel.2013.01.001. Epub Jan. 17, 2013.
Wiltshire et al, Sensitivity to poly(ADP-ribose) polymerase (PARP) inhibition identifies ubiquitin-specific peptidase 11 (USP11) as a regulator of DNA double-strand break repair. J Biol Chem. May 7, 2010;285(19):14565-71. doi: 10.1074/jbc.M110.104745, Epub Mar. 15, 2010.
Konstantin et al, Synthetic lethality of PARP inhibition in cancers lacking BRCA1 and BRCA2 mutations. Cell Cycle. Apr. 15, 2011;10(8):1192-9, Epub Apr. 15, 2011.
Orthwein et al, A mechanism for the suppression of homologous recombination in G1 cells. Nature. Dec. 17, 2015;528(7582):422-6. doi: 10.1038/nature16142. Epub Dec. 9, 2015.
Extended European Search Report dated Jul. 3, 2018 issued in corresponding European Patent application No. 16758390.5.
Bhattacharyya et al., "The Breast Cancer Susceptibility Gene BRCA1 Is Required for Subnuclear Assembly of Rad51 and Survival following Treatment with the DNA Cross-linking Agent Cisplatin", The Journal of Biological Chemistry, vol. 275(31):23899-23903, Aug. 2000.
Bunting et al., "53BP1 inhibits homologous recombination in Brca1-deficient cells by blocking resection of DNA breaks", Cell, vol. 141(2):243-254, Apr. 2010.
Chapman et al., "RIF1 Is Essential for 53BP1-Dependent Nonhomologous End Joining and Suppression of DNA Double-Strand Break Resection, Molecular Cell, vol. 49:858-871, Mar. 2013.
Cui et al., "Glutamine Deamidation and Dysfunction of Ubiquitin/NEDD8 by a Bacterial Effector Family", Science, vol. 329(5996):1215-1218, Sep. 2010.
Enchev et al., "Protein Neddylation: Beyond Cullin-RING Ligases", Nat Rev Mol Cell Biol., vol. 16(1):30-44, Jan. 2015.
Enchev et al., "Structural Insights into the COP9 Signalosome and Its Common Architecture with the 26S Proteasome Lid and eIF3", Structure, vol. 18:518-527, Apr. 2010.
Escribano-Diaz et al., "A Cell Cycle-Dependent Regulatory Circuit Composed of 53BP1-RIF1 and BRCA1-CtIP Controls DNA Repair Pathway Choice", Molecular Cell, vol. 49:872-883, Mar. 2013.

Feng et al., "RIF1 Counteracts BRCA1-mediated End Resection during DNA Repair", Journal of Biological Chemistry, vol. 288(16):11135-11143, Apr. 2013.
Fradet-Turcotte et al., "53BP1 is a reader of the DNA damage-induced H2A Lys15 ubiquitin mark", Nature, vol. 499(7456):50-54, Jul. 2013.
Genschik et al., "The emerging family of CULLIN3-RING ubiquitin ligases (CRL3s): cellular functions and disease implications", The EMBO Journal, vol. 32(17):2307-2320, Aug. 2013.
Guntas et al., "Engineering a genetically encoded competitive inhibitor of the KEAP1-NRF2 interaction via structure-based design and phage display", Protein Engineering, Design & Selection, vol. 29(1):1-9, Oct. 2015 (advance publication).
Hartlerode et al., "Cell Cycle-Dependent Induction of Homologous Recombination by a Tightly Regulated I-Scel Fusion Protein", PLoS One, vol. 6(3):e16501, Mar. 2011.
Hendriks et al., "Ubiquitin-specific Protease 11 (USP11) Deubiquitinates Hybrid Small Ubiquitin-like Modifier (SUMO)-Ubiquitin Chans to Counteract RING Finger Protein 4 (RNF4)", The Journal of Biological Chemistry, vol. 290(25):15526-15537, Jun. 2015.
Huertas et al., "Human CtIP Mediates Cell Cycle Control of DNA End Resection and Double Strand Break Repair", vol. 284(14):9558-9565, Apr. 2009.
Jackson et al., "CRL4s: the CUL4-RING E3 ubiquitin ligases", Trends Biochem Sci., vol. 34(11):562-570, Nov. 2009.
Jasin et al., "Repair of Strang Breaks by Homologous Recombination", Cold Spring Harbor Perspectives in Biology, vol. 5(11):a012740, Nov. 2013.
Juang et al., "OTUB1 co-opts Lys48-linked ubiquitin recognition to suppress E2 enzyme function", Mol Cell, vol. 45(3):384-397, Feb. 2012.
Kasparek et al., "DNA double-strand break repair pathways, chromosomal rearrangements and cancer", Seminars in Cell & Developmental Biology, vol. 22:886-897, Oct. 2011.
Li et al., "Links between genome integrity and BRCA1 tumor suppression", vol. 37(10):418-424, Oct. 2012.
Long et al., "Generation of nonhydrolyzable ubiquitin-histone mimics", Methods, vol. 10(0):143-138, Dec. 2014.
Ma et al., "PALB2 Interacts with KEAP1 to Promote NRF2 Nuclear Accumulation and Function", Molecular and Cellular Biology, vol. 32(8):1506-1517, Feb. 2012.
Moynahan et al., "Brca1 Controls Homology-Directed DNA Repair", Molecular Cell, vol. 4:511-518, Oct. 1999.
Panier et al., "Tandem Protein Interaction Modules Organize the Ubiquitin-Dependent Response to DNA Double-Strand Breaks", Molecular Cell, vol. 47:383-395, Aug. 2012.
Park et al, "PALB2: The Hub of a Network of Tumor Suppressors Involved in DNA Damage Responses", Biochim Biophys Acta, vol. 1846(1):263-275, Aug. 2014.
Pinder et al., "Nuclear domain 'knock-in' screen for the evaluation and identification of small molecule enhancers of CRISPR-based genome editing", Nucleic Acids Research, vol. 43(19):9379-9392, Oct. 2015.
Ran et al., "Genome engineering using the CRISPR-Cas9 system", Nat Protoc, vol. 8(11):2281-2308, Nov. 2013.
Rothkamm et al., "Pathways of DNA Double-Strand Break Repair during the Mammalian Cell Cycle", Molecular and Cellular Biology, vol. 23(16):5706-5715, Aug. 2003.
Roy et al., "BRCA1 and BRCA2: different roles in a common pathway of genome protection", Nature Reviews—Cancer, vol. 12:68-78, Jan. 2012.
Schlegel et al., "BRCA1 Promotes Induction of ssDNA by Ionizing Radiation", Cancer Res, vol. 66(10), May 2006.
Schoenfeld et al., "BRCA2 is Ubiquitinated In Vivo and Interacts with USP11, a Deubiquitinating Enzyme That Exhibits Prosurvival Function in the Cellular Response to DNA Damage", Molecular and Cellular Biology, vol. 24:7444-7455, Sep. 2004.
Simhadri et al., "Male Fertility Defect Associated with Disrupted BRCA1-PALB2 Interaction in Mice", The Journal of Biological Chemistry, vol. 289(35):24617-24629, Aug. 2014.
Sowa et al., "Defining the Human Deubiquitinating Enzyme Interaction Landscape", Cell, vol. 138(2):389-403, Jul. 2009.

(56) References Cited

OTHER PUBLICATIONS

Stark et al., "Genetic Steps of Mammalian Homologous Repair with Distinct Mutagenic Consequences", Molecular and Cellular Biology, vol. 24(21):9305-9316, Nov. 2004.

Sy et al., "PALB2 is an integral component of the BRCA complex required for homologous recombination repair", PNAS, vol. 106(17):7155-7160, Apr. 2009.

Taguchi et al., "Molecular mechanisms of the Keap1-Nrf2 pathway in stress response and cancer evolution", Genes to Cells, vol. 16(2):123-140, Feb. 2011.

Tang et al., "Acetylation Limits 53BP1 Association with Damaged Chromatin to Promote Homologous Recombination", Nat Struct Mol Biol., vol. 20(3):317-325, Mar. 2013.

Wiltshire et al., "Sensitivity to Poly(ADP-ribose) Polymerase (PARP) Inhibition Identified Ubiquitin-specific Peptidase 11 (USP11) as a Regulator of DNA Double-strand Break Repair", The Journal of Biological Chemistry, vol. 285(19):14565-14571, May 2010.

Xia et al., "Control of BRCA2 Cellular and Clinical Functions by a Nuclear Partner, PALB2", Molecular Cell, vol. 22:719-729, Jun. 2006.

Yamane et al., "RPA accumulation during class switch recombination represents 5'-3' DNA end resection during the S-G2/M phase of the cell cycle", Cell Rep., vol. 3(1):138-147, Jan. 2013.

Yin et al., "Nonhydrolyzable Diubiquitin Analogues Are Inhibitors of Ubiquitin Conjugation and Deconjugation", Biochemistry, vol. 39(32):10001-10010, Aug. 2000.

Zhang et al., "PALB2 Links BRCA1 and BRCA2 in the DNA-Damage Response", Curr Biol., vol. 19(6):524-529, Mar. 2009.

Zhang et al., "MDC1 and RNF8 function in a pathway that directs BRCA1-dependent localization of PALB2 required for homologous recombination", Journal of Cell Science, vol. 125(24):6049-6057, Sep. 2012.

Zimmerman et al., "53BP1 regulates DSB repair using Rif1 to control 5' end resection", Science, vol. 339(6120):700-704, Feb. 2013.

Orthwein, A. et al., "Mitosis inhibits DNA double-strand break repair to guard against telomere fusions", Science, vol. 344:189-193, 2014.

Escribano-Diaz et al., "A Cell Cycle Dependent Regulatory Circuit Composed of 53BP1-RF1 and BRCA1-CtIP Controls DNA Repair Pathway Choice", Molecular Cell, vol. 49:872-883, Mar. 2013.

Wiltshire et al., "Sensitivity to Poly(ADP-ribose) Polymerase (PARP) Inhibition Identifies Ubiquitin-specific Peptidase 11 (USP11) as a Regulator of DNA Double-strand Break Repair", Journal of Biological Chemistry, vol. 285(19):14565-14571, May 2010.

Konstantin et al., "Synthetic lethality of PARP inhibition in cancers lacking BRCA1 and BRCA2 mutations", Cell Cycle, vol. 10(8):1192-1199, Apr. 2011.

Orthwein et al., "A mechanism for the suppression of homologous recombination in G1 cells", Nature, vol. 528:422-426, Dec. 2015.

Shirley et al., PALB2 is an integral component of the BRCA complex required for homologous recombination repair, PNAS, vol. 106(7):7155-60, Apr. 2009.

Zhang et al., "PALB2 Links BRCA1 and BRCA2 in the DNA-Damage Response", Current Biology, vol. 19(6):524-529, Mar. 2009.

International Search Report and Written Opinion issued on International Patent Application No. PCT/CA2016/000057, dated May 24, 2016.

Mao et al., Comparison of Nonhomologous End Joining and Homologous Recombination in Human Cells, *DNA Repair (Amst)*. Oct. 1, 2008; 7(10): 1765-1771.

Sonoda et al., Differential Usage of Non-Homologous End-Joining and Homologous Recombination in Double Strand Break Repair, *DNA Repair*, Sep. 8, 2006; 5:9-10:1021-9.

Communication pursuant to Article 94(3) EPC issued on European Patent Application No. 16758390.5, dated Feb. 17, 2020.

Office Action issued on Japanese Patent Application No. 2017-546726, dated Mar. 17, 2020.

Olivieri et al., A Genetic Map of the Response to DNA Damage in Human Cells, Cell, vol. 182(2):481-496.e21, Jul. 2020.

Slabicki et al, A Genome-Scale DNA Repair RNAi Screen Identifies SPG48 as a Novel Gene Associated with Hereditary Spastic Paraplegia, PLoS Biology, vol. 8(6):e1000408, Jun. 2010.

Zimmermann et al., CRISPR screens identify genomic ribonucleotides as a source of PARP-trapping lesions, Nature, vol. 559(7713): 285-289, Jul. 2018.

* cited by examiner

G1-synchronized U2OS cells 1 h post-IR (2 Gy)

a
PALB2
WT 14-KEKLKEKLAFLKREYSKTLARLQRAQRAEKIK-45
KR 14-RERLRERLAFLRREYSRTLARLQRAQRAERIR-45
KR/K3 14-RERLREKLAFLKREYSKTLARLQRAQRAERIR-45
          20    25    30

FIG 2c
FIG 2d
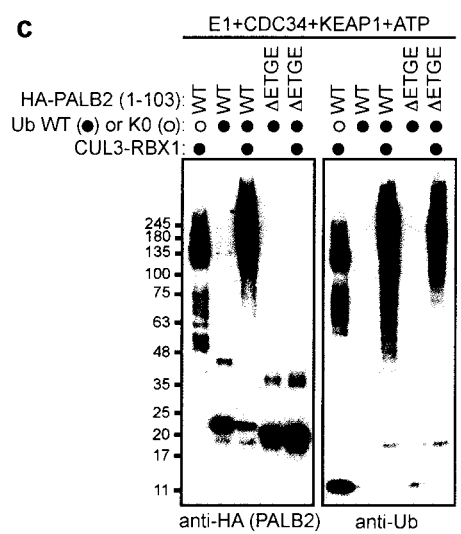
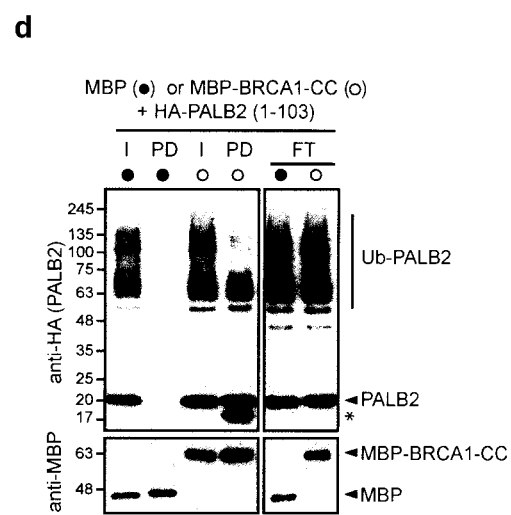

FIG 3a
FIG 3b
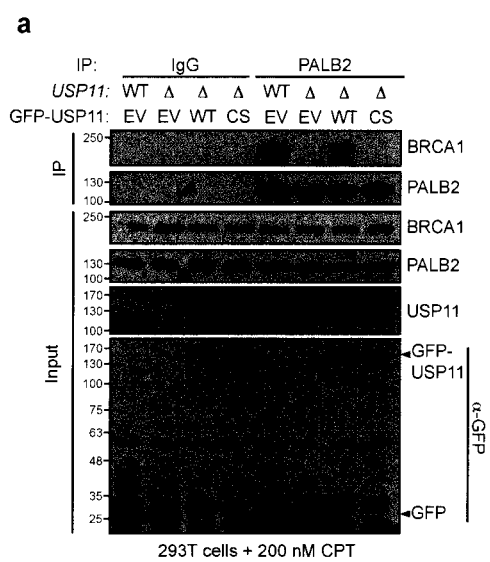
293T cells + 200 nM CPT
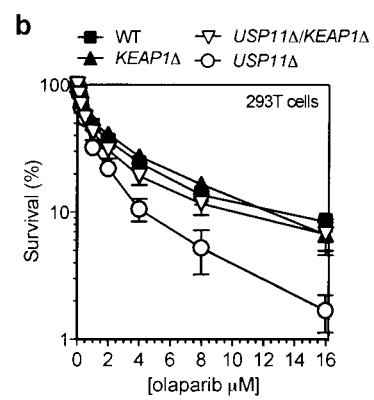
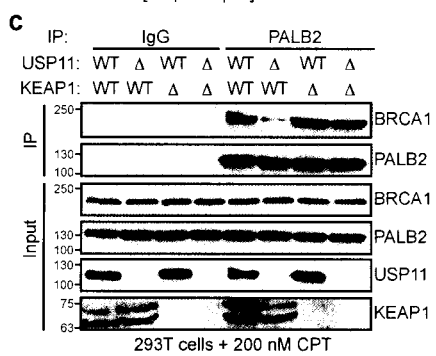
293T cells + 200 nM CPT
FIG 3c FIG 3d
FIG 3e
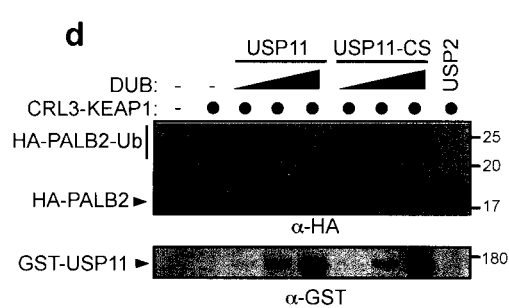
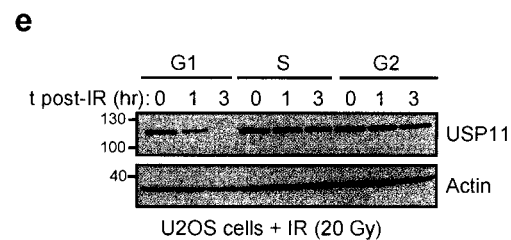
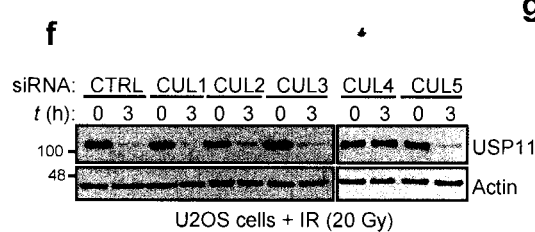
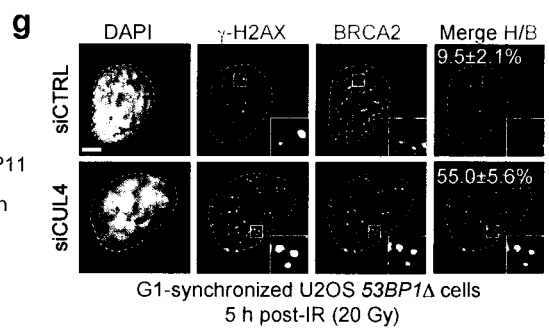
FIG 3f
FIG 3g FIG 4c
FIG 4d
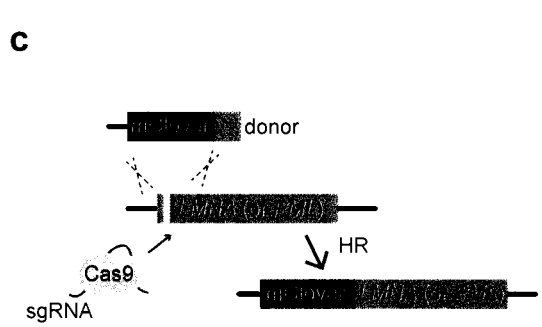
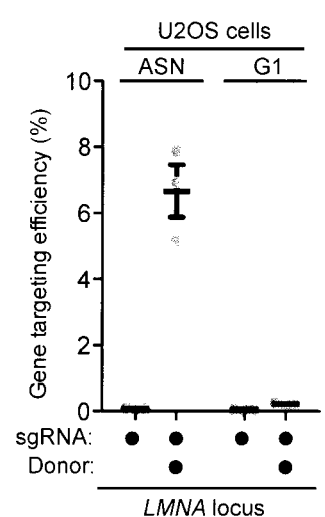
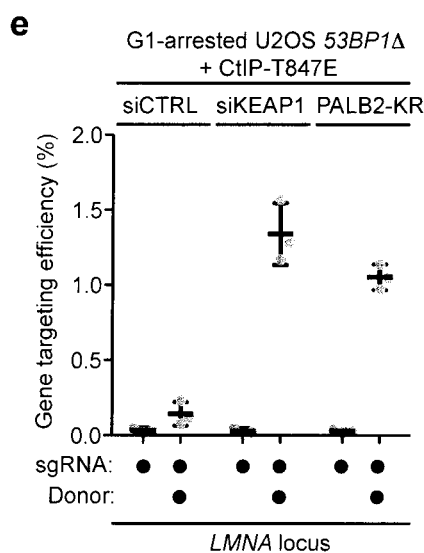
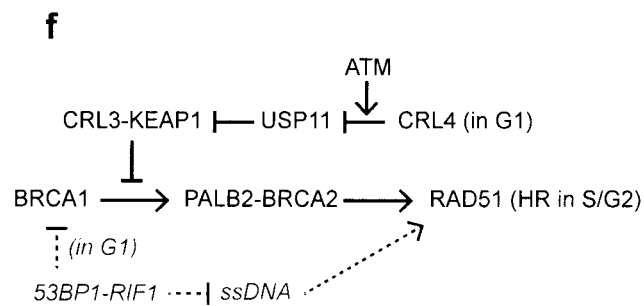
FIG 4f
FIG 4e FIG 5a
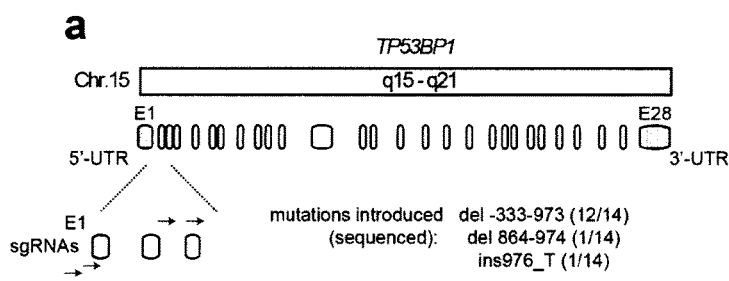
FIG 5b
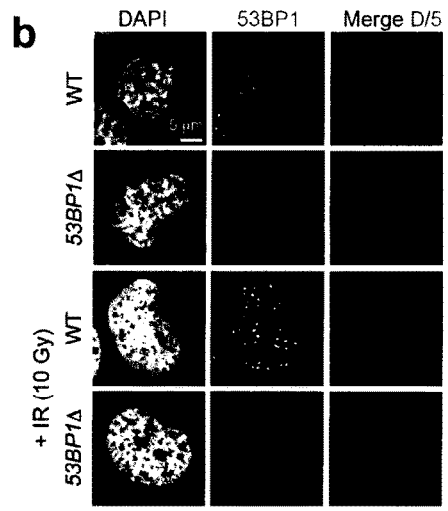
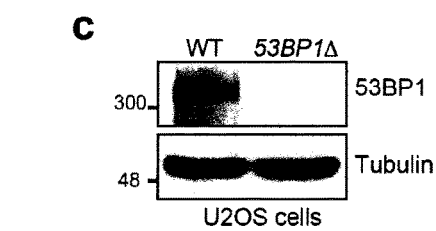
FIG 5c FIG 5d
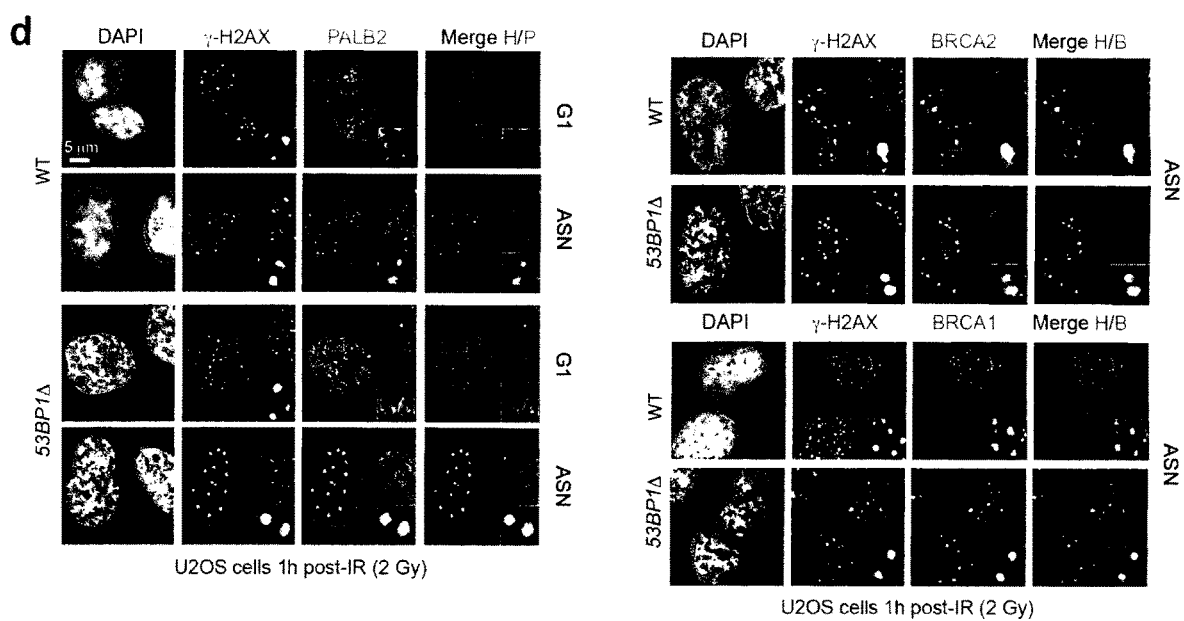
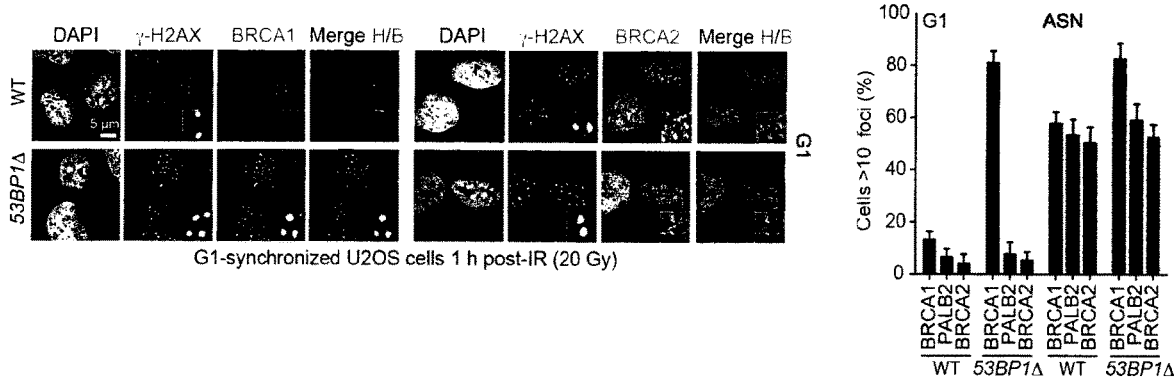
FIG 5e FIG 6a
FIG 6b
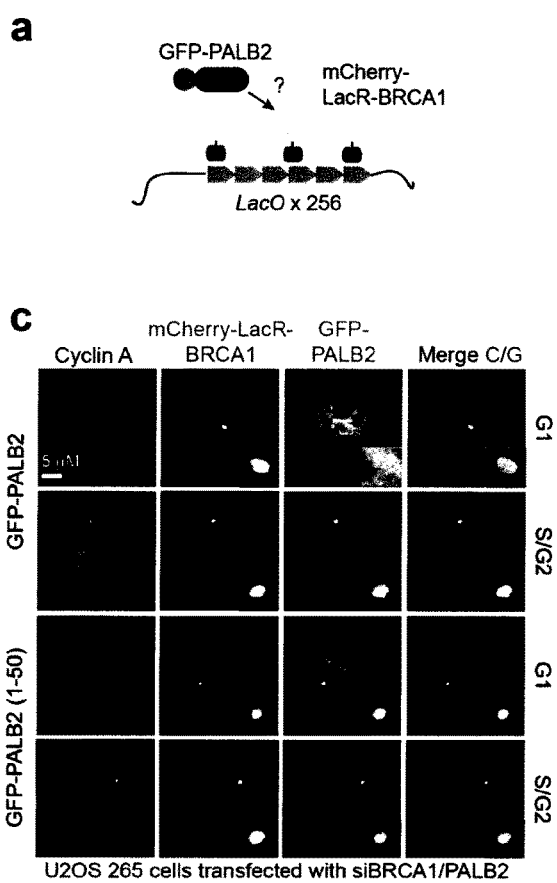
FIG 6c
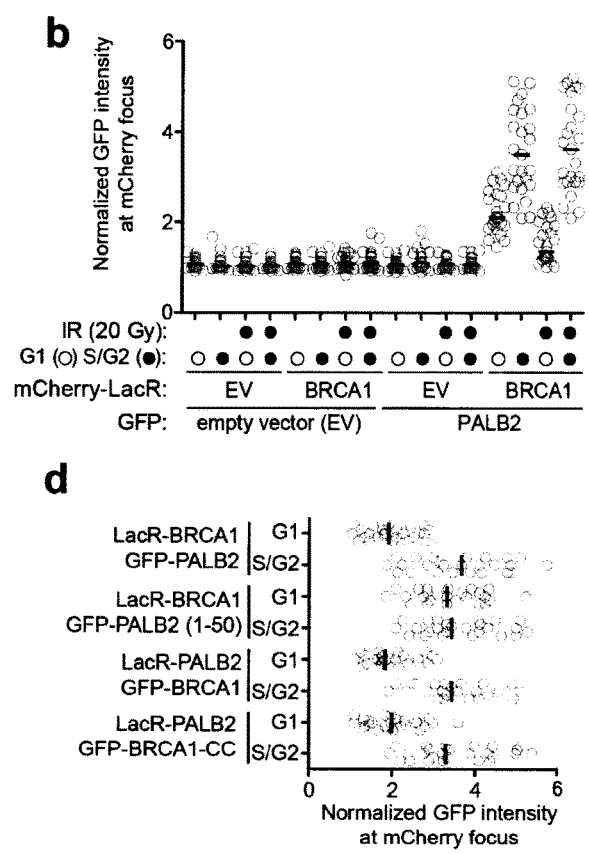
FIG 6d FIG 7a
FIG 7c
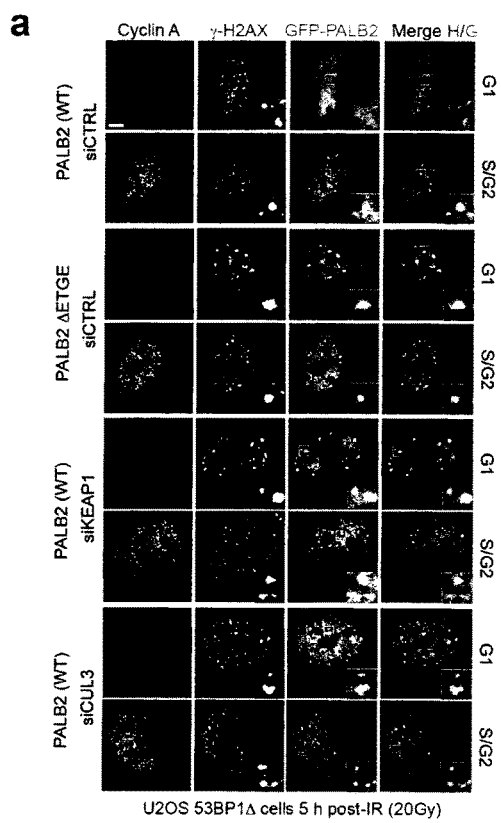
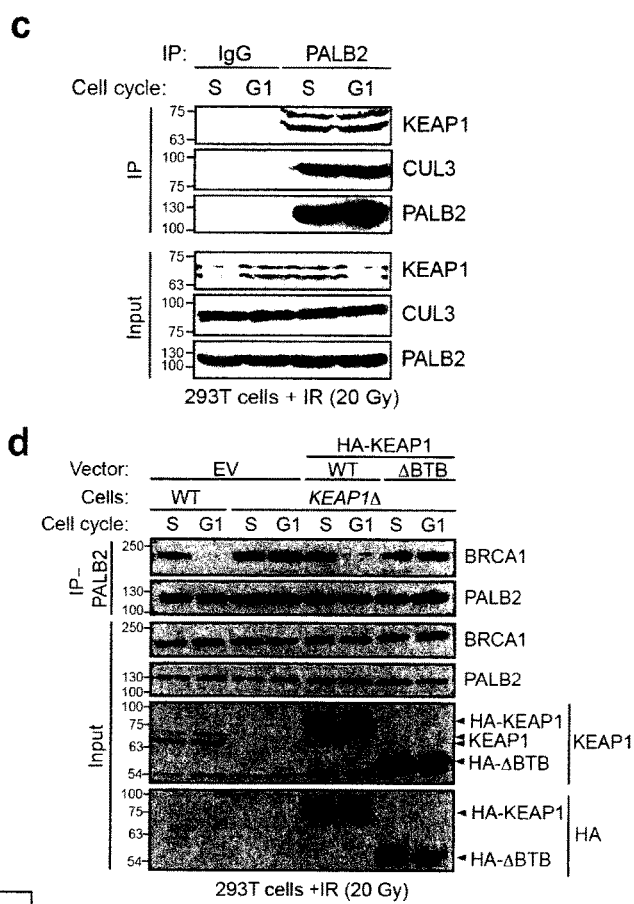
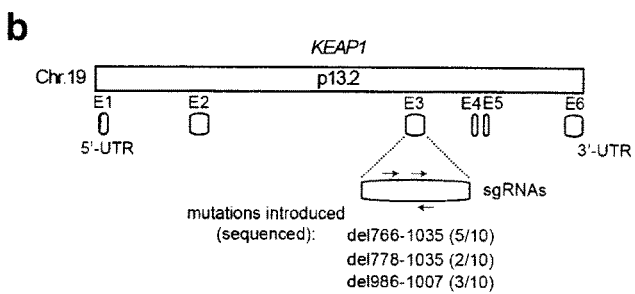
FIG 7b
FIG 7d FIG 7e
FIG 7f
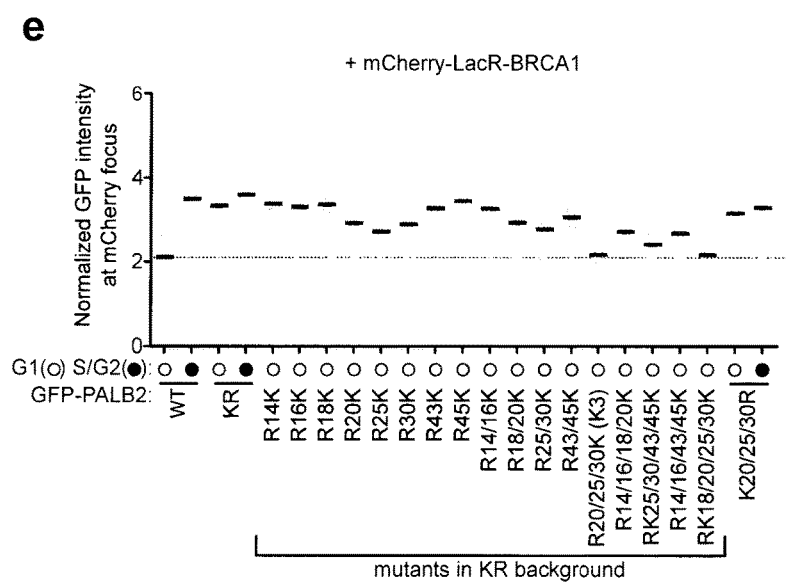
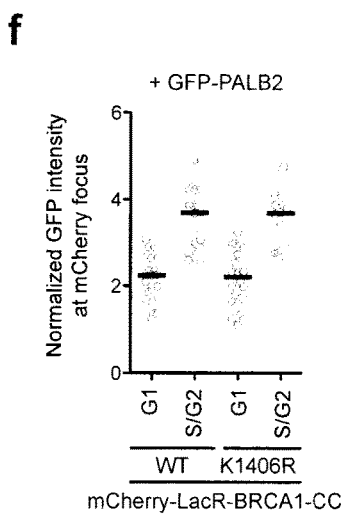

FIG 8a
FIG 8b
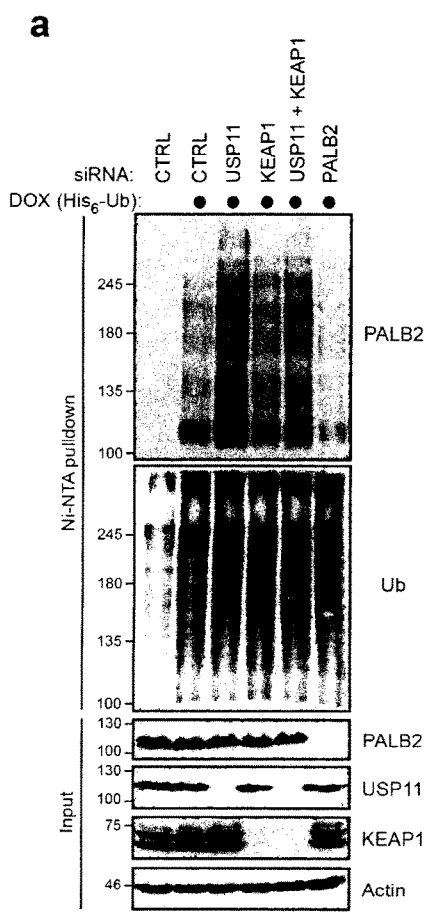
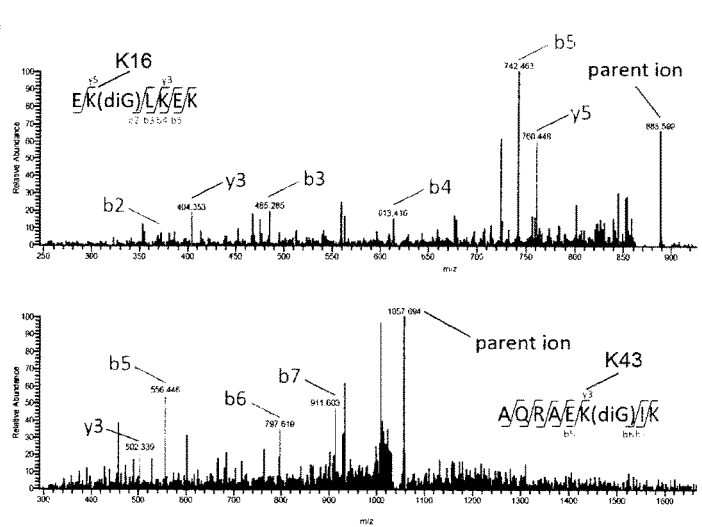
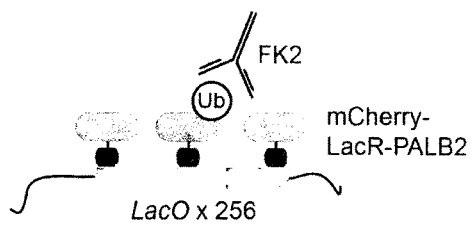
FIG 8c

FIG 8d
FIG 8e
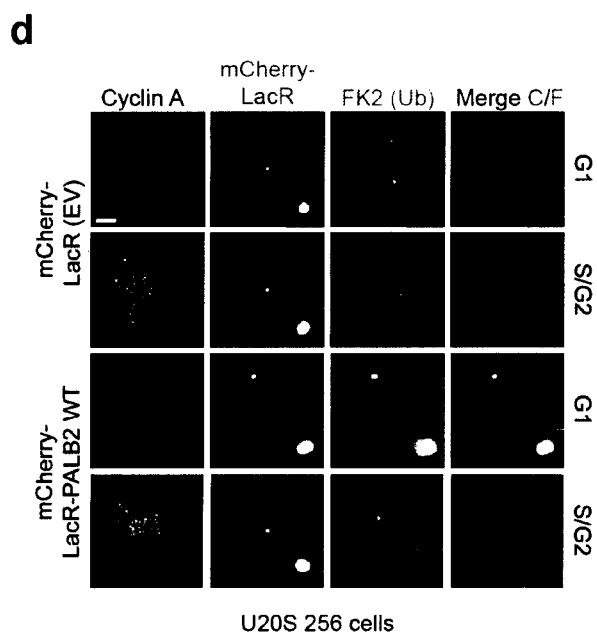
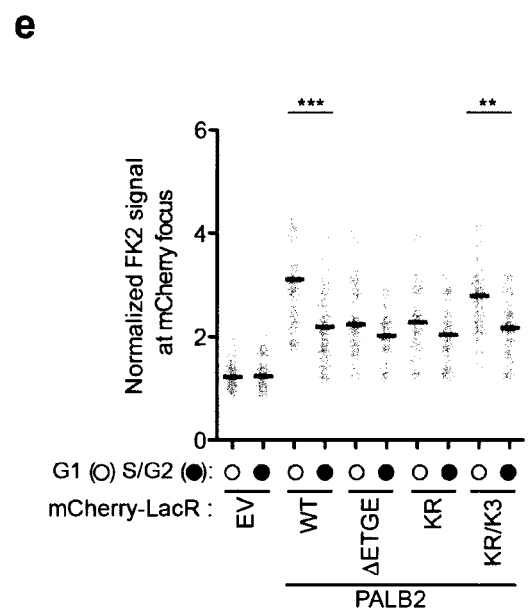

FIG 9a
FIG 9b
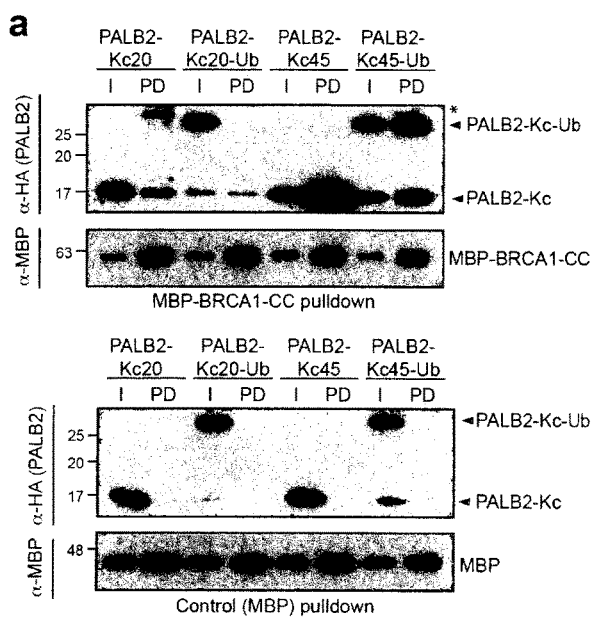
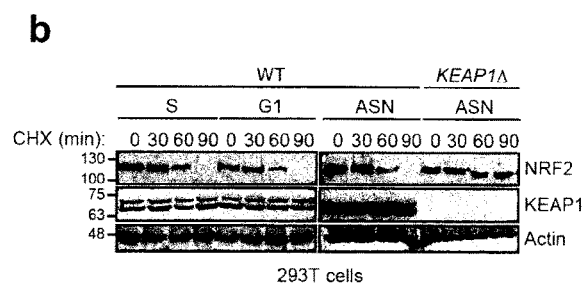
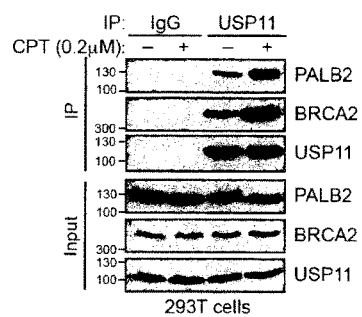
FIG 9c

FIG 9d
FIG 9e
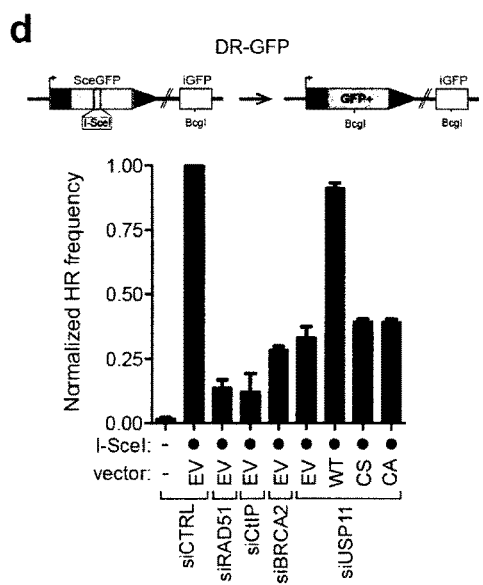
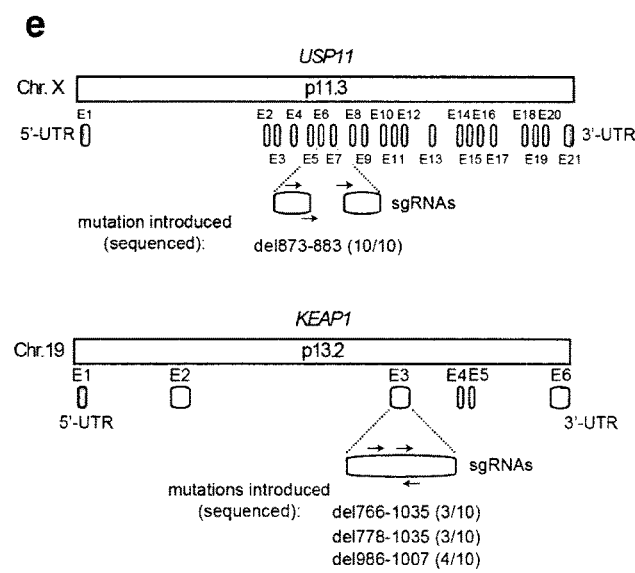
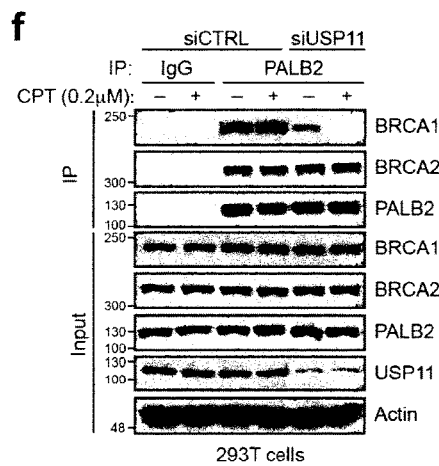
FIG 9f

FIG 10a
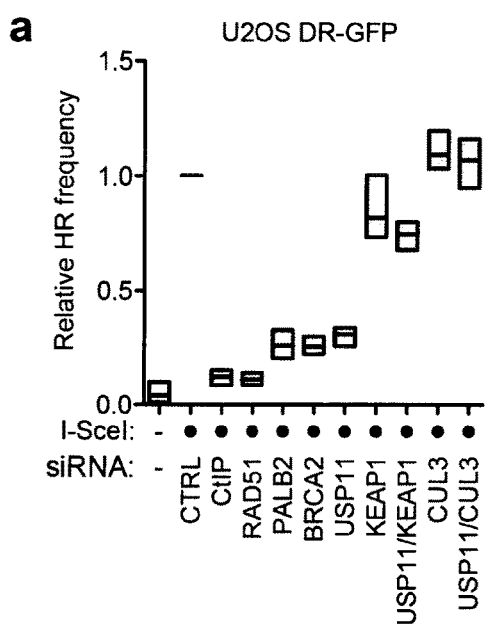
FIG 10b
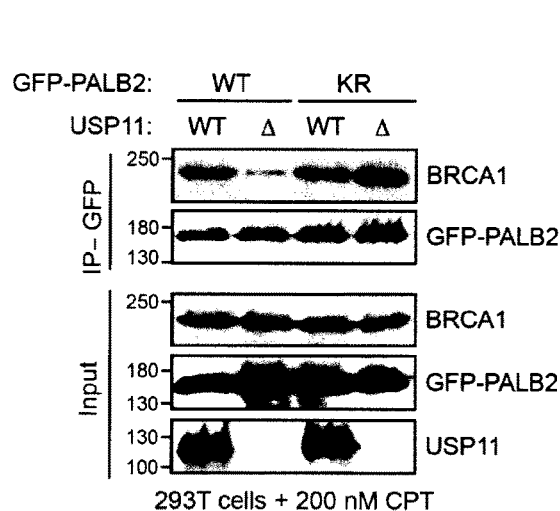
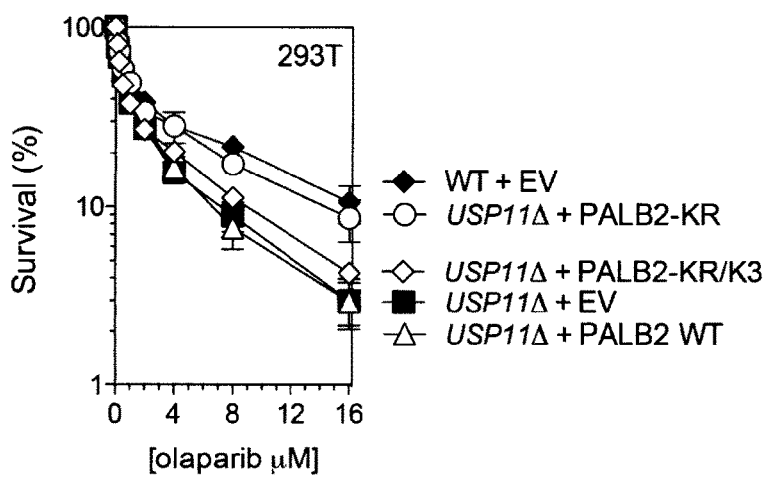
FIG 10c

FIG 12a
FIG 12b
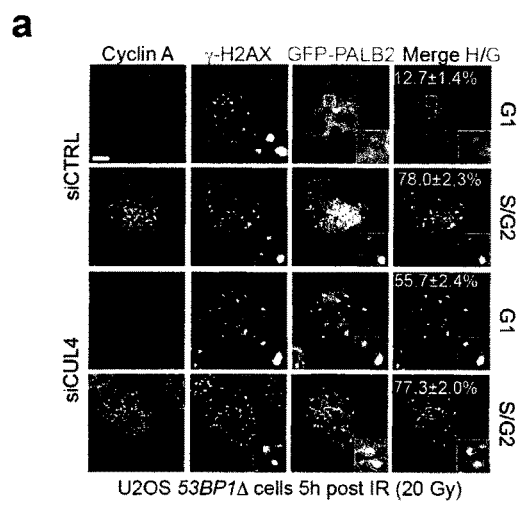
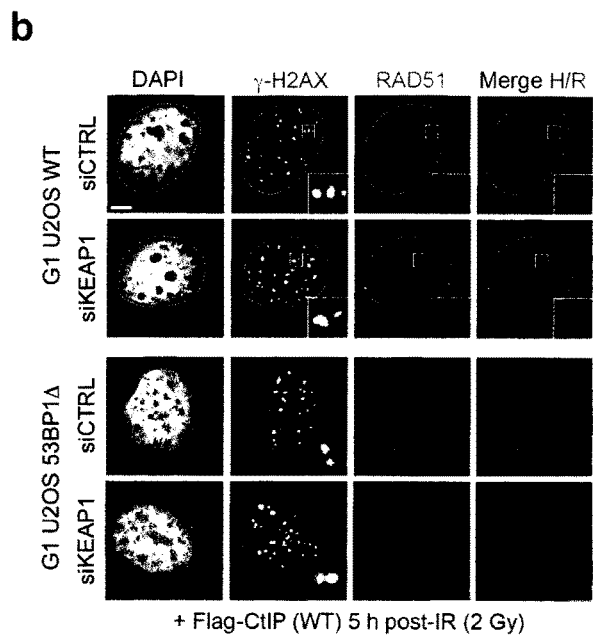
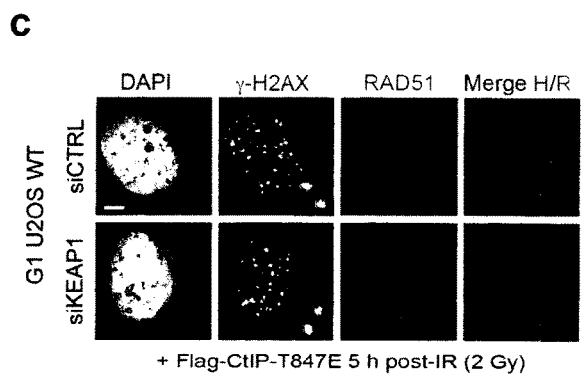
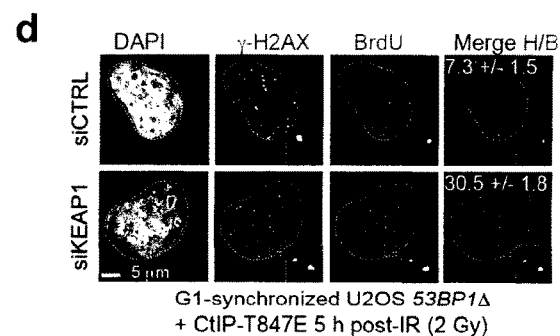
FIG 12c
FIG 12d

FIG 12e
FIG 12f
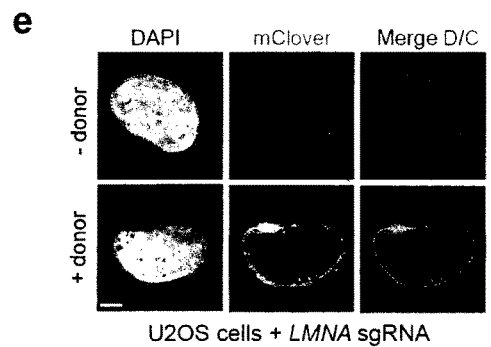
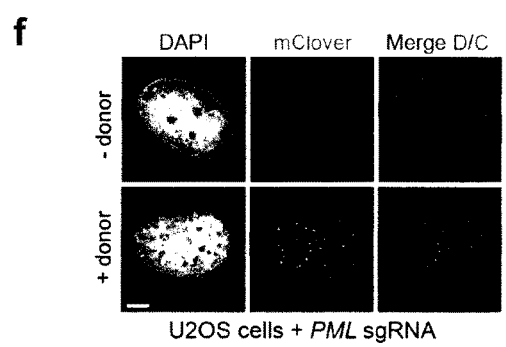
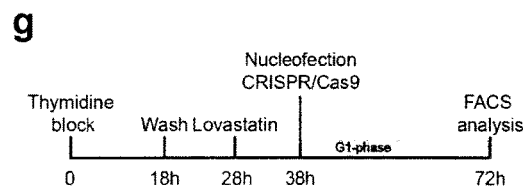
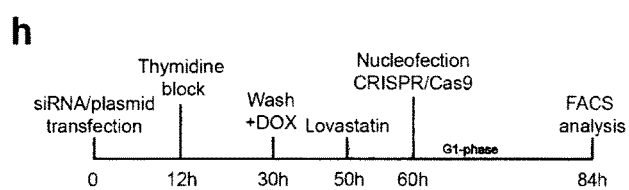
FIG 12g
FIG 12h

FIG 13a
FIG 13b
FIG 13c
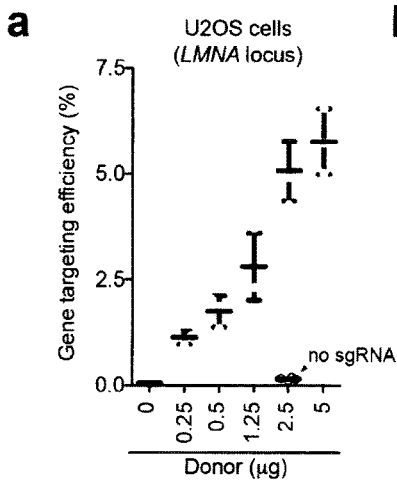
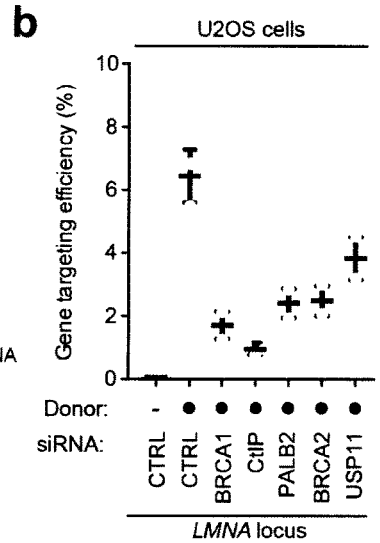
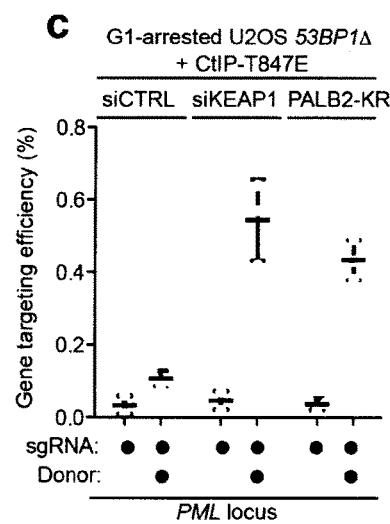
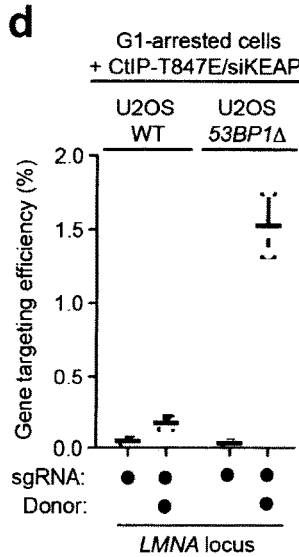
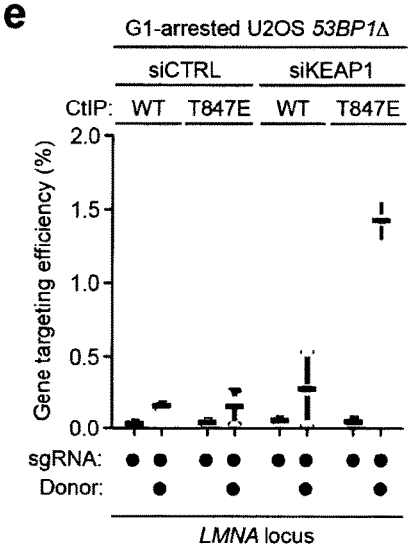
FIG 13d
FIG 13e FIG 14a
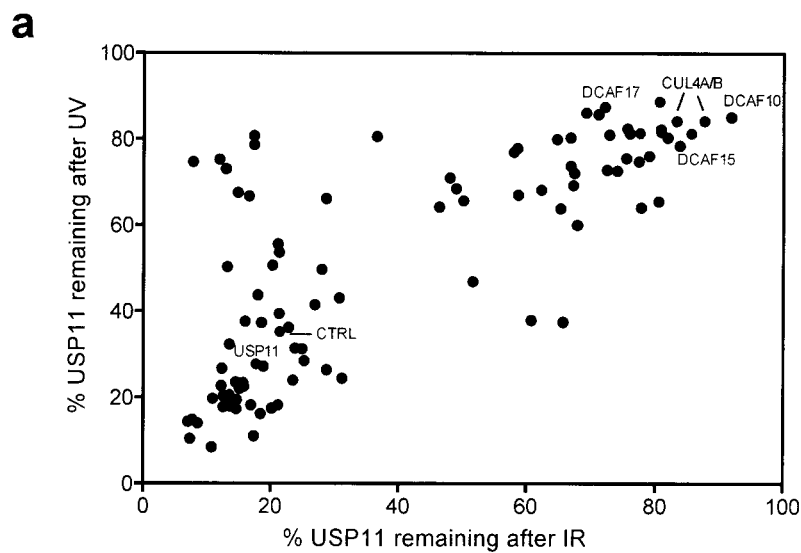
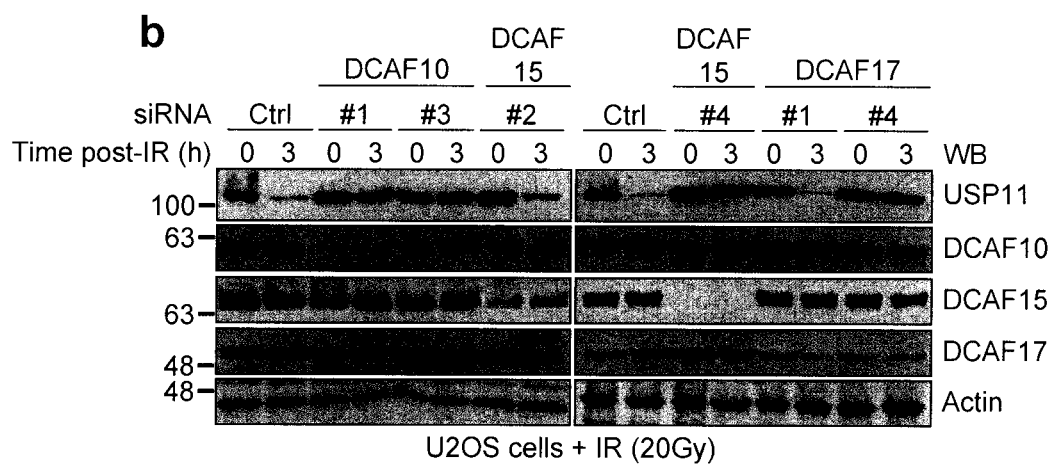
FIG 14b FIG 15a
FIG 15c
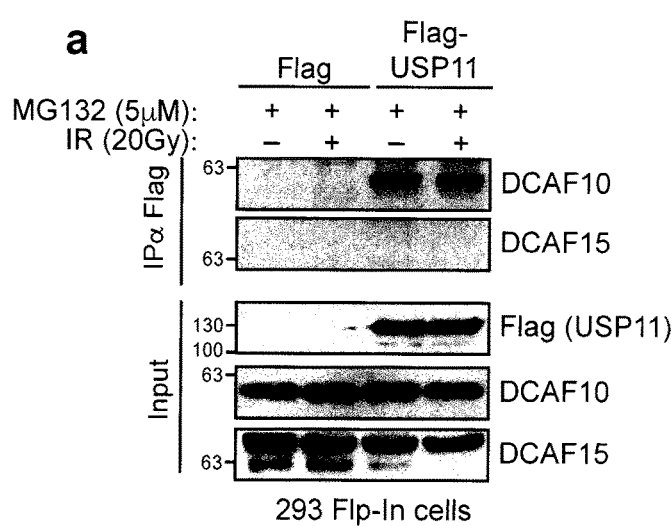
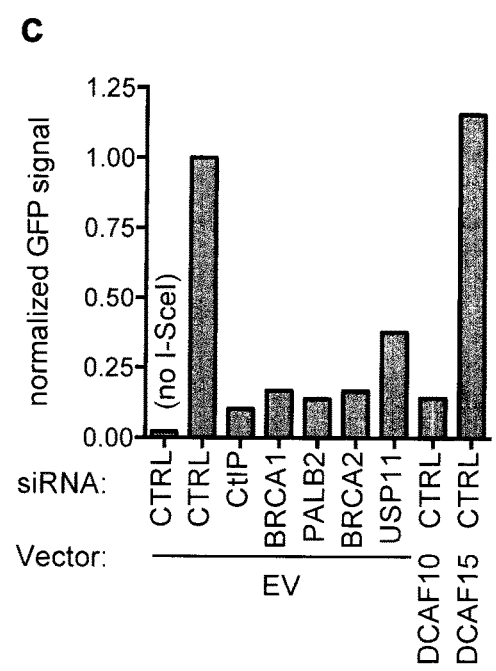
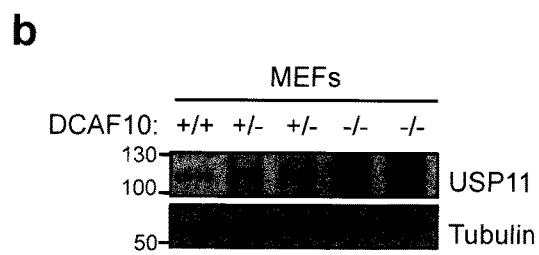
FIG 15b

HOMOLOGOUS RECOMBINATION FACTORS

FIELD OF THE INVENTION

The invention relates to factors that influence or regulate homologous recombination, methods to monitor these factors, the use of these factors to screen for agents that modulate homologous recombination, and methods to modulate homologous recombination.

BACKGROUND OF THE INVENTION

The breast and ovarian tumour suppressors BRCA1, PALB2 and BRCA2 promote DNA double-strand break (DSB) repair by homologous recombination (HR) [8-10]. BRCA1 acts in this process minimally at two discrete steps. Firstly, it promotes DNA end resection [11, 12], the initiating step in HR that involves the nucleolytic processing of breaks to produce the single-stranded (ss) DNA necessary for homology search and strand invasion [1]. Secondly, BRCA1 interacts with PALB2 [13-15] to direct the recruitment of BRCA2 [13] and RAD51 [16, 17] to DSB sites. The accumulation of BRCA1 on the chromatin that flanks DSB sites is strikingly suppressed in G1 cells [18], reminiscent of the potent inhibition of homologous recombination in this phase of the cell cycle. The inhibition of BRCA1 recruitment in G1 is dependent on the 53BP1 and RIF1 proteins [18, 19], two inhibitors of end-resection [18-22]. BRCA1 is also involved in promoting the recruitment of BRCA2 through its interaction with PALB2 [13-15].

Tumors with compromised ability to repair double-strand DNA breaks by HR, including those with defects in BRCA1 and BRCA2, have been shown to be highly sensitive to poly ADP-ribose polymerase (PARP) inhibitors. PARP inhibitors have also been proposed for treating other conditions such as stroke, myocardial infarction, inflammatory bowel disorders, head trauma, and neurodegenerative diseases. Inhibition of ubiquitin-specific peptidase 11 (USP11) has been shown to hypersensitize cells to PARP inhibitors and it has been proposed that USP11 status or the status of other HR-proteins in tumors may provide biomarkers for use of PARP inhibitors (Wiltshire et al, JBC 285(19), 14565-14571, 2010).

Identification and assessment of factors that influence or regulate homologous recombination repair proteins and the identification of events that are both necessary and sufficient to suppress HR in G1 cells is desirable. In addition, identification and assessment of factors that influence or regulate USP11 may facilitate the selection and monitoring of PARP inhibitor treatments, and in particular selection of treatments that reverse or delay emergence of PARP inhibitor resistance.

SUMMARY OF THE INVENTION

The present inventors have found that the cell cycle tightly controls the interaction of BRCA1 with PALB2-BRCA2 in order to constrain BRCA2 function to the S/G2 phases. The BRCA1-interaction site on PALB2 is targeted by an E3 ubiquitin ligase composed of KEAP1, a PALB2-interacting protein [6], in complex with cullin 3 (CUL3)-RBX1 [7]. PALB2 ubiquitylation suppresses its interaction with BRCA1 and is counteracted by the deubiquitylase USP11, which is itself under cell cycle control. Restoration of the BRCA1-PALB2 interaction combined with the activation of DNA end resection was sufficient to induce HR in G1-phase cells, as measured by RAD51 recruitment, unscheduled DNA synthesis and a CRISPR/Cas9-based gene targeting assay. The mechanism prohibiting HR in G1 minimally consists of the suppression of DNA end resection coupled to a multi-step block to BRCA2 recruitment to DNA damage sites that involves the inhibition of BRCA1-PALB2-BRCA2 complex assembly. The ability to induce HR in G1 cells with defined factors may be used in gene targeting applications in non-dividing cells or cells that are dormant in G1 phase. The findings also provide a basis for targeting USP11 in combination with poly(ADP-ribose) polymerase (PARP) inhibitors.

The present inventors have also found that USP11 is regulated by a cell cycle-CULLIN4-RING-ligase (CRL4) and DCAF10 acts as an adaptor for the USP11 E3 ligase.

The invention provides a method for monitoring activity of USP11 in a sample by assaying the interaction of BRCA1 and PALB2.

The invention provides a method for monitoring activity of USP11 in a sample by assaying the interaction of BRCA1, PALB2, and BRCA2.

The invention provides a method for monitoring activity of USP11 in a sample by assaying the interaction of USP11 and PALB2.

The invention provides a method for monitoring activity of USP11 in a sample by assaying DCAF10.

The invention provides a method for monitoring activity or expression of USP11 in a sample by assaying for complexes of (a) BRCA1 and PALB2; (b) BRCA1, PALB2, and BRCA2; (c) USP11 and PALB2; and/or (d) USP11 and DCAF10.

In an aspect, the invention provides a method for monitoring activity or expression of USP11 in a sample comprising (i) isolating complexes of (a) BRCA1 and PALB2; (b) BRCA1, PALB2, and BRCA2; (c) USP11 and PALB2; and/or (d) USP11 and DCAF10 in the sample; (ii) measuring the levels of the complexes; and (iii) detecting an increase or decrease in the activity or expression of the complexes as compared to a control as an indication of the activity or expression of USP11.

In an aspect, the invention provides a method for monitoring activity or expression of USP11 in a sample comprising (i) isolating complexes of (a) BRCA1 and PALB2; (b) BRCA1, PALB2, and BRCA2; (c) USP11 and PALB2; and/or (d) USP11 and DCAF10 in the sample by immunological purification; (ii) measuring the levels of the complexes; and (iii) detecting an increase or decrease in the activity or expression of the complexes as compared to a control as an indication of the activity or expression of USP11.

In an aspect, the invention provides a method for monitoring activity or expression of USP11 in a sample comprising (i) isolating complexes of (a) BRCA1 and PALB2; (b) BRCA1, PALB2, and BRCA2; (c) USP11 and PALB2; and/or (d) USP11 and DCAF10 in the sample; (ii) preparing peptides or peptide fragments from the isolated complexes; and (iii) subjecting the peptides or peptide fragments to mass spectrometry to thereby monitor the activity or expression of USP11.

The invention provides a method for monitoring activity or expression of USP11 in a sample by assaying ubiquitylation of PALB2, in particular ubiquitylation of the N-terminus of PALB2.

In an aspect, the invention provides a method for monitoring activity or expression of USP11 in a sample by assaying ubiquitylation of PALB2 comprising measuring the amount of polyubiquitin bound to CRL3-KEAP1 E3 ligase in the sample and detecting an increase or decrease in polyubiquitin bound to CRL3-KEAP1 E3 ligase as compared to a control as an indication of the activity or expression of USP11.

In another aspect, the invention provides a method for monitoring activity or expression of USP11 in a sample by assaying ubiquitylation of PALB2 comprising measuring the activity of CRL3-KEAP1 E3 ligase, and detecting an increase or decrease in CRL3-KEAP1 E3 ligase activity as compared to a control as an indication of the activity or expression of USP11.

The methods of the invention may be performed in the presence or absence of a test compound or agent and detection of an increase or decrease in activity or expression of one or more of USP11, DCAF10, PALB2, PALB2 ubiquitylation, BRCA1-PALB2-BRCA2 complex, PALB2-USP11 complex, KEAP1, USP11-DCAF complex, CRL3-KEAP1 complex, CRL3-KEAP1-PALB2 complex, and KEAP1-PALB2 complex, as compared to a control in the absence of the test compound or agent indicates that the test compound or agent may be useful as a therapeutic agent, or for modulating homologous recombination.

In an aspect, the invention provides a method for identifying or evaluating an agent for its ability to sensitize or reverse or delay emergence of resistance to PARP inhibitors by determining the effect of the agent on USP11 activity or expression using a method of the invention.

In an aspect, the invention relates to a method of identifying or evaluating an agent for its ability to sensitize cells or reverse or delay emergence of resistance to PARP inhibitors by determining the effect of the agent on KEAP1, CRL3-KEAP1, KEAP1-PALB2 or CRL3-KEAP1.

In an aspect, the present invention provides methods of detecting an anti-cancer agent comprising performing a test assay comprising contacting an immortalized cell with a test compound and assaying USP11 activity or expression using a method of the invention.

The invention also provides a method for identifying or evaluating an agent for its ability to modulate homologous recombination comprising determining the effect of a test compound or agent on one or more of USP11, DCAF10, PALB2, PALB2 ubiquitylation, BRCA1-PALB2-BRCA2 complex, PALB2-USP11 complex, KEAP1, USP11-DCAF10 complex, CRL3-KEAP1 complex and CRL3-KEAP1-PALB2 complex.

The invention provides a method of screening for a therapeutic agent for treatment of a disease associated with defects in HR (i.e., HR Disease), comprising identifying an agent that disrupts or modulates one or more of USP11, PALB2, PALB2 ubiquitylation, DCAF10, BRCA1-PALB2-BRCA2 complex, PALB2-USP11 complex, KEAP1, USP11-DCAF10 complex, CRL3-KEAP1 or CRL3-KEAP1-PALB2 complex.

The screening methods of the invention may further comprise conducting therapeutic profiling of the identified agents or further analogs thereof, for efficacy and toxicity in animals; optionally formulating a pharmaceutical composition including one or more agents identified as having an acceptable therapeutic profile; and optionally administering the agent to a subject or individual.

The invention provides methods of treating a HR Disease in an individual comprising identifying an agent that modulates HR in accordance with a method of the invention and administering the agent to the individual.

In some embodiments, the invention provides a method for sensitizing cells to PARP inhibitors in an individual comprising identifying an agent that sensitizes cells to PARP inhibitors in accordance with a method of the invention and administering the agent to the individual.

In some embodiments, the invention provides a method for reversing or delaying emergence of resistance to PARP inhibitors in an individual comprising identifying an agent that reverses or delays emergence of resistance to PARP inhibitors in accordance with a method of the invention and administering the agent to the individual.

In some embodiments, the present invention provides methods of treating cancer in an individual comprising identifying an anti-cancer agent identified in accordance with a method of the invention and administering the agent to the individual.

The invention also provides a method for predicting a response or categorizing a response to a PARP inhibitor in a subject comprising assaying one or more of USP11, DCAF10, BRCA1, BRCA2, PALB2, KEAP1, CRL3, CRL3-KEAP1, USP11-DCAF10 complex, BRCA1-PALB2-BRCA2 complex, PALB2-USP11 complex and CRL3-KEAP1-PALB2 complex in a sample from the subject using a method of the invention. In an aspect, a method is provided for predicting a response or categorizing a response to a PARP inhibitor in a subject comprising assaying USP11 activity or expression in a sample from the subject using a method of the invention. In an aspect, a method is provided for predicting a response or categorizing a response to a PARP inhibitor in a subject comprising assaying PALB2 activity or expression in a sample from the subject using a method of the invention.

In an aspect, a subject is categorized as responsive to a PARP inhibitor if there is a decrease in one or more of USP11, DCAF10, BRCA1, BRCA2, PALB2, KEAP1, CRL3, USP11-DCAF10, CRL3-KEAP1, BRCA1-PALB2 and BRCA1-PALB2-BRCA2 activity or expression or PALB2 ubiquitylation compared to a control. In an aspect, a subject is categorized as responsive to a PARP inhibitor if there is an increase in one or more of USP11, DCAF10, BRCA1, BRCA2, PALB2, KEAP1, CRL3, USP11-DCAF10, CRL3-KEAP1, BRCA1-PALB2 and BRCA1-PALB2-BRCA2 activity or expression or PALB2 ubiquitylation compared to a control.

A method of predicting responsiveness to a PARP inhibitor may further comprise administering the PARP inhibitor to the individual.

The invention provides a method for treating a patient in need of treatment with a PARP inhibitor comprising (a) requesting a test providing the results of an analysis to determine if the patient is sensitive or responsive to the PARP inhibitor by detecting one or more of USP11, DCAF10, BRCA1, BRCA2, PALB2, KEAP1, USP11-DCAF10, CRL3, CRL3-KEAP1, BRCA1-PALB2 and BRCA1-PALB2-BRCA2, in a sample from the subject and comparing to a control to determine if the patient is sensitive or responsive to the PARP inhibitor; and (b) administering the PARP inhibitor to the patient if the patient is sensitive or responsive to the PARP inhibitor. In an aspect of this method of the invention, the patient has breast cancer. In an aspect of this method of the invention, the patient has ovarian cancer.

In an aspect, the invention provides a method for treating a patient in need of treatment with a PARP inhibitor comprising (a) requesting a test providing the results of an analysis to determine if the patient is sensitive to the PARP inhibitor by detecting USP11, DCAF10, BRCA1, BRCA2, PALB2, KEAP1 and/or CRL3 in a sample from the subject and comparing to a control to determine if the patient is sensitive to the PARP inhibitor; and (b) administering the PARP inhibitor to the patient if the patient is sensitive to the PARP inhibitor. In an aspect of this method of the invention, the patient has breast cancer. In an aspect of this method of the invention, the patient has ovarian cancer.

The invention further provides a method for assigning an individual to one of a plurality of categories in a clinical trial for a PARP inhibitor comprising assaying USP11, DCAF10, PALB2, PALB2 ubiquitylation, BRCA1-PALB2-BRCA2 complex, PALB2-USP11 complex, USP11-DCAF complex, KEAP1, CRL3-KEAP1 and/or CRL3-KEAP1-PALB2 complex in a sample from the subject using a method of the invention.

The invention also provides pharmacogenetic methods for determining suitable treatment regimens for diseases, in particular cancer, and methods for treating patients, based around selection of patients based on PARP responsiveness, in particular USP11 activity.

The methods of the invention, in particular methods for assaying USP11 activity or CRL3-KEAP1 activity, may be used as a read out in animal model based screening methods for new therapeutic approaches and compounds. In an aspect, a method of the invention is utilized to predict the efficacy of potential new treatments in animal models for disease states.

The invention provides a method for activating or modulating (e.g., promoting) homologous recombination in a cell comprising:
(a) promoting or stimulating the assembly or occurrence of BRCA1-PALB2 or BRCA1-PALB2-BRCA2 complexes in the cell;
(b) activating or stimulating BRCA1 recruitment to DNA double-strand break (DSB) sites;
(c) contacting the cell with BRCA1-PALB2 or BRCA1-PALB2-BRCA2 complexes;
(d) inhibiting or removing KEAP1 or CRL3-KEAP1;
(e) inhibiting the degradation of USP11 or promoting USP11 activity; and/or
(f) inhibiting or removing DCAF10.

The invention provides a method for activating or modulating homologous recombination in a cell, in particular a cell in G1 phase of the cell cycle (G1) or G0 phase of the cell cycle, comprising administering, or stimulating assembly of BRCA1-PALB2 or BRCA1-PALB2-BRCA2 complexes in the cell.

The invention also provides a method for activating or modulating homologous recombination in a cell, in particular a cell in G1 phase of the cell cycle (G1) or G0 phase of the cell cycle (G0), comprising promoting or stimulating the assembly or occurrence of BRCA1-PALB2 or BRCA1-PALB2-BRCA2 complexes in the cell.

The invention also provides a method for activating or modulating homologous recombination in a cell, in particular a cell in G1 phase of the cell cycle (G1) or G0 phase of the cell cycle (G0), comprising administering to the cell or contacting the cell with BRCA1-PALB2 or BRCA1-PALB2-BRCA2 complexes.

The invention also provides a method for repairing DNA double-strand breaks in a cell in the G1 phase of the cell cycle (G1) or G0 phase of the cell cycle (G0), comprising promoting or stimulating the assembly or occurrence of BRCA1-PALB2 or BRCA1-PALB2-BRCA2 complexes in the cell.

In aspects of the invention, the assembly of BRCA1-PALB2 or BRCA1-PALB2-BRCA2 complexes is promoted or stimulated by administering an agent that promotes or stimulates such assembly or an agent that promotes or stimulates such assembly identified using a method of the invention. In an embodiment, the agent is USP11 or an agonist of USP11. In an embodiment, the agent is an inhibitor of CRL-KEAP1. In an embodiment, the agent is an inhibitor of KEAP1. In an embodiment, the agent is a PALB2 mutant. In an embodiment, the agent is a PALB2 mutant that disrupts its interaction with KEAP1. In an embodiment, the agent is a PALB2 comprising mutations of its Lys20, Lys25 and Lys30 residues.

A method for activating or modulating homologous recombination in a cell may be performed in a cell wherein single strand DNA (ssDNA) generation pathways are activated. In an aspect, ssDNA generation pathways in the cell are activated by DNA end resection.

The invention also provides a method for activating or modulating homologous recombination in a cell, in particular a cell in the G1 phase of the cell cycle (G1) or G0 phase of the cell cycle (G0) in which DNA end resection is or has been activated generating single-stranded DNA, comprising promoting or stimulating the assembly or occurrence of BRCA1-PALB2 or BRCA1-PALB2-BRCA2 complexes in the cell.

The invention also provides a method for repairing DNA double-strand breaks in a cell in the G1 phase of the cell cycle (G1) or G0 phase of the cell cycle (G0) in which DNA end resection is or has been activated generating single-stranded DNA, comprising promoting or stimulating the assembly or occurrence of BRCA1-PALB2 or BRCA1-PALB2-BRCA2 complexes in the cell. In an embodiment, the assembly of the complexes is promoted or stimulated by administering an agent that modulates HR. In an embodiment, the agent is an agent that modulates HR identified using a method of the invention. In an embodiment, the agent is USP11 or an agonist of USP11. In an embodiment, the agent is an inhibitor of CRL-KEAP1. In an embodiment, the agent is an inhibitor of KEAP1. In an embodiment, the agent is a PALB2 mutant. In an embodiment, the agent is an inhibitor of DCAF10. In an embodiment, the agent is an inhibitor of a CULLIN4-RING-ligase.

The invention also provides a method for repairing DNA double-strand breaks in a cell in the G1 phase of the cell cycle (G1) or G0 phase of the cell cycle (G0) in which DNA end resection is or has been activated generating single-stranded DNA, comprising contacting the cell with BRCA1-PALB2 or BRCA1-PALB2-BRCA2 complexes.

In an aspect, the invention provides a method for activating or modulating homologous recombination in a cell, in particular a cell in G1 or G0, comprising the step of inhibiting KEAP1 or CRL3-KEAP1 or administering an inhibitor of KEAP1 or CRL3-KEAP1. In an aspect, the invention provides a method for activating or modulating homologous recombination in a cell, in particular a cell in G1 or G0, comprising the step of blocking the degradation of USP11 or promoting or stimulating USP11 activity. In an embodiment, the method comprises administering USP11 or an agonist thereof. In an aspect, the invention provides a method for activating or modulating homologous recombination in a cell, in particular a cell in G1 or G0, comprising the step of inhibiting CRL-KEAP1 or administering an inhibitor of KEAP1 or CRL3-KEAP1 and blocking the degradation of USP11 or promoting or stimulating USP1 activity.

The invention also provides a method for repairing DNA double-strand breaks in a cell in G1 or G0 in which DNA end resection is or has been activated generating single-stranded DNA, the method comprising (a) inhibiting KEAP1 or CRL3-KEAP1; (b) blocking the degradation of USP11 or promoting or stimulating USP11 activity; (c) administering USP11 or an agonist thereof; (d) administering an inhibitor of KEAP1 or CRL3-KEAP1; (e) administering an inhibitor of DCAF10; and/or (e) inhibiting CRL-KEAP1 and blocking the degradation of USP11.

A method for activating or modulating homologous recombination in a cell may further comprise activating or promoting single-strand DNA (ssDNA) generation pathways. In an aspect, ssDNA generation pathways are activated by DNA end resection.

A method for activating or modulating homologous recombination in a cell may further comprise a gene editing system. In an aspect the gene editing steps comprise contacting the cell with a nuclease. In aspects of the invention the gene editing system may correct a genomic modification.

The invention also provides a method for suppressing homologous recombination in a cell, in particular a cell in G1, comprising suppressing the assembly of BRCA1-PALB2 or BRCA1-PALB2-BRCA2 complexes in the cell. In an embodiment, the interaction is suppressed by administering KEAP1 or CRL3-KEAP1 or an agonist thereof. In an embodiment, the interaction is suppressed by administering a USP11 antagonist/inhibitor (e.g., mitoxantrone). In an embodiment, the interaction is suppressed by administering an agent that inhibits or suppresses HR identified using a method of the invention.

The invention further provides kits for performing methods of the invention.

The invention also provides a system comprising: an assay for determining the level of USP11 activity, complexes or biomarker levels in a sample obtained from the subject; a processor for processing the results; computer coded instructions for comparing the results with a database; and a user display for providing the results of the comparison. The database may comprise reference values for USP11 activity or biomarker levels.

The invention also contemplates the use of methods, kits, and systems of the invention in genome modification or editing.

In an aspect, the invention further contemplates the use of methods, compositions, kits, and systems of the invention in genome modification or editing, provided that said use is not a method for treatment of the human or animal body by surgery or therapy, and provided that said use is not a process for modifying the germ line genetic identity of human beings. Genome modification may comprise modifying a target polynucleotide sequence in a cell, modifying expression of a polynucleotide sequence in a cell, generating a model cell comprising a mutated disease gene, or knocking out a gene. A use of the invention may further comprise repairing or editing a cleaved target polynucleotide by inserting an exogenous template polynucleotide, wherein the repair or editing results in a mutation comprising an insertion, deletion, or substitution of one or more nucleotides of the target polynucleotide.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which:

FIG. 3. USP11 opposes the activity of CRL3-KEAP1. a, Normal IgG or PALB2 immunoprecipitation (IP) of extracts derived from camptothecin (CPT)-treated 293T cells of the indicated genotypes transfected with GFP-USP11 constructs. EV, empty vector; CS, C318S; WT, wild type. b, Clonogenic survival assays of 293T cells of the indicated genotypes treated with olaparib (mean±s.d., N>3). c, Normal IgG or PALB2 immunoprecipitation of extracts derived from CPT-treated 293T cells of the indicated genotypes. d, Immunoblots of deubiquitylation reactions containing ubiquitylated HA-tagged PALB2 (1-103) and increasing concentrations of glutathione S-transferase (GST)-USP11 or its C270S (CS) mutant. USP2 was used as a control. DUB, deubiquitylase. e, Cell cycle-synchronized U2OS cells were irradiated (20 Gy dose) and processed for immunoblotting. IR, ionizing radiation. f, Immunoblots of extracts from irradiated U2OS cells transfected with the indicated siRNAs. CTRL, control. g, Fluorescence micrographs of G1-synchronized and irradiated (20 Gy) 53BP1Δ U2OS cells transfected with the indicated siRNAs. The percentage of cells with more than five γ-H2AX-colocalizing BRCA2 foci is indicated (mean±s.d., N=3). Scale bars, 5 μm. a, c, d, f, Numbers to left or right indicate kDa.

FIG. 5. Suppression of PALB2-BRCA2 accumulation at DSB sites in G1 53BP1Δ cells. a, Schematic representation of human 53BP1 gene organization and targeting sites of sgRNAs used. Boxes indicate exons (E: yellow, coding sequence; brown, untranslated regions (UTRs)). The indels introduced by CRISPR/Cas9 and their respective frequencies are indicated. b, Wild-type (WT) and 53BP1Δ and U2OS cells were mock- or X-irradiated (10 Gy) before being processed for 53BP1 fluorescence microscopy. DAPI was used to stain DNA and trace the outline of the nucleus. c, Wild-type (WT) and 53BP1Δ U2OS cells were processed for 53BP1 immunoblotting. Tubulin was used as a loading control. d, Wild-type (WT) and 53BP1Δ U2OS cells either synchronized in G1 following a double-thymidine block and release or asynchronously dividing (ASN), were irradiated (2 Gy) and processed for γ-H2AX, PALB2, BRCA2 and BRCA1, immunofluorescence. The micrographs relating to BRCA1 and BRCA2 staining in G1 are found in FIG. 1a. e, Wild-type (WT) and 3BP1Δ U2OS cells synchronized in G1 after release from a double-thymidine block were irradiated (20 Gy) and processed for γ-H2AX, BRCA1 and BRCA2 immunofluorescence. On the left are representative micrographs for the G1-arrested cells and the quantitation of the full experiment is shown on the right (mean±s.d., N=3).

FIG. 7. Inhibition of the BRCA1-PALB2 interaction in G1 depends on CRL3-KEAP1. a, Representative micrographs of the experiment shown in FIG. 1d. b, Schematic representation of human KEAP1 gene organization and targeting sites of sgRNAs used as described in FIG. 5a. The indels introduced by CRISPR/Cas9 and their respective frequencies are indicated. c, Immunoprecipitation (IP) of PALB2 from extracts prepared from irradiated 293T cells. IP with normal IgG was performed as a control. d, 293T cells with the indicated genotypes were transfected with the indicated HA-KEAP1 constructs, synchronized in G1 or S phases and irradiated. Cells were processed for PALB2 immunoprecipitation (IP). EV, empty vector; WT, wild type. e, Quantification of U2OS 256 cells transfected with the indicated GFP-PALB2 mutants and mCherry-LacR-BRCA1. Cells were also stained with a cyclin A antibody to determine cell cycle position (N=3). f, Quantification of U2OS 256 cells transfected with GFP-PALB2 and mCherry-LacR-BRCA1-CC (wild type or K1406R mutant). Cells were also stained with a cyclin A antibody to determine cell cycle position. This panel shows that the sole lysine in the PALB2-interaction motif of BRCA1 is not involved in the cell cycle regulation of the PALB2-BRCA1 interaction. e, f, Each circle represents a cell analyzed and the bar is at the median (N=3).

FIG. 8. PALB2 is ubiquitylated by CRL3-KEAP1. a, HEK293 Flp-In T-REX cells expressing doxycycline (DOX)-inducible $His_6$-Ub were transfected with the indicated siRNAs. Cells were processed for Ni-NTA pull-down (IP). b, 293T cells transfected with an siRNA targeting USP11 and a Flag-PALB2 expression vector were processed for Flag immunoprecipitation followed by mass spectrometry (MS). Representative MS/MS spectra of tryptic diglycine (diG)-PALB2 peptides identified are shown (K16, top; K43, bottom), c, Schematic of the lacO/LacR chromatin-targeting system and the in vivo quantification of ubiquitylated PALB2. d, Representative micrographs of U2OS 256 cells transfected with the indicated mCherry-LacR-PALB2 vectors. Cells were processed for FK2 immunofluorescence. EV, empty vector. Scale bar, 5 e, Quantification of U2OS 256 cells transfected with the indicated mCherry-LacR-PALB2 vectors. Cells were processed for quantification of FK2 fluorescence at the LacO focus. Each circle represents a cell analyzed and the bar is at the median (N=3). Cells were also stained with a cyclin A antibody to determine cell cycle position. Statistical significance was determined by a Kruskall-Wallis test (*P<0.001; P<0.01).

FIG. 9. Analysis of KEAP1- and USP11-dependent modulation of PALB2 and homologous recombination. a, Site-specific chemical ubiquitylation of HA-PALB2 (1-103) at residue 20 (PALB2-KC20-Ub) and 45 (PALB2-KC45-Ub) was carried out by dichloroacetone linking. The resulting ubiquitylated PALB2 polypeptides along with their unmodified counterparts were subjected to pulldown with a fusion of MBP with the coiled-coil domain of BRCA1 (MBP-BRCA1-CC). I, input; PD, pulldown. Asterisk indicates a non-specific band. b, Wild-type and KEAP1Δ 293T cells were treated with cycloheximide (CHX) for the indicated time and then processed for NRF2 and KEAP1 immunoblotting. Actin levels were also determined as a loading control. c, Immunoprecipitation (IP) of USP11 from extracts prepared from 293T cells that were or were not treated with camptothecin (CPT; 200 nM). Immunoprecipitation with normal IgG was performed as a control. d, U2OS DR-GFP cells were transfected with the indicated siRNAs. Twenty-four hours post-transfection, cells were further transfected with the indicated siRNA-resistant USP11 expression vectors (WT, wild type; CS, C318S and CA, C318A catalytically dead mutants) or an empty vector (EV), with or without an I-SceI expression vector. The percentage of GFP-positive cells was determined 48 h post-plasmid transfection for each condition and was normalized to the I-SceI plus non-targeting (siCTRL) condition (mean±s.d., N=3). e, Schematic representation of human USP11 (top) and KEAP1 (bottom) gene organization and targeting sites of sgRNAs (as described in FIG. 5a) used to generate the USP11Δ and USP11Δ IKEAP1Δ 293T cells. The indels introduced by the CRISPR-Cas9 and their respective frequencies are indicated. The USP11 knockout was created first and subsequently used to make the USP11Δ IKEAP1Δ double mutant. f, Immunoprecipitation of PALB2 from extracts prepared from 293T cells transfected with the indicated siRNA and with or without CPT (200 nM) treatment. Immunoprecipitation with normal IgG was performed as a control.

FIG. 10. USP11 antagonizes KEAP1 action on PALB2. a, U2OS DR-GFP cells were transfected with the indicated siRNAs or left untransfected (−). Twenty-four hours post-transfection, cells were transfected with an I-SceI expression vector (circle). The percentage of GFP-positive cells was determined 48 h post-plasmid transfection for each condition and was normalized to the I-SceI plus non-targeting (CTRL) condition (mean±range, N=3). b, Parental 293T cells (wild type (WT)) or a USP1/Δ derivative were transfected with the indicated GFP-PALB2 constructs, treated with CPT and processed for GFP immunoprecipitation (IP). c, Parental 293T cells (wild type) or a USP11Δ derivative were transfected with an empty vector (EV) or the indicated PALB2 expression vectors. Sensitivity of the cells to the PARP inhibitor olaparib was then determined by a clonogenic survival assay (mean±s.d., N=3).

FIG. 12. Reactivation of RAD51 loading and unscheduled DNA synthesis in G1. a, 53BP1Δ U205 cells were transfected with the indicated siRNA, synchronized in G1 or S/G2 by release from a double-thymidine block and irradiated (20 Gy) before being processed for fluorescence microscopy. DAPI was used to trace the nuclear boundary and cyclin A staining was used to determine cell cycle position. The percentage of cells with more than five γ-H2AX-colocalizing PALB2 foci is indicated as the mean±s.d., N=3. Scale bar, 5 b, Representative micrographs of irradiated G1-synchronized wild-type (WT) and 53BP1Δ U2OS cells transfected with the indicated siRNA and expressing wild-type CtIP. c, Representative micrographs of irradiated G1-synchronized wild-type U2OS cells transfected with the indicated siRNA and expressing CtIP (T847E). d, U2OS 53BP1Δ cells were synchronized in G1, supplemented with BrdU, irradiated (2 Gy) and processed for γ-H2AX and BrdU immunofluorescence. The percentage of cells with more than five γ-H2AX-colocalizing BrdU foci is indicated (mean±s.d., N=3). e, Micrograph of a U2OS cell targeted with the CRISPR-mClover system showing the typical perinuclear expression pattern of lamin A. f, Micrograph of a U2OS cell targeted with the mClover system showing an expression pattern characteristic of subnuclear PML foci. g, Timeline of the gene-targeting (LMNA) experiment presented in FIG. 4d. h, Timeline of the gene targeting (LMNA or PML) experiment presented in FIG. 4e and FIG. 13.

FIG. 13. Analysis of homologous recombination in G1. a, Quantitation of gene targeting efficiency at the LMNA locus in asynchronously dividing U2OS cells transfected with increasing amount of donor template and with (grey) or without (white) sgRNAs. Gene-targeting events were detected by flow cytometry (mean±s.d., N>3). b, Quantitation of gene-targeting efficiency at the LMNA locus in asynchronously dividing cells transfected with the indicated siRNA. Gene-targeting events were detected by flow cytometry (mean±s.d., N=3). c, Gene-targeting efficiency at the PML locus measured by flow cytometry in G1-arrested 53BP1Δ U2OS cells expressing the CtIP(T847E) mutant and co-transfected with the indicated siRNA or a PALB2-KR expression construct (mean±s.d., N=3). d, Gene-targeting efficiency at the LMNA locus measured by flow cytometry in G1-arrested parental (wild-type (WT)) and 53BP1Δ U2OS cells transfected with KEAP1 siRNA and expressing the CtIP(T847E) mutant (mean±s.d., N=3). e, Gene-targeting efficiency at the LMNA locus measured by flow cytometry in G1-arrested parental (wild-type) and 53BP1Δ U2OS cells transfected with the indicated siRNA and expressing either wild type or the CtIP(T847E) mutant (mean±s.d., N=3).

FIG. 14 Identification of DCAF10 as a regulator of USP11 stability in response to DNA damage. a. siRNA screen where U2OS cells were transfected with siRNAs targeting known and predicted DCAFs along with other CUL4-interacting proteins. Cells were either irradiated with IR (20 Gy) or UV (50 J/m-2), let to recover for 3 h and then processed for USP11 immunofluorescence. Each point plotted corresponds to the percentage of USP11 left after irradiation. The red dots correspond to the siRNA non-targeting controls (CTRL) and targeting USP11, whereas the red dots correspond to core CRL4 factors, that include CUL4 itself. b. U2OS cells were transfected with the indicated siRNAs and then irradiated with a dose of 20 Gy and processed for USP11 immunoblotting at the indicated times post-ionizing radiation. Actin was used as a loading control.

FIG. 15. Validation of DCAF10 as a regulator of USP11. a. DCAF10 interacts with USP11. Immunoprecipitation (IP) of Flag-USP11 from extracts prepared from 293 Flp-IN/T-Rex cells. Cells were probed with DCAF10 and DCAF15 antibodies. b. Whole cell extracts of mouse embryo fibroblasts (MEFs) of the indicated genotypes were processed for USP11 immunoblotting. Tubulin was used as a loading control. c. U2OS DR-GFP cells were transfected with the indicated siRNAs or expression vectors. Twenty-four hours post-transfection, cells were transfected with an I-SceI expression vector. The percentage of GFP-positive cells was determined 48 h post-plasmid transfection for each condition and was normalized to the I-SceI plus non-targeting (CTRL)+empty vector (EV) condition.

DETAILED DESCRIPTION OF THE INVENTION

Figure 1A:
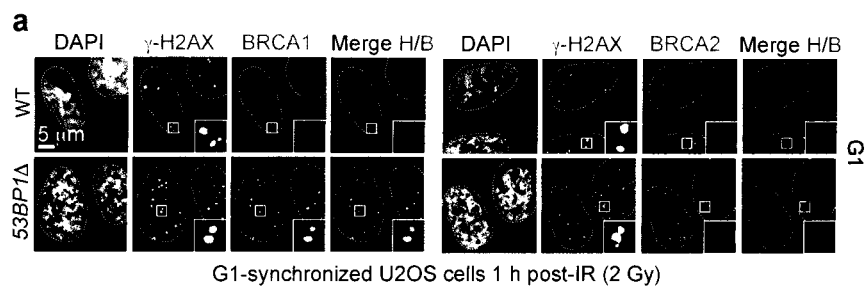
FIG. 1. Inhibition of the BRCA1-PALB2 interaction in G1 is CRL3-KEAP1-dependent. a, Micrographs of irradiated (2 Gy) G1-synchronized U2OS cells processed for γ-H2AX, BRCA1 and BRCA2 immunofluorescence. DAPI, 4',6-diamidino-2-phenylindole; IR, ionizing radiation; WT, wild type. b, Quantitation of the experiment shown in a and FIG. 5d. ASN, asynchronously dividing cells. WT, wild type (Mean±standard deviation (s.d.), N=3). c, Immunoprecipitation (IP) of PALB2 from extracts prepared from mock- or X-irradiated 293T cells synchronized in S or G1 phases. A normal immunoglobulin (Ig)G immunoprecipitation was performed as control. Cyclin A staining ascertains cell cycle synchronization. Numbers on left indicate kDa. For gel source data see FIG. 5. d, Quantitation of the experiment shown in FIG. 7a. 53BP1Δ U2OS cells transfected with the indicated GFP-PALB2 vectors and short interfering (si) RNAs were irradiated (20 Gy) before being processed for microscopy. (mean±s.d., N=3). e, Normal IgG and PALB2 immunoprecipitations from extracts prepared from synchronized and irradiated 293T cells of the indicated genotypes. Numbers on the left indicate kDa.
Figure 1B:
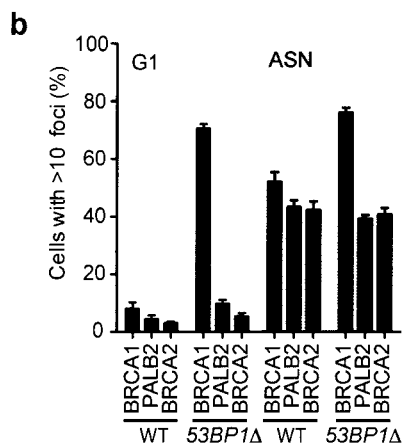

The preparation and use of the agents disclosed as well as the practice of the methods herein employed, unless otherwise indicated, utilize conventional techniques in molecular biology, biochemistry, chromatin structure and analysis, computational chemistry, cell culture, recombinant DNA and related fields as are within the skill of the art. The techniques are fully disclosed in the literature. [See, for example, Sambrook et al. Molecular Cloning: A Laboratory Manual, Second edition, Cold Spring Harbor Laboratory Press, 1989 and Third edition, 2001; Ausubel et al., Current Protocols in Molecular Biology, John Wiley & Sons, New York, 1987 and periodic updates; the series Methods in Enzymology, Academic Press, San Diego; Wolffe, Chromatin Structure and Function, Third edition, Academic Press, San Diego, 1998; Methods in Enzymology, Vol. 304, "Chromatin" (P. M. Wassarman and A. P. Wolffe, eds.), Academic Press, San Diego, 1999; and Methods in Molecular Biology, Vol. 119, "Chromatin Protocols" (P. B. Becker, ed.) Humana Press, Totowa, 1999].

Unless defined otherwise, all technical and scientific terms used herein have the same meaning as commonly understood by one of ordinary skill in the art to which this invention belongs. The following definitions supplement those in the art and are directed to the present application and are not to be imputed to any related or unrelated case. Although any methods and materials similar or equivalent to those described herein can be used in the practice of the invention, particular materials and methods are described herein.

As used herein and in the appended claims, the singular forms "a", "an", and "the" include plural reference unless the context clearly dictates otherwise. As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

A "gene editing system" is a system for targeting and editing genomes, including without limitation, a TALEN (Transcription Activator-Like Effector Nucleases) system, a CRISPR (Clustered Regulatory Interspaced Short Palindromic Repeats) system and a Zinc-Finger Nucleases (ZFN) system. (See Nemudryi A. A. et al, Acta Naturae. 2014 July-September; 6(3): 19-40 for a review of TALEN and CRISPR systems; Gaj T. et al, Trends Biotechnol. 2013 July; 31(7): 397-405 for a review of TALEN, CRISPR and ZFN systems; US Published Patent Application No. 20110145940 describing a TALEN system; and Bibikova M., et al, Genetics. 2002; 161(3):1169-1175; Townsend J. A., et al, Nature 2009; 459(7245):442-445; Zhang F., et al, Proc. Natl. Acad. Sci. USA. 2010; 107(26):12028-12033; Torikai H., et al; Blood. 2012; 119(24):5697-5705; Provasi E., et al, J. Nat. Med. 2012; 18(5):807-8151, and Lombardo A., et al, Nat. Methods. 2011; 8(10):861-869 describing ZFN systems).

A "CRISPR system" generally refers to transcripts and other elements involved in the expression of, or directing the activity of Clustered Regularly Interspaced Short Palindromic Repeats (CRISPR)-associated ("Cas") genes. A CRISPR system may include without limitation, sequences encoding a Cas gene, a tracr (trans-activating CRISPR) sequence (e.g. tracrRNA or an active partial tracrRNA), a tracr-mate sequence, a guide sequence, or other sequences and transcripts from a CRISPR locus. One or more elements of a CRISPR system may be derived from a type I, type II, or type III CRISPR system. A CRISPR system promotes the formation of a CRISPR complex (comprising a guide sequence hybridized to a target sequence and complexed with one or more Cas proteins) at the site of a target sequence. A "target sequence" or "target polynucleotide" refers to a sequence which is sufficiently complementary to a designed guide sequence that the target sequence hybridizes to the guide sequence promoting the formation of a CRISPR complex. A target sequence may comprise any polynucleotide, such as DNA or RNA polynucleotides, and it may be located in the nucleus, cytoplasm, or an organelle, for example, mitochondria or chloroplast. In the context of an endogenous CRISPR system, formation of a CRISPR complex in an endogenous CRISPR system results in cleavage of one or both strands in or near (e.g. within 1, 2, 3, 4, 5, 6, 7, 8, 9, 10, 20, 50, or more base pairs from) the target sequence.

CRISPR systems are described in U.S. Pat. Nos. 8,697,359, 8,771,945, 8,795,965, 8,865,406, 8,871,445, 8,889,356, 8,889,418 and 8,895,308; US Patent Publications US 2014-0310830, US 2014-0287938, US 2014-0273234, U52014-0273232, US 2014-0273231, US 2014-0256046, US 2014-0248702), US 2014-0242700, US 2014-0242699, US 2014-0242664, US 2014-0234972, US 2014-0227787, US 2014-0189896, US 2014-0186958, US 2014-0186919, US 2014-0186843, US 2014-0179770 and US 2014-0179006, US 2014-0170753, and US 20150232883; European Patent Applications EP 2771468 (EP13818570.7), EP 2764103 (EP13824232.6), and EP 2784162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418) and WO2014/093622 (PCT/US2013/074667). General information on CRISPR-Cas Systems is also described in the following publications: Cong, L., et al., Science, February 15; 339 (6121):819-23 (2013); Jiang W., et al, Nat Biotechnol March; 31(3):233-9 (2013); Wang H., et al, Cell May 9; 153(4):910-8 (2013); Konermann S, et al, Nature. 2013 Aug. 22; 500(7463):472-6. doi: 10.1038/Nature12466. Epub 2013 Aug. 23; Ran, F A., et al, Cell August 28. pii: S0092-8674 (13)01015-5. (2013); Hsu, P., et al, Nat Biotechnol doi: 10.1038/nbt.2647 (2013); Ran, F A., et al, Nature Protocols November; 8(11):2281-308. (2013); Shalem, O., et al., Science December 12. (2013). [Epub ahead of print]; Nishimasu, H., et al, Cell February. 27. (2014). 156(5):935-49; Wu X., et al, Nat Biotechnol. (2014) April 20. doi: 10.1038/nbt.2889; Platt et al., Cell 159(2): 440-455 (2014) DOI: 10.1016/j.cell.2014.09.014; Hsu et al. Cell 157, 1262-1278 (Jun. 5, 2014) (2014); Wang et al., Science. 2014 Jan. 3; 343(6166): 80-84. doi: 10.1126/science. 1246981; Doench et al., Nature Biotechnology published online 3 Sep. 2014; doi:10.1038/nbt.3026; Storrs, The Scientist, Article No. 39239, Mar. 1, 2014; and Swiech et al, Nature Biotechnology; published online 19 Oct. 2014; doi:10.1038/nbt.3055). Several programs are available to design guide sequences, for example, MIT's CRISPR Design found at crispr.mit.edu and E-CRISP found at e-crisp.org/E-CRISP developed by the German Cancer Research Center. CRISPR systems also include the systems developed by or available from Editas Medicine (Cambridge, Mass.), Caribou Biosciences (Berkeley, Calif.), CRIPSR Therapeutics (Basel, Switzerland), Addgene (Cambridge, Mass.) and Intellia Therapeutics (Cambridge, Mass.).

"DNA end resection" generally refers to nucleolytic degradation of the 5'-terminated strand of a DNA double-stranded break leading to the formation of 3'-terminated single-stranded DNA. DNA end resection in eukaryotes comprises two phases: a slow initial phase, catalyzed by the Mre11-Rad50-Nbs1 (MRN) complex in mammals, and a second and faster phase catalyzed by the exonuclease Exo1 or the helicase Bloom Syndrome Protein (BLM). DNA end resection is initiated by a cell cycle activation step comprising phosphorylation of the accessory protein CtIP (also known as retinoblastoma binding protein 8). Pathways involved in DNA end resection may be activated by stimulating or activating BRCA1 recruitment to DNA double-strand breaks by inhibiting TP53BP1 (53BP1) or RIF, or blocking recruitment of 53BP1 or RIF to DNA double-stranded break sites. In an aspect, DNA end resection may be activated by inhibiting 53BP1 (or RIF1) expression and/or activity and expressing a mutated form of CtIP that mimics constitutive phosphorylation, for example CtIP-Thr847Glu. In an aspect, DNA end resection is reconstituted or activated using inhibitors of 53BP1 and a mutated form of CtIP that mimics constitutive phosphorylation, in particular CtIP-Thr847Glu. In an aspect, DNA end resection may be reconstituted or activated using purified human proteins: Bloom helicase (BLM); DNA2 helicase/nuclease; Exonuclease 1 (EXO1); the complex comprising MRE11, RAD50, and NBS1 (MRN); and Replication protein A (RPA.) (See Nimonkar A. V. et al, Genes & Development 25:350-362, 2011; Huertas, P, Nat Struct Mol Biol, 17(10: 11-16, doi: 10.1038/nsmb.1710, 2010; Jimeno S., et al, Nucl. Acids Res doe: 101093/nar/gkui384, 2015 for descriptions of DNA end resection).

"Homologous recombination" and "HR" refer to a type of genetic recombination in which DNA strands of similar or identical nucleotide sequences are exchanged. HR can be used by cells to repair DNA double-strand breaks (DSB) by the following general steps. HR is initiated when the DSB is resected by nucleases and helicases, generating 3' single-stranded DNA (ssDNA) overhangs onto which the RAD51 recombinase assembles as a nucleoprotein filament. This structure can invade homologous duplex DNA, which is used as a template for repair DNA synthesis. The resulting intermediates can be metabolized to yield non-crossover products thereby restoring the damaged DNA molecule as it existed before the double-strand break (San Filippo et al., Annu. Rev. Biochem. 2008. 77:229-57). The terms also include recombination using single-stranded donor oligonucleotides (ssODNs), in particular recombination using single-stranded donor oligonucleotides (ssODNs) requiring resection and which may be activated by 53BP1 inhibitors.

"HR Disease" refers to any disorder, disease, condition, syndrome or combination of manifestations or symptoms recognized or diagnosed as a disorder which may be associated with or characterized by a HR defect. Exemplary diseases include, for example, cancer, cardiovascular diseases including heart failure, hypertension and atherosclerosis, respiratory diseases, renal diseases, gastrointestinal diseases including inflammatory bowel diseases such as Crohn's disease and ulcerative colitis, hepatic, gallbladder and bile duct diseases, including hepatitis and cirrhosis, hematologic diseases, metabolic diseases, endocrine and reproductive diseases, including diabetes, bone and bone mineral metabolism diseases, immune system diseases including autoimmune diseases such as rheumatoid arthritis, lupus erythematosus, and other autoimmune diseases, musculoskeletal and connective tissue diseases, including arthritis, achondroplasia infectious diseases and neurological diseases such as Alzheimer's disease, Huntington's disease and Parkinson's disease.

Methods of the invention may be used to monitor or treat a disease caused by a defect in a gene that mediates homologous recombination, for example, BRCA1, BRCA2, PALB2, PARP-1, USP11, RAD51, and/or DCAF10.

Embodiments of the invention provide for monitoring or treatment of various cancers including but not limited to carcinomas, melanomas, lymphomas, sarcomas, blastomas, leukemias, myelomas, osteosarcomas, neural tumors, and cancer of organs such as the breast, ovary, and prostate.

In embodiments, the invention provides for monitoring or treatment of cancer with BRCA-1 defects, BRCA-2 defects, dual BRCA-1/BRCA-2 defects, and Fanconi anemia. In embodiments of the invention, the cancer is breast cancer, in particular invasive ductal carcinoma and invasive lobular carcinoma. In embodiments of the invention, the cancer is ovarian cancer, in particular epithelial ovarian tumors, germ cell ovarian tumors, and sex cord stromal tumors.

Methods of the invention for activating or modulating homologous recombination may be used to genetically modify polynucleotides associated with a genetic disorder. In some embodiments, the genetic disorder is a monogenetic disorder. In some embodiments, the genetic disorder is a multigenetic disorder. In some embodiments, the genetic disorder is associated with one or more SNPs. In particular embodiments of the invention, the genomic modification corrects a point mutation.

Examples of genetic disorders and polynucleotide sequences associated with the genetic disorders may be found on the World Wide Web (see for example, the National Center for Biotechnology Information, National Library of Medicine (Bethesda, Mass.) or the McKusick-Nathans Institute of Genetic Medicine, Johns Hopkins University (Baltimore, Md.)), listed in published patents and applications (see, for example, US Published Application No. 2015/0247150), and in publications (see for example, Turitz Cox D. B. et al, Nature Medicine 21, 121-131, 2015; and O'Connor T. P. and R. G. Crystal, Nature Reviews/Genetics Volume 7, April 2006, pages 261-276 including Supplementary Information, and publications cited therein).

In an aspect, the genetic disorder is a genetic disorder of muscle. In an aspect, the genetic disorder is myotonic dystrophy type 1. In an aspect, the genetic disorder is myotonic dystrophy type 2. In an aspect, the genetic disorder is Duchenne muscular dystrophy (DMD). In an aspect, the genetic disorder is Becker muscular dystrophy.

In an aspect, the genetic disorder is a genetic disorder of the liver, for example, alpha-1 antitrypsin deficiency, Wilson Disease, hereditary hemochromatosis, Type I tyrosinemia, glycogen storage disease Type IV, argininosuccinate lyase deficiency, citrin deficiency, cholesterol ester storage disease and hereditary fructose intolerance.

In an aspect, the genetic disorder is alpha-1 antitrypsin deficiency which is an autosomal recessive (codominant) disease due to mutations in the SERPINA1 gene that encodes the serine protease inhibitor AAT.

In an aspect, the genetic disorder is Wilson disease which depends on mutations in the gene encoding the ATP7B Cu translocase, a protein mainly expressed by the hepatocyte that regulates the levels of copper in the liver.

In an aspect, the genetic disorder is a genetic disorder of the lungs.

In an aspect, the genetic disorder is cystic fibrosis, an autosomal recessive disease caused by mutations of the Cystic Fibrosis Transmembrane Regulator (CFTR) protein, a member of the ATP-binding cassette superfamily of transmembrane proteins.

In other aspects of the invention the genetic disorder may be heamophilia, α1-antitrypsin deficiency, Canavan disease, Adenosine deaminase deficiency, X-linked severe combined immunodeficiency, familial amyloidotic polyneuropathy, thalassemia, Tay-Sachs disease, late infantile ceroid lipofuscinosis, mucopolysaccharidosis, Niemann-Pick disease, achondroplasia, Huntington disease, spino-cerebellar ataxia, Fredriech ataxia, Amyotrophic Lateral Sclerosis, monogenic hypercholesterolemia and other monogenic disorders.

In aspects of the invention the genetic disorder is sickle cell anemia and a method of the invention comprises correcting the mutated HBB hemoglobin gene by gene conversion with its paralog HBD.

An "effective amount" refers to an amount of a compound or composition, as described herein effective to achieve a particular biological result. Such results include, without limitation, the treatment of a disease or condition disclosed herein as determined by any means suitable in the art.

"PARP Inhibitor" refers to an inhibitor of the nuclear enzyme poly(adenosine 5'-diphospho-ribose) polymerase ["poly(ADP-ribose) polymerase" or "PARP", which is also referred to as ADPRT (NAD:protein (ADP-ribosyl transferase (polymerising)) and PARS (poly(ADP-ribose) synthetase). PARP inhibitors have been described in Banasik et al., "Specific Inhibitors of Poly(ADP-Ribose) Synthetase and Mono(ADP-Ribosyl)-Transferase", J. Biol. Chem., 267: 3, 1569-75 (1992), and in Banasik et al., "Inhibitors and Activators of ADP-Ribosylation Reactions", Molec. Cell. Biochem., 138, 185-97 (1994). PARP inhibitors have been disclosed and described in the following patents and patent applications: WO 00/42040; WO 00/39070; WO 00/39104; WO 99/11623; WO 99/11628; WO 99/11622; WO 99/59975; WO 99/11644; WO 99/11945; WO 99/11649; and WO 99/59973; U.S. Pat. Nos. 8,894,989; 8,946,221; 8,778, 966; 8,669,249; 8,623,884; 8,592,416; 8,546,368; 8,541, 417; 8,541,403; 8,420,650; 8,362,030; 8,236,802; 8,217, 070; 8,188,103; 8,188,084; 8,183,250; 8,173,682; 8,129, 382; 8,088,760; 8,080,557; 8,071,623; 8,058,275; 8,012, 976; 8,008,491; 7,999,117; 7,956,064; 7,875,621; 7,820, 668; 7,750,008; 7,732,491; 7,728,026; 7,652,014; 7,601, 719; 7,462,724; 7,087,637; 7,041,675; 6,977,298; 6,924, 284; 6,737,421; 6,635,642; 6,495,541; 6,444,676; 6,395, 749; 6,380,211; 6,380,193; 6,346,536; 6,197,785; 5,756, 510; and Re. 36,397.

In aspects of the invention, the PARP inhibitor is Olaparib (AstraZeneca). In aspects of the invention, the PARP inhibitor is Veliparib (AbbVie Inc, Chicago, Ill.). In aspects of the invention, the PARP inhibitor is Rucaparib (Clovis Oncology, Inc., Boulder, Colo.). In aspects of the invention, the PARP inhibitor is INO-1001 (Inotek Pharmaceuticals Corp, Lexington, Mass.). In aspects of the invention, the PARP inhibitor is MK-4827 (niraparib) (Tesaro, Waltham, Mass., also see Montoni et al, Frontiers in Pharmacology, [4], Article 18, pages 1-7). In aspects of the invention, the PARP inhibitor is talazoparib (Medivation, Inc, San Francisco Calif.).

A "sample" is a sample derived from any biological source, such as tissues, extracts, or cell cultures, including cells (e.g. tumor cells), cell lines, cell lysates, and physiological fluids, such as, for example, blood or subpopulations thereof (e.g. white blood cells, erythrocytes), plasma, serum, saliva, ocular lens fluid, cerebrospinal fluid, sweat, urine, fecal matter, tears, bronchial lavage, swabbings, milk, ascites fluid, nipple aspirate, needle aspirate, synovial fluid, peritoneal fluid, lavage fluid, and the like. The sample can be obtained from animals, preferably mammals, most preferably humans. Samples can be from a single individual or pooled prior to analysis. The sample can be treated prior to use, such as preparing plasma from blood, diluting viscous fluids, and the like. Methods of treating samples can involve filtration, distillation, extraction, centrifugation, concentration, inactivation of interfering components, the addition of reagents, and the like.

In embodiments of methods of the invention, the sample is a mammalian tissue sample. In another embodiment the sample is a cell lysate. In another embodiment the sample is a cell. In another embodiment the sample is a human physiological fluid. In a particular embodiment, the sample is human serum. In a further embodiment, the sample is white blood cells or erythrocytes.

The terms "subject", "individual" or "patient" refer, interchangeably, to a warm-blooded animal such as a mammal. In particular, the terms refer to a human. A subject, individual or patient may be afflicted with or suspected of having or being pre-disposed to a disease as described herein. The term also includes animals bred for food, as pets, or for study including horses, cows, sheep, poultry, fish, pigs, cats, dogs, and zoo animals goats, apes (e.g. gorilla or chimpanzee), and rodents such as rats and mice.

NCBI Accession Numbers for USP11, PALB2, BRCA1, BRCA2, KEAP1, 53BP1, DCAF10, RBX1, CUL3 and CtIP are in Table 1 and the human sequences for same are in the Sequence Listing.

Screening and Monitoring Assays

The invention provides a method for monitoring activity or expression of USP11 by assaying the interaction of BRCA1 and PALB2, the interaction of BRCA1, PALB2 and BRCA2, the interaction of USP11 and DCAF10, and/or the interaction of USP11 and PALB2. Routine methods known to persons skilled in the art can be used to assay protein interactions in a sample. For example, BRCA1-PALB2, BRCA1-PALB2-BRCA2, USP11-DCAF10, or USP11-PALB2 complexes may be isolated using affinity techniques such as for example immunologically-based purification (e.g. immunoaffinity chromatography), peptides may be prepared from the isolated complexes using conventional methods (e.g. gel electrophoresis, liquid chromatography, capillary electrophoresis, nano-reversed phase liquid chromatography, high performance liquid chromatography, or reverse phase high performance liquid chromatography), and the peptides or peptide fragments may be subjected to mass spectrometry (e.g., quantitative mass spectrometry such as selected reaction monitoring mass spectrometry (sMRM), high resolution data independent analyses (SWATH), high resolution multiple reaction monitoring (MRM$^{HR}$) or MS1 based quantitation).

The invention also provides a method for monitoring activity of USP11 by assaying ubiquitylation of the N-terminus of PALB2. Routine methods known to persons skilled in the art can be used to assay ubiquitination in a sample. For example, ubiquitination or PALB2 may be assayed by measuring changes in PALB2 (e.g., weight; see U.S. Pat. No. 6,413,725), the amount of poly-ubiquitin bound to CRL3-KEAP1 E3 ligase (see for example, EP 1268847), and/or the activity of CRL3-KEAP1 E3 ligase (see for example, US Publication No. 2013/0116152). Mass spectrometry techniques such as selected reaction monitoring mass spectrometry (sMRM), high resolution data independent analyses (SWATH), high resolution multiple reaction monitoring (MRM$^{HR}$) or MS1 based quantitation) can also be used to monitor ubiquitin remnants on peptides from the PALB2 N-terminus following protease digestion. In a more specific example, preparation of isotopically labeled synthetic peptides corresponding to tryptic digests of ubiquitylated PALB2, especially those that correspond to ubiquitylation on Lys14, Ly16, Lys20, Lys25, Lys30, Lys43 or Lys45 can be used as internal standards to quantitate the extent of PALB2 ubiquitylation.

In an aspect, the invention provides a method for assaying ubiquitylation of PALB2 polypeptides in a sample, the method comprising digesting ubiquitinated PALB2 polypeptides in the sample with a protease, thereby generating a plurality of test peptides; determining the presence of at least one isopeptide bond between ubiquitin and a lysine residue of the test peptides by mass spectrometry to determine the numbers of ubiquitination sites and thereby the amount of ubiquitination of PALB2 polypeptides in the sample. In an embodiment, the test peptides are from the PALB2 N-terminus. In an embodiment, the lysine residue corresponds to Lys14, Lys16, Lys20, Lys25, Lys30, Lys43 or Lys45. The method may utilize peptide internal standards corresponding to different peptide subsequences of PALB2 to provide for controls in a quantitative assay. In one aspect, different synthetic peptide internal standards corresponding to PALB2 are generated and differentially labeled.

Proximity ligation assays (PLA) may also be used to assay activity of USP11 by assaying the interaction between BRCA1 and PALB2 and/or PALB2-interacting proteins such as BRCA2, using DNA-based detection. For example, primary antibodies against binding partners of an interaction (e.g., PALB2 and BRCA1) are added to a cell lysate. A second set of antibodies, termed PLA probes or proximity probes, recognize the first set of primary antibodies. The PLA probes contain DNA strands that assemble into an assay-specific DNA molecule when in close proximity. This DNA molecule can then be amplified and detected using, for example, fluorescent probes. [See, for example, Soderberg O. et al., Nat. Methods., 2006 December; 3(12):995-1000; Jarvius M. et al., Mol. Cell. Proteomics, 2007 September; 6(9):1500-9)].

In an aspect, the invention provides a method for assaying BRCA1-PALB2 or BRCA1-PALB2-BRCA2 interactions in a sample comprising: contacting the sample with primary antibodies to each binding partner in the interaction; contacting the sample with proximity probes comprising a secondary antibody that binds to a corresponding primary antibody, wherein each proximity probe has an oligonucleotide conjugated thereto; wherein when the oligonucleotides of the proximity probes are in sufficient proximity to each other, the oligonucleotides of the proximity probes interact to form circular products that are amplified by rolling circle replication producing amplification products; and, measuring the amplification products to thereby assay or measure the interactions.

Assays that monitor PALB2 (or associated proteins such as BRCA2) in situ co-localization with BRCA1 can also provide a method for monitoring USP11 activity (see Example herein). For example, PALB2 localization at sites of DNA damage (marked by BRCA1 or other markers such as γ-H2AX) is dependent on USP11 activity. In such assays, cells are fixed, permeabilized and then incubated with antibodies that detect PALB2, BRCA2 or their associated proteins (e.g., BRCA1). Addition of labeled secondary antibodies enable the in situ visualization of protein accumulation at DNA damage sites in subnuclear structures termed foci. Addition of a genotoxic insult (such as ionizing radiation or other clastogenic treatments) increases the number of "foci" and can be included to augment the dynamic range of the assay.

It will be appreciated that proximity ligation assays and in situ co-localization assays may be used to assay any of the interactions disclosed herein.

The methods of the invention may be performed in the presence or absence of a test compound or agent and detection of an increase or decrease in activity or expression of one or more of USP11, DCAF10, PALB2, PALB2 ubiquitylation, BRCA1-PALB2-BRCA2 complex, PALB2-USP11 complex, KEAP1, USP11-DCAF10 complex, CRL3-KEAP1 complex, CRL3-KEAP1-PALB2 complex, and KEAP1-PALB2 complex, as compared to a control in the absence of the test compound or agent indicates that the test compound or agent may be useful as a therapeutic agent, or for modulating homologous recombination.

In an aspect, the invention provides a method for identifying or evaluating an agent for its ability to sensitize or reverse or delay emergence of resistance to PARP inhibitors by determining the effect of the agent on USP11 activity using a method of the invention. In an aspect, a negative effect on USP11 indicates that the agent is a sensitizer of cells to PARP inhibitors or can reverse or delay emergence of resistance to PARP inhibitors. In an aspect, a positive effect on USP11 indicates that the agent is a poor sensitizer of cells to PARP inhibitors. In an aspect, the ability of an agent to sensitize or reverse or delay emergence of resistance to PARP inhibitors is determined by decreased levels of USP11 activity when compared to such levels obtained from a control. In an aspect, the ability of an agent to sensitize or reverse or delay emergence of resistance to PARP inhibitors is determined by increased levels of USP11 activity when compared to such levels obtained from a control.

The invention also relates to a method of identifying or evaluating an agent for its ability to sensitize cells to reverse or delay emergence of resistance to PARP inhibitors by determining the effect of the agent on KEAP1, CRL3-KEAP1, or KEAP1-PALB2. In an aspect, a negative effect on KEAP1 (loss of KEAP1 or CRL3-KEAP1 activity) indicates that the agent is a poor sensitizer of cells to PARP inhibitors. In an aspect, a positive effect on KEAP1 or CRL3-KEAP1 activity indicates that the agent is a sensitizer of cells to PARP inhibitors or can reverse or delay emergence of resistance to PARP inhibitors. In an aspect, the ability of an agent to sensitize or reverse or delay emergence of resistance to PARP inhibitors is determined by increased levels of KEAP1, CRL3-KEAP1, KEAP1-PALB2 or CRL3-KEAP1 activity or expression when compared to such levels obtained from a control. In an aspect, the ability of an agent to sensitize or reverse or delay emergence of resistance to PARP inhibitors is determined by decreased levels of KEAP1, CRL3-KEAP1, KEAP1-PALB2 or CRL3-KEAP1 activity or expression when compared to such levels obtained from a control.

Still further the present invention contemplates methods of detecting an anti-cancer agent comprising performing a test assay comprising contacting an immortalized cell with a test compound and measuring USP11 activity or CRL3-KEAP1 using a method of the invention and comparing to a control test assay in the absence of the test compound. In an aspect, USP11 activity is assayed by measuring USP11, PALB2, DCAF10, PALB2 ubiquitylation, BRCA1-PALB2-BRCA2 complex, PALB2-USP11 complex, KEAP1, USP11-DCAF10 complex, CRL3-KEAP1 and/or CRL3-KEAP1-PALB2 complex in the cell. In an aspect, detecting a negative effect of the agent on USP11 activity or expression as compared with a control indicates a potential anti-cancer agent or PARP inhibitor sensitizer. In an aspect, detecting a negative effect of the agent on BRCA1-PALB2-BRCA2 complex and/or PALB2-USP11 complex activity or expression as compared with a control indicates a potential anti-cancer agent or PARP inhibitor sensitizer. In an aspect, detecting a positive effect of the agent on KEAP1, CRL3-KEAP1 and/or CRL3-KEAP1-PALB2 complex activity or expression as compared with a control indicates a potential anti-cancer agent or PARP inhibitor sensitizer. In an aspect, decreased levels of USP11 activity when compared to such levels obtained from a control are indicative that agent has anti-cancer activity or is a PARP inhibitor sensitizer.

The invention provides a method for identifying or evaluating an agent for its ability to modulate homologous recombination comprising determining the effect of a test compound or agent on one or more of USP11, DCAF10, PALB2, PALB2 ubiquitylation, BRCA1-PALB2-BRCA2 complex, PALB2-USP11 complex, KEAP1, USP11-DCAF10 complex, CRL3-KEAP1 complex and CRL3-KEAP1-PALB2 complex. In an aspect, the invention provides a method for identifying or evaluating an agent for its ability to modulate homologous recombination in a cell comprising (i) assaying in a sample USP11, DCAF10, PALB2, PALB2 ubiquitylation, BRCA1-PALB2-BRCA2 complex, PALB2-USP11 complex, KEAP1, USP11-DCAF10 complex, CRL3-KEAP1 and/or CRL3-KEAP1-PALB2 complex in the cell in the presence or absence of the agent, and (ii) detecting an increase or decrease in USP11, DCAF10, PALB2, PALB2 ubiquitylation, BRCA1-PALB2-BRCA2 complex, PALB2-USP11 complex, KEAP1, USP11-DCAF10 complex, CRL3-KEAP1 complex and/or CRL3-KEAP1-PALB2 complex in the sample compared to a control as an indication of the ability of the agent to modulate homologous recombination.

The invention provides a method of screening for a therapeutic agent for treatment of a disease associated with defects in HR (i.e., HR Disease), comprising identifying an agent that disrupts or modulates one or more of USP11, PALB2, PALB2 ubiquitylation, DCAF10, BRCA1-PALB2-BRCA2 complex, PALB2-USP11 complex, KEAP1, USP11-DCAF10 complex, CRL3-KEAP1 or CRL3-KEAP1-PALB2 complex. In an aspect, detecting a positive effect of the agent on USP11, BRCA1-PALB2-BRCA2 complex and/or, PALB2-USP11 complex activity or expression as compared with a control indicates a potential therapeutic agent for treatment of a HR Disease. In an aspect, detecting a negative effect of the agent on, DCFA10, KEAP1, CRL3-KEAP1 or CRL3-KEAP1-PALB2 complex activity or expression as compared with a control indicates a potential therapeutic agent for treatment of a HR Disease.

Test compounds used in the methods of the invention can be any product in isolated form or in a mixture. The test compound may be defined by structure or function or it may be undefined. Examples of undefined test compounds include without limitation tissue samples, biological fluids, cell supernatants, vegetal preparations; etc. Test compounds may be peptides such as soluble peptides including Ig-tailed fusion peptides, members of random peptide libraries and combinatorial chemistry-derived molecular libraries made of D- and/or L-configuration amino acids, carbohydrates, nucleic acids, antisense molecules, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], small organic or inorganic molecules, or libraries of compounds. A test compound may be an endogenous physiological compound or natural or synthetic compounds.

In embodiments, the methods of the invention for identifying agents, in particular anti-cancer agents, comprise contacting more than one test compound, in parallel. In some embodiments, the methods comprises contacting 2, 3, 4, 5, 6, 7, 8, 9, 10, 15, 20, 25, 30, 40, 50, 100, 1000, at least 2, at least 5, at least 10, at least 50, at least 100, or at least 1000 test compounds in parallel. In some embodiments, high throughput screening of compounds and complete combinatorial libraries are assayed. Methods for performing high throughput screens are well known in the art. The methods can also be automated such that a robot can perform the experiments.

In embodiments, the methods of the present invention for identifying agents, in particular anti-cancer agents, comprises the step of contacting a cell in the presence of a test compound. The cells can then be observed to determine if the test compound(s) effects USP11 activity, DCAF10, PALB2, ubiquitination of PALB2, KEAP1, CRL-KEAP1 activity, the interaction of BRCA1 and PALB2, the interaction of USP11 and PALB2, the interaction of USP11 and DCAF10, and/or the interaction of BRCA1, PALB2 and BRCA2. Positive and negative controls may be performed in which known amounts of test compound and no compound, respectively, are added to the assay. One skilled in the art can select and perform the appropriate controls.

The activity of a test compound(s) may be unknown, and the methods of the invention may be used to identify compounds exhibiting the selected property (e.g., PARP inhibitor sensitizer). In some embodiments, the activity or type of activity of the test compound(s) is known or expected, and the methods of the invention can be used to further characterize or optimize the activity (e.g., specificity, efficacy, etc).

A method of the invention may also comprise assaying PARP activity in the presence of the test compound. PARP activity may be assayed by measuring a change of poly (ADP-ribose) polymers (PAR), and measuring NAD levels and/or ATP levels using methods routine to one of ordinary skill in the art. In some embodiments, the levels of NAD are depleted in the presence of the test compound. In some embodiments the levels of ATP are depleted in the presence of the test compound. In some embodiments, the levels of NAD are increased in the presence of the test compound. In some embodiments the levels of ATP are increased in the presence of the test compound.

A method of the invention may comprise the step of determining if a cell has undergone necrosis following administration of a test compound. The physical characteristics of the cell can be analyzed using routine methods known to those skilled in the art to determine if a cell has undergone necrosis. For example, necrosis may be determined by measuring organelle swelling, plasma membrane disintegration, intracellular vacuole formation, and nuclear degradation without condensation.

The screening methods of the invention may further comprise conducting therapeutic profiling of the identified agents or further analogs thereof, for efficacy and toxicity in animals; optionally formulating a pharmaceutical composition including one or more agents identified as having an acceptable therapeutic profile; and optionally administering the agent to a subject or individual.

In an aspect, the therapeutic activity of agents and compositions identified using a method of the invention may be evaluated in vivo using a suitable animal model. Thus, the screening methods of the invention may further comprise conducting in vivo studies comprising administering the agent to a suitable animal model.

The invention also provides a method of predicting a response or categorizing a response to a PARP inhibitor in a subject comprising assaying one or more of USP11, DCAF10, BRCA1, BRCA2, PALB2, KEAP1, CRL3, CRL3-KEAP1, BRCA1-PALB2-BRCA2 complex, PALB2-USP11 complex and CRL3-KEAP1-PALB2 complex or PALB2 ubiquitylation in a sample from the subject using a method of the invention. Significantly different levels of one or more of USP11, DCAF10, BRCA1, BRCA2, PALB2, KEAP1, CRL3, CRL3-KEAP1, BRCA1-PALB2-BRCA2 complex, PALB2-USP11 complex and CRL3-KEAP1-PALB2 complex or PALB2 ubiquitylation compared to a control indicate responsiveness (e.g., sensitivity) to the PARP inhibitor.

In an aspect, the invention provides a method of predicting a response or categorizing a response to a PARP inhibitor in a subject comprising detecting USP11, BRCA1, BRCA2, PALB2 and KEAP1 in a sample from the subject using a method of the invention. In an embodiment, significantly different levels of USP11, BRCA1, BRCA2, PALB2 and KEAP1 compared to a control indicate responsiveness (e.g., sensitivity) to the PARP inhibitor.

In an aspect, the invention provides a method of predicting a response or categorizing a response to a PARP inhibitor in a subject comprising detecting USP11, DCAF10, BRCA1, BRCA2, PALB, KEAP1 and CRL3 in a sample from the subject using a method of the invention. In an embodiment, significantly different levels of USP11, DCAF10, BRCA1, BRCA2, PALB, KEAP1 and CRL3 compared to a control indicate responsiveness (e.g., sensitivity) to the PARP inhibitor.

In an aspect, a subject is categorized as responsive to a PARP inhibitor if there is a decrease in one or more of USP11, DCAF10, BRCA1, BRCA2, PALB2, KEAP1, CRL3, CRL3-KEAP1, BRCA1-PALB2 and BRCA1-PALB2-BRCA2 activity or expression or PALB2 ubiquitylation compared to a control. In an aspect, a subject is categorized as responsive to a PARP inhibitor if there is an increase in one or more of USP11, DCAF10, BRCA1, BRCA2, PALB2, KEAP1, CRL3, CRL3-KEAP1, BRCA1-PALB2 and BRCA1-PALB2-BRCA2 activity or expression or PALB2 ubiquitylation compared to a control. In an embodiment, significantly different levels (e.g., lower levels) of USP11 activity compared to a control indicate sensitivity to the PARP inhibitor.

In an aspect, the invention provides a method of predicting a response or categorizing a response to a PARP inhibitor in a subject comprising detecting one or more of USP11, DCAF10, BRCA1, BRCA2, PALB2, KEAP1, CRL3 and CRL3-KEAP1 activity or expression or PALB2 ubiquitylation in a sample from the subject and comparing to a control to determine if the subject will be responsive (e.g., sensitive) to the PARP inhibitor.

In an aspect, the invention provides a method of predicting a response or categorizing a response to a PARP inhibitor in a subject comprising detecting USP11, BRCA1, BRCA2, PALB2 and KEAP1 activity or expression in a sample from the subject and comparing to a control to determine if the subject will be responsive (e.g., sensitive) to the PARP inhibitor.

In an aspect, the invention provides a method of predicting a response or categorizing a response to a PARP inhibitor in a subject comprising detecting USP11, DCAF10, BRCA1, BRCA2, PALB2, KEAP1 and CRL3 activity in a sample from the subject and comparing to a control to determine if the subject will be responsive (e.g., sensitive) to the PARP inhibitor.

In an aspect, the invention provides a method of predicting a response or categorizing a response to a PARP inhibitor in an individual comprising assaying USP11 activity or expression in a sample from the individual using a method of the invention. In an embodiment, significantly different levels (e.g., lower levels) of USP11 activity or expression compared to a control indicate sensitivity to the PARP inhibitor.

In an aspect, the invention provides a method of predicting a response or categorizing a response to a PARP inhibitor in an individual comprising detecting KEAP1 in a sample from the individual and comparing to a control to determine if the individual will be sensitive to a PARP inhibitor. In an embodiment, significantly different levels (e.g., higher levels) of KEAP1 compared to a control indicate sensitivity to the PARP inhibitor.

The invention also provides a method of predicting a response or categorizing a response to a PARP inhibitor in an individual comprising detecting CRL3-KEAP1 activity in a sample from the individual and comparing to a control to determine if the individual will be sensitive to a PARP inhibitor. In an embodiment, significantly different levels (e.g., higher levels) of CRL3-KEAP1 compared to a control indicate sensitivity to the PARP inhibitor.

The invention also provides a method of predicting a response or categorizing a response to a PARP inhibitor in an individual comprising detecting PALB2 ubiquitylation in a sample from the individual and comparing to a control to determine if the individual will be sensitive to a PARP inhibitor. In an embodiment, significantly different levels of PALB2 ubiquitylation compared to a control indicate sensitivity to the PARP inhibitor.

The invention also provides a method of predicting a response or categorizing a response to a PARP inhibitor in an individual comprising detecting complexes of BRCA1, PALB2 and BRCA2 in a sample from the subject and comparing to a control to determine if the individual will be responsive (e.g., sensitive) to a PARP inhibitor. In an embodiment, significantly different levels (e.g., absence or low levels) of complexes of BRCA1, PALB2 and BRCA2 indicate sensitivity to the PARP inhibitor.

The invention further provides a method for assigning an individual to one of a plurality of categories in a clinical trial for a PARP inhibitor comprising assaying USP11, DCAF10, PALB2, PALB2 ubiquitylation, BRCA1-PALB2-BRCA2 complex, PALB2-USP11 complex, USP11-DCAF10 complex, KEAP1, CRL3-KEAP1 or CRL3-KEAP1-PALB2 complex in a sample from the individual using a method of the invention.

The invention further provides a method for assigning an individual to one of a plurality of categories in a clinical trial for a PARP inhibitor comprising assaying USP11 activity in a sample from the individual using a method of the invention.

The invention further provides a method for assigning an individual to one of a plurality of categories in a clinical trial for a PARP inhibitor comprising assaying CRL3-KEAP activity in a sample from the individual.

The invention further provides a method for assigning an individual to one of a plurality of categories in a clinical trial for a PARP inhibitor comprising detecting or quantitating USP11, BRCA1, BRCA2, PALB2 and KEAP1 in a sample from the individual.

The invention further provides a method for assigning an individual to one of a plurality of categories in a clinical trial for a PARP inhibitor comprising detecting or quantitating USP11, DCAF10, BRCA1, BRCA2, PALB2 and KEAP1 in a sample from the individual.

The invention further provides a method for assigning an individual to one of a plurality of categories in a clinical trial for a PARP inhibitor comprising detecting or quantitating BRCA1-PALB2-BRCA2 complex in a sample from the individual.

The invention further provides a method for assigning an individual to one of a plurality of categories in a clinical trial for a PARP inhibitor comprising detecting or quantitating PALB2 ubiquitylation in a sample from the individual.

In an aspect, an individual is assigned to a category for a clinical trial for a PARP inhibitor based on a decrease in one or more of USP11, DCAF10, BRCA1, BRCA2, PALB2, KEAP1, CRL3, CRL3-KEAP1, BRCA1-PALB2 and BRCA1-PALB2-BRCA2 activity or expression or PALB2 ubiquitylation compared to a control. In an aspect, an individual is assigned to a category for a clinical trial for a PARP inhibitor based on an increase in one or more of USP11, DCAF10, BRCA1, BRCA2, PALB2, KEAP1, CRL3, CRL3-KEAP1, BRCA1-PALB2 and BRCA1-PALB2-BRCA2 activity or expression or PALB2 ubiquitylation compared to a control.

A variety of routine methods known to a person skilled in the art can be employed for detecting or assaying the biomarkers USP11, DCAF10, BRCA1, BRCA2, PALB2, KEAP1, CRL3 and/or complexes thereof in a sample. Biomarker levels present in a sample may be determined by any suitable assay, which may comprise the use of any of the group comprising or consisting of immunoassays, spectrometry, mass spectrometry, Matrix Assisted Laser Desorption/Ionization Time-of-Flight (MALDI-TOF) Mass Spectrometry, microscopy, northern blot, isoelectric focusing, SDS-PAGE, PCR, quantitative RT-PCR, gel electrophoresis, DNA microarray, and antibody microarray, or combinations thereof.

The invention also provides a system comprising: an assay for determining the level of USP11 activity, complexes or biomarker levels in a sample obtained from the subject; a processor for processing the results; computer coded instructions for comparing the results with a database; and a user display for providing the results of the comparison. The database may comprise reference values for USP11 activity or biomarker levels.

Treatment Methods

A method of the invention for predicting or characterizing responsiveness to a PARP inhibitor may further comprise administering the PARP inhibitor to the individual or subject. In an aspect, the invention relates to a method of treating a subject with a PARP inhibitor comprising:
 a) assaying a sample from the subject for responsiveness or sensitivity to one or more PARP inhibitors using a method of the invention;
 b) identifying a PARP inhibitor that the subject effectively responds or is sensitive to; and
 c) administering the PARP inhibitor to the subject.

In an aspect, the invention provides a method for treating a patient in need of treatment with a PARP inhibitor comprising (a) requesting a test providing the results of an analysis to determine if the patient is sensitive to the PARP inhibitor by detecting USP11, DCAF10, BRCA1, BRCA2, PALB2, KEAP1 and/or CRL3 in a sample from the subject and comparing to a control to determine if the patient is sensitive to the PARP inhibitor; and (b) administering the PARP inhibitor to the patient if the patient is sensitive to the PARP inhibitor. In an aspect of this method of the invention, the patient has breast cancer. In an aspect of this method of the invention, the patient has ovarian cancer. In an aspect of the invention, the test detects USP11 expression or activity using a method disclosed herein.

The invention further provides a method for treating cancer in a subject the method comprising: (i) selecting a subject who is responsive to a PARP inhibitor using a method of the invention, and (ii) administering to said subject the PARP inhibitor in an effective amount to treat the cancer. In an embodiment, the cancer is breast cancer. In an embodiment, the cancer is ovarian cancer.

Agents identified using the methods of the present invention have numerous therapeutic applications related to, for example, cancer, ischemia reperfusion injury, inflammatory diseases, degenerative diseases, protection from adverse effects of cytotoxic compounds, and potentiation of cytotoxic cancer therapy. Agents identified using the methods of the invention may be used to potentiate radiation and chemotherapy by increasing apoptosis of cancer cells, limiting tumor growth, decreasing metastasis, and prolonging the survival of tumor-bearing subjects. In aspects of the invention, the agents can be used to treat leukemia, colon cancer, glioblastomas, lymphomas, melanomas, carcinomas of the breast, ovarian cancer and cervical carcinomas.

In other aspects of the invention, the agents can be used to treat, without limitation, retroviral infection, arthritis, gout, inflammatory bowel disease, CNS inflammation, multiple sclerosis, allergic encephalitis, sepsis, septic shock, hemorrhagic shock, pulmonary fibrosis, uveitis, diabetes, Parkinson's disease, myocardial infarction, stroke, other neural trauma, organ transplantation, reperfusion of the eye, reperfusion of the kidney, reperfusion of the gut, reperfusion of skeletal muscle, liver toxicity following acetaminophen overdose, cardiac and kidney toxicities from doxorubicin and platinum based antineoplastic agents, and skin damage secondary to sulfur mustards.

In some embodiments, the invention provides a method for sensitizing an individual to treatment with PARP inhibitors comprising identifying an agent that sensitizes cells to PARP inhibitors in accordance with a method of the invention and administering the agent to the individual.

In some embodiments, the invention provides a method for treating an individual being treated with a PARP inhibitor comprising administering to the individual an agent that sensitizes cells to the PARP inhibitor identified using a method of the invention.

In some embodiments, the invention provides a method for reversing or delaying emergence of resistance to PARP inhibitors in an individual comprising identifying an agent that reverses or delays emergence of resistance to PARP inhibitors in accordance with a method of the invention and administering the agent to the individual.

In some embodiments, the present invention provides methods of treating cancer in an individual comprising identifying an anti-cancer agent in accordance with a method of the invention and administering the agent to the individual.

In another embodiment, the present invention provides a method of treating leukemia, colon cancer, glioblastomas, lymphomas, melanomas, carcinomas of the breast, ovarian cancer or cervical carcinomas in a mammal in need of such treatment comprising administering to the mammal a therapeutically acceptable amount of an agent identified using a method of the invention or a therapeutically acceptable salt thereof.

In another embodiment, the present invention provides a method of potentiation of cytotoxic cancer therapy in a mammal in need of such treatment comprising administering to the mammal a therapeutically acceptable amount of an agent identified using a method of the invention that potentiates cytotoxic cancer therapy or a therapeutically acceptable salt thereof.

In an aspect, the invention provides methods of treating a disease associated with defects in HR (i.e., HR Disease) in an individual comprising identifying an agent that modulates HR in accordance with a method of the invention and administering the agent to the individual.

In another embodiment, the present invention provides a use of an agent identified using a method of the invention to prepare a medicament for treating a HR Disease in a mammal in need of such treatment. In another embodiment, the present invention provides a use of an agent identified using a method of the invention, to prepare a medicament for inhibiting tumor growth in a mammal in need of such treatment. In another embodiment, the present invention provides a use of an agent identified using a method of the invention to prepare a medicament for treating cancer in a mammal in need of such treatment. In another embodiment, the present invention provides a use of an agent identified using a method of the invention to prepare a medicament for treating leukemia, colon cancer, glioblastomas, lymphomas, melanomas, carcinomas of the breast, ovarian cancer or cervical carcinomas in a mammal in need of such treatment. In another embodiment, the present invention provides a use of an agent identified using a method of the invention to prepare a medicament for potentiation of cytotoxic cancer therapy in a mammal in need of such treatment comprising administering to the mammal a therapeutically acceptable amount of the agent.

In an embodiment, the present invention provides a pharmaceutical composition comprising an agent identified using a method of the invention, or a therapeutically acceptable salt thereof, in combination with a therapeutically acceptable carrier. Pharmaceutical compositions can be prepared by per se known methods for the preparation of pharmaceutically acceptable compositions which can be administered to subjects, such that an effective quantity of the active substance is combined in a mixture with a pharmaceutically acceptable vehicle. Suitable carriers are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the active agents in association with one or more pharmaceutically acceptable vehicles or diluents, and contained in buffered solutions with a suitable pH and iso-osmotic with the physiological fluids.

The pharmaceutical compositions are indicated as therapeutic agents either alone or in conjunction with other therapeutic agents or other forms of treatment. The compositions of the invention may be administered concurrently, separately, or sequentially with other therapeutic agents or therapies, for example PARP inhibitors.

Homologous Recombination Methods

The invention provides a method for activating or modulating homologous recombination in a cell comprising:

(a) promoting or stimulating the assembly or occurrence of BRCA1-PALB2 or BRCA1-PALB2-BRCA2 complexes in the cell;

(b) promoting or stimulating BRCA1 recruitment to DNA double-strand break (DSB) sites;

(c) contacting the cell with BRCA1-PALB2 or BRCA1-PALB2-BRCA2 complexes;

(d) inhibiting KEAP1 or CRL3-KEAP1;

(e) inhibiting the degradation of USP11 or promoting USP11 activity; and/or (f) inhibiting DCAF10.

In an aspect the cell is in the G1 phase of the cell cycle (G1). In an aspect the cell is a non-dividing cell or a dormant cell in G1. In an aspect, the cell is in the G0 phase of the cell cycle (G0). In an aspect, the methods of the invention are used in vitro to activate or modulate homologous recombination in cells.

In an aspect, the invention provides a method for activating or modulating homologous recombination in a cell, in particular a cell in the G1 phase of the cell cycle (G1) or G0 phase of the cell cycle (G0), comprising (a) promoting or stimulating the assembly or occurrence of BRCA1-PALB2 or BRCA1-PALB2-BRCA2 complexes in the cell; and/or (b) contacting the cell with BRCA1-PALB2 or BRCA1-PALB2-BRCA2 complexes.

In embodiments, the assembly of BRCA1-PALB2 or BRCA1-PALB2-BRCA2 complexes is promoted or stimulated by administering an agent that promotes or stimulates BRCA1-PALB2 or BRCA1-PALB2-BRCA2 complexes identified using a method of the invention.

In an aspect, the invention provides a method for activating or modulating homologous recombination in a cell, in particular a cell in G1 or G0, comprising the step of inhibiting KEAP1 or CRL3-KEAP1. In an aspect, the invention provides a method for activating or modulating homologous recombination in a cell, in particular a cell in G1 or G0, comprising the step of blocking the degradation of USP11 or promoting USP11 activity. In an embodiment, the method comprises administering USP11 or an agonist thereof. In an aspect, the invention provides a method for activating homologous recombination in a cell, in particular a cell in G1 or G0, comprising the step of inhibiting KEAP1 and blocking the degradation of USP11. In an aspect, the invention provides a method for activating homologous recombination in a cell, in particular a cell in G1 or G0, comprising the step of inhibiting CRL3-KEAP1 and blocking the degradation of USP11. In an aspect, the invention provides a method for activating homologous recombination in a cell, in particular a cell in G1 or G0, comprising the step of inhibiting CRL3 and blocking the degradation of USP11.

Methods of the invention may be performed in a cell, in particular a cell in the G1 phase of the cell cycle (G1) or G0 phase of the cell cycle (G0) in which DNA end resection is or has been activated generating single-stranded DNA.

The invention provides a method for activating or modulating homologous recombination in a cell, in particular a cell in the G1 phase of the cell cycle (G1) or G0 phase of the cell cycle (G0) in which DNA end resection is or has been activated generating single-stranded DNA, comprising promoting or stimulating the assembly or occurrence of BRCA1-PALB2 or BRCA1-PALB2-BRCA2 complexes in the cell. In an embodiment, the assembly of the complexes is promoted or stimulated by administering an agent that promotes or stimulates assembly or occurrence of BRCA1-PALB2 or BRCA1-PALB2-BRCA2 complexes identified using a method of the invention.

The invention also provides a method for repairing DNA double-strand breaks in a cell in the G1 phase of the cell cycle (G1) or G0 phase of the cell cycle (G0), comprising promoting or stimulating the assembly or occurrence of BRCA1-PALB2 or BRCA1-PALB2-BRCA2 complexes in the cell.

The invention also provides a method for repairing DNA double-strand breaks in a cell in the G1 phase of the cell cycle (G1) or G0 phase of the cell cycle (G0) in which DNA end resection is or has been activated generating single-stranded DNA, comprising promoting or stimulating the assembly or occurrence of BRCA1-PALB2 or BRCA1-PALB2-BRCA2 complexes in the cell. In an embodiment, the assembly of the complexes is promoted or stimulated by administering an agent that promotes or stimulates the assembly or occurrence of BRCA1-PALB2 or BRCA1-PALB2-BRCA2 complexes identified using a method of the invention.

The invention also provides a method for repairing DNA double-strand breaks in a cell in the G1 phase of the cell cycle (G1) or G0 phase of the cell cycle (G0) in which DNA end resection is or has been activated generating single-stranded DNA, comprising contacting the cell with BRCA1-PALB2 or BRCA1-PALB2-BRCA2 complexes.

The invention also provides a method for repairing DNA double-strand breaks in a cell in G1 or G0 in which DNA end resection is or has been activated generating single-stranded DNA, the method comprising (a) inhibiting KEAP1 and/or CRL3-KEAP1; (b) blocking the degradation of USP11 or promoting or stimulating USP11 activity; (c) administering USP11 or an agonist thereof; and/or (d) inhibiting CRL3-KEAP1 and blocking the degradation of USP11.

A method for activating homologous recombination in a cell may further comprise activating or promoting single strand DNA (ssDNA) generation pathways. In an aspect, ssDNA generation pathways are activated by DNA end resection. In an embodiment, a method for activating homologous recombination in a cell further comprises activating DNA end resection.

In an embodiment, DNA end resection is activated or promoted by inhibiting 53BP1 (or RIF1) expression or activity (e.g., recruitment of 53BP1 to DSB sites) and/or upregulating or expressing CtIP. In an embodiment, DNA end resection is activated or promoted by inhibiting 53BP1 (or RIF1) expression or activity (e.g., recruitment of 53BP1 to DSB sites) and upregulating or expressing CtIP. In an embodiment, the method involves inhibiting 53BP1 using antagonists, including without limitation short interfering (si) RNA, short hairpin (sh) RNA and microRNAs (miRNAs) or an inhibitor of the histone deacetylase (HDAC) family of enzymes (for example, trichostatin A), and using an analog of CtIP that mimics constitutive phosphorylation, for example CtIP-Thr847Glu.

A method for activating homologous recombination in a cell may comprise activating BRCA1 recruitment to DNA double-strand break (DSB) sites. In an embodiment, BRCA1 recruitment is activated by inhibiting expression of 53BP1 (TP53BP1) or RIF1, or inhibiting the recruitment of 53BP1 or RIF1 to DSB sites. 53BP1 or RIF1 may be inhibited using antagonists, including without limitation short interfering (si) RNA, short hairpin (sh) RNA and microRNAs (miRNAs). In an embodiment, 53BP1 is inhibited with an inhibitor of the histone deacetylase (HDAC) family of enzymes, in particular a histone deacetylase inhibitor (HDACi), preferably trichostatin (Fukuda T. et al, Cancer Sci. 2015 August; 106(8):1050-6. doi: 10.1111/cas.12717. Epub 2015 Jul. 14).

In an aspect, a method for activating or stimulating homologous recombination in a cell further comprises a gene editing system. In an aspect the gene editing system comprises contacting the cell with a nuclease. Examples of nucleases include without limitation, zinc finger nucleases (ZFNs), engineered meganucleases, transcription activator like effector nucleases (TALENS), mega or homing endonucleases, clustered regularly interspaced short palindromic repeats (CRISPR)-associated (Cas) protein, Ttago nucleases, and fusions between nucleases, such as mega-TALs and compact TALENs.

In an aspect, the gene editing steps comprise a TALEN system.

In an aspect, the gene editing steps comprise a ZFN system.

In an aspect, the gene editing steps comprise a CRISPR/Cas9 system.

In aspects of the invention the gene editing system may correct a genomic modification. A genetic modification may comprise at least one mutation in a polynucleotide sequence having a locus associated with a genetic disorder. In an aspect, the genomic modification is selected from the group consisting of insertions, deletions and combinations thereof. In some embodiments, the genetic disorder is a monogenetic disorder. In some embodiments, the disorder is a multigenetic disorder. In some embodiments, the disorder is associated with one or more SNPs. In particular embodiments of the invention, the genomic modification corrects a point mutation.

In an aspect of a method of the invention to correct a genomic modification, the gene editing system comprises contacting the cell with a clustered regularly interspaced short palindromic repeats (CRISPR)-associated (Cas) protein and from one to two ribonucleic acids, wherein the ribonucleic acids direct Cas protein to and hybridize to a selected motif of a target polynucleotide sequence associated with a genetic disorder, wherein the target polynucleotide sequence is cleaved.

In an aspect, the invention provides a method for altering a genetic disorder associated with a target polynucleotide sequence in a cell comprising: (1) contacting the cell with a system which activates homologous recombination in the cell wherein the system comprises BRCA1-PALB2 or BRCA1-PALB2-BRCA2 or agents that maintain the BRCA1-PALB2 or BRCA1-PALB2-BRCA2 interactions throughout the cell cycle; and (2) contacting the target polynucleotide sequence with a clustered regularly interspaced short palindromic repeats-associated (Cas) protein and from one to two ribonucleic acids, wherein the ribonucleic acids direct Cas protein to and hybridize to a selected motif of the target polynucleotide sequence, wherein the target polynucleotide sequence is cleaved. The method may reduce expression of the target polynucleotide sequence, knock out the target polynucleotide sequence, or correct the target polynucleotide sequence from an undesired sequence to a desired sequence.

In an aspect, the invention provides a method for altering a genetic disorder associated with a target polynucleotide sequence in a cell comprising: (1) contacting the cell with a system which activates homologous recombination in the cell wherein the system comprises a kit, vector(s) or composition of the invention, in particular the system comprises an inhibitor of 53BP1, a KEAP1 inhibitor or DCAF10 inhibitor, and an analog of CtIP that mimics constitutive phosphorylation, preferably the system comprises a KEAP1 inhibitor, an inhibitor of 53BP1 chosen from short interfering (si) RNA, short hairpin (sh) RNA and microRNAs (miRNAs), and CtIP-Thr847Glu; and (2) contacting the target polynucleotide sequence with a clustered regularly interspaced short palindromic repeats-associated (Cas) protein and from one to two ribonucleic acids, wherein the ribonucleic acids direct Cas protein to and hybridize to a selected motif of the target polynucleotide sequence, wherein the target polynucleotide sequence is cleaved. The method may reduce expression of the target polynucleotide sequence, knock out the target polynucleotide sequence, or correct the target polynucleotide sequence from an undesired sequence to a desired sequence.

The invention contemplates a method for treating or preventing a genetic disorder in a subject, the method comprising altering a target polynucleotide sequence associated with the genetic disorder in a cell by contacting the cell with a system which activates homologous recombination in the cell wherein the system comprises BRCA1-PALB2 or BRCA1-PALB2-BRCA2 or agents that maintain the BRCA1-PALB2 or BRCA1-PALB2-BRCA2 interactions throughout the cell cycle; and contacting the target polynucleotide sequence with a clustered regularly interspaced short palindromic repeats-associated (Cas) protein and from one to two ribonucleic acids, wherein the ribonucleic acids direct Cas protein to and hybridize to a selected motif of the target polynucleotide sequence, wherein the target polynucleotide sequence is cleaved, thereby treating or preventing the genetic disorder.

In an aspect, a method is provided for treating or preventing a genetic disorder in a subject, the method comprising (a) altering a target polynucleotide sequence associated with the genetic disorder in a cell by contacting the cell with a system which activates homologous recombination in the cell wherein the system comprises a kit, vector(s) or composition of the invention, in particular the system comprises an inhibitor of 53BP1, a KEAP1 inhibitor or DCAF10 inhibitor, and an analog of CtIP that mimics constitutive phosphorylation, preferably the system comprises a KEAP1 inhibitor, an inhibitor of 53BP1 chosen from short interfering (si) RNA, short hairpin (sh) RNA and microRNAs (miRNAs), and CtIP-Thr847Glu; and (b) contacting the target polynucleotide sequence with a clustered regularly interspaced short palindromic repeats-associated (Cas) protein and from one to two ribonucleic acids, wherein the ribonucleic acids direct Cas protein to and hybridize to a selected motif of the target polynucleotide sequence, wherein the target polynucleotide sequence is cleaved, thereby treating or preventing the genetic disorder.

A method for treating or preventing a genetic disorder may comprise introducing the cell into the subject, thereby treating or preventing the genetic disorder associated with the target polynucleotide sequence. The method may comprise repairing the cleaved target polynucleotide sequence by inserting an exogenous template polynucleotide, wherein said repair results in a mutation comprising an insertion, deletion, or substitution of one or more nucleotides of said target polynucleotide sequence.

In an aspect, the target polynucleotide sequence is associated with a genetic disorder of the lung. In an embodiment the target polynucleotide sequence is associated with cystic fibrosis, in particular the polynucleotide sequence is the cystic fibrosis transmembrane conductor receptor (CFTR) locus. Mutations in the CFTR (e.g., deletion of phenylalanine at position 508 in exon 11) cause cystic fibrosis.

In an aspect, the target polynucleotide sequence is associated with a genetic disorder of muscle. In an aspect, the target polynucleotide sequence is associated with muscular dystrophies. In an aspect, the target polynucleotide sequence is associated with Duchenne muscular dystrophy (DMD) (mutations in the dystrophin gene). In an aspect, the target polynucleotide sequence is associated with Becker muscular dystrophy (mutations in the dystrophin gene). In an aspect the target polynucleotide is associated with myotonic dystrophy type 1 (mutations in the DMPK gene) or myotonic dystrophy type 2 (mutations in the CNBP gene). In an aspect, the target polynucleotide sequence is associated with sickle cell anemia (mutated HBB hemoglobin).

In aspects of the invention, the targeted polynucleotide sequence is associated with a genetic disorder of the liver. In an aspect, the target polynucleotide sequence is associated with alpha-1 antitrypsin deficiency (mutations in the SERPINA1 gene). In an aspect, the targeted polynucleotide sequence is associated with Wilson disease (mutations in the gene encoding the ATP7B Cu translocase).

In an aspect, the methods of the invention further comprise providing a functional protein with enhanced characteristics as compared to its naturally occurring counterpart, in particular a functional protein lacking or deficient in a subject, for example for treating genetic disorders. In embodiments of the invention, the methods comprise integrating a sequence encoding a functional protein in a cell in a subject in need thereof by sequential administration of a gene editing system and one or more transgene encoding a non-naturally occurring protein with enhanced properties as compared to its naturally occurring counterpart. In other embodiments, the methods comprise administering to the subject a genetically modified cell expressing a functional version of one or more proteins aberrantly expressed in a subject. Thus, an isolated cell may be introduced into the subject (ex vivo cell therapy) or a cell may be modified when it is part of the subject (in vivo). In certain embodiments, transgene(s) are delivered using a viral vector, a non-viral vector and/or combinations thereof.

The invention also provides a method for suppressing homologous recombination in a cell, in particular a cell in G1, comprising suppressing the assembly of BRCA1-PALB2-BRCA2 complexes in the cell. In an embodiment, the interaction is suppressed by administering KEAP1 or CRL3-KEAP1 or an agonist thereof. In an embodiment, the interaction is suppressed by administering a USP11 antagonist/inhibitor (e.g., mitoxantrone). In an embodiment, the interaction is suppressed by administering an agent that suppresses homologous recombination identified using a method of the invention.

Components of the methods of the invention may be delivered by delivery systems known in the art, including without limitation viral based systems or non-viral based systems. Conventional viral based systems may comprise, for example, retroviral, lentivirus, adenoviral, adeno-associated and herpes simplex virus vectors for gene transfer. In an aspect, the expression vector is selected from the group consisting of a plasmid vector, a lentiviral vector, an adenoviral vector, and an adeno-associated virus vector. In an embodiment, the viral based system, is an adenoviral vector or adeno-associated viral vector. Examples, of non-viral based systems include lipofection, nucleofection, microinjection, biolistics, virosomes, liposomes, immunoliposomes, polycation or lipid:nucleic acid conjugates, naked DNA, artificial virons and agent-enhanced uptake of DNA.

In an aspect, the invention provides vectors comprising activators or modulators of homologous recombination, and optionally activators or modulators of DNA end resection. In an aspect, the invention provides a vector (e.g. viral vector) comprising one or more of the following components encoded in the vector: 1) an activator of DNA end resection, for example, an inhibitor of 53BP1 (or RIF) expression or activity and/or a CtIP compound that mimics constitutive phosphorylation; 2) a factor that activates homologous recombination, for example, a factor that maintains BRCA1-PALB2 or BRCA1-PALB2-BRCA2 interactions during the cell cycle; and, optionally, 3) components of a gene editing system, in particular components of a CRISPR system, a TALEN system or a zinc finger nuclease system. In an embodiment, the components of the gene editing system are encoded in one or more separate expression vectors.

In another aspect, the invention provides a composition comprising activators or modulators of homologous recombination, and optionally activators or modulators of DNA end resection. In an aspect, the invention provides a composition comprising one or more of the following components: 1) an activator of DNA end resection, for example, an inhibitor of 53BP1 (or RIF) expression or activity and/or a CtIP compound that mimics constitutive phosphorylation; 2) a factor that activates homologous recombination, for example, a factor that maintains BRCA1-PALB2 or BRCA1-PALB2-BRCA2 interactions during the cell cycle; and, optionally, 3) components of a gene editing system, in particular components of a CRISPR system, TALEN system or zinc finger nuclease system. In an embodiment, the components of the gene editing system are in one or more separate compositions.

Examples of activators of DNA end-resection include without limitation, the coding sequence of CtIP-Thr847Glu, a shRNA against the TP53BP1 mRNA, and a shRNA against KEAP1. The shRNA against TP53BP1 may be substituted with a shRNA against RIF1 or agents that block 53BP1 recruitment to DSB sites including a dominant-negative 53BP1 protein. The shRNA against KEAP1 may be substituted with a the coding sequence of a PALB2 mutant that contains mutations of its Lys20, Lys25 and Lys30 residues or that contains a mutation that disrupts its interaction with KEAP1.

Examples of factors that maintain BRCA1-PALB2 or BRCA1-PALB2-BRCA2 interactions during the cell cycle include without limitation, inhibitors of KEAP1, inhibitors of DCAF10, RNA interference agents that maintain USP11 expression in G0 and G1 cells or a mutated form of PALB2 that is insensitive to ubiquitylation by KEAP1-CUL3-RBX1 which involves the mutation of one or more of the Lys20, Lys25 or Lys30 residues. An example of a KEAP1 inhibitor is the monobody that is a potent competitive inhibitor of the KEAP1-NRF2 interaction disclosed in Guntas, G. et al, [44]. KEAP1 inhibitors are also described, for example in Canning P. et al, Acta Pharm Sin B., 2015 (4):285-99 and Wells, G., Biochem Soc Trans. 2015, 43(4): 674-9.

In an embodiment, a vector of the invention comprises sequences encoding an inhibitor of 53BP1, a KEAP1 inhibitor or DCAF10 inhibitor, and an analog of CtIP that mimics constitutive phosphorylation. In a particular embodiment, a vector of the invention comprises sequences encoding a KEAP1 inhibitor (e.g., R1 KEAP1 inhibitor; see Example 3), an inhibitor of 53BP1 and CtIP-Thr847Glu. In a particular embodiment, a vector of the invention comprises sequences encoding a KEAP1 inhibitor (e.g., R1 KEAP1 inhibitor; see Example 3), an inhibitor of 53BP1 chosen from short interfering (si) RNA, short hairpin (sh) RNA and microRNAs (miRNAs), and CtIP-Thr847Glu.

In an embodiment, a composition of the invention comprises an inhibitor of 53BP1, a KEAP1 inhibitor or DCAF10 inhibitor, and an analog of CtIP that mimics constitutive phosphorylation. In a particular embodiment, a composition of the invention comprises a KEAP1 inhibitor (e.g., R1 KEAP1 inhibitor; see Example 3), an inhibitor of 53BP1 and CtIP-Thr847Glu. In a particular embodiment, a composition of the invention comprises a KEAP1 inhibitor (e.g., R1 KEAP1 inhibitor; see Example 3), an inhibitor of 53BP1 chosen from short interfering (si) RNA, short hairpin (sh) RNA and microRNAs (miRNAs), and CtIP-Thr847Glu.

Kits

The invention further provides a kit for performing an assay or method disclosed herein or comprising compositions or vectors disclosed herein. In an embodiment, a kit of the invention comprises at least one reagent for determining USP11 activity in a sample. In another embodiment, a kit of the invention comprises at least one reagent for determining BRCA1-PALB2-BRCA2, PALB2-KEAP1, BRCA1-PALB2, USP11-DCAF10, or USP11-PALB2 complexes in a sample. In another embodiment, a kit of the invention comprises at least one reagent for determining BRCA1-PALB2-BRCA2, PALB2-KEAP1 or USP11-PALB2 complexes in a sample. In another embodiment, a kit of the invention comprises reagents for determining the levels of BRCA1, BRCA2, PALB2, USP11, DCAF10 and KEAP1 in a sample. In another embodiment, a kit of the invention comprises at least one reagent for determining ubiquitylation of PALB2, in particular ubiquitylation of the N-terminus of PALB2, in a sample. In some embodiments the reagent is an antibody or a nucleic acid or primers for use in a PCR reaction.

A kit may also comprise instructions for suitable operational parameters in the form of an insert. The instructions may inform a consumer about how to collect the sample. The kit may comprise samples, to be used as standard(s) for calibration and comparison. The kit may also comprise instructions to compare the level of activity or biomarkers detected in a sample with a calibration sample or chart. The kit may also include instructions indicating what level of activity or biomarkers is diagnostic of a disease disclosed herein.

In an aspect, the invention provides a kit comprising one or more of the components of a method of the invention for activating homologous recombination and optionally components of a gene editing system. A kit of the invention may also include or be used in combination with a CRISPR system, a TALEN system or zinc finger nuclease system. In an embodiment, a kit of the invention includes or is used in combination with a CRISPR system. In an embodiment, a kit of the invention includes or is used in combination with a TALEN system. In an embodiment, a kit of the invention includes or is used in combination with a zinc finger nuclease system.

In some embodiments, a kit of the invention comprises vector systems and instructions for using the kit. In an aspect, the kit comprises a vector comprising activators of DNA end resection and activators of homologous recombination discussed herein. In an aspect, the kit comprises one or more vectors (e.g. viral vectors) comprising one or more of the following components: 1) activators of DNA end resection, for example, inhibitors of 53BP1 (or RIF) expression or activity and/or a CtIP compound that mimics constitutive phosphorylation; 2) factors that activate homologous recombination, for example, factors that maintain BRCA1-PALB2 interactions during the cell cycle; and, optionally, 3) components of a gene editing system, in particular components of a CRISPR system, TALEN system or zinc finger nuclease system. Examples of factors that maintain BRCA1-PALB2 interactions during the cell cycle are described herein and include without limitation, inhibitors of KEAP1, for example, RNA interference agents that maintain USP11 expression in G0 and G1 cells or a mutated form of PALB2 that is insensitive to ubiquitylation by KEAP1-CUL3-RBX1 which involves the mutation of one or more of the Lys20, Lys25 or Lys30 residues. Examples of activators of DNA end resection include without limitation, the coding sequence of CtIP-Thr847Glu, a shRNA against the TP53BP1 mRNA, and a shRNA against KEAP1. The shRNA against TP53BP1 may be substituted with a shRNA against RIF1 or agents that block 53BP1 recruitment to DSB sites including a dominant-negative 53BP1 protein. The shRNA against KEAP1 may be substituted with a coding sequence of a PALB2 mutant that contains mutations of its Lys20, Lys25 and Lys30 residues or that contains a mutation that disrupts its interaction with KEAP1.

In an embodiment, a kit of the invention comprises one or more vectors comprising sequences encoding an inhibitor of 53BP1, a KEAP1 inhibitor or DCAF10 inhibitor, and an analog of CtIP that mimics constitutive phosphorylation. In a particular embodiment, a kit of the invention comprises one or more vectors comprising sequences encoding a KEAP1 inhibitor (e.g., R1 KEAP1 inhibitor; see Example 3), an inhibitor of 53BP1 and CtIP-Thr847Glu. In a particular embodiment, a kit of the invention comprises one or more vectors comprising sequences encoding a KEAP1 inhibitor (e.g., R1 KEAP1 inhibitor; see Example 3), an inhibitor of 53BP1 chosen from short interfering (si) RNA, short hairpin (sh) RNA and microRNAs (miRNAs), and CtIP-Thr847Glu.

In some embodiments, a kit of the invention comprises a composition of the invention and instructions for using the kit. In an aspect the kit comprises a composition comprising activators or modulators of DNA end-resection and activators or modulators of homologous recombination discussed herein. In an aspect, the kit comprises a composition comprising one or more of the following components: 1) an activator of DNA end resection, for example, an inhibitor of 53BP1 (or RIF) expression or activity and/or a CtIP compound that mimics constitutive phosphorylation; 2) a factor that activates homologous recombination, for example, a factor that maintains BRCA1-PALB2 or BRCA1-PALB2-BRCA2 interactions during the cell cycle; and, optionally, 3) components of a gene editing system, in particular components of a CRISPR system, TALEN system or zinc finger nuclease system. In an embodiment, the components of the gene editing system are in separate kit(s).

In an embodiment, a kit of the invention comprises a composition comprising an inhibitor of 53BP1, a KEAP1 inhibitor or DCAF10 inhibitor, and an analog of CtIP that mimics constitutive phosphorylation. In a particular embodiment, a kit of the invention comprises a composition comprising a KEAP1 inhibitor (e.g., R1 KEAP1 inhibitor; see Example 3), an inhibitor of 53BP1 and CtIP-Thr847Glu. In a particular embodiment, a kit of the invention comprises a composition comprising a KEAP1 inhibitor (e.g., R1 KEAP1 inhibitor; see Example 3), an inhibitor of 53BP1 chosen from short interfering (si) RNA, short hairpin (sh) RNA and microRNAs (miRNAs), and CtIP-Thr847Glu.

In some aspects, a kit of the invention is used in combination with a gene editing kit, in particular a kit for a CRISPR system, a TALEN system or zinc finger nuclease system. Gene editing kits are commercially available, for example from Addgene (Cambridge, Mass.), ThermoFisher Scientific, System Biosciences Inc., and OriGene Technologies (MD), Clontech.

The following non-limiting examples are illustrative of the present invention:

Example 1

The following materials and methods were used in the study described in the Example.

Plasmids

The cDNA of PALB2 was obtained from the Mammalian Gene Collection (MGC). Full length PALB2 and BRCA1 were amplified by PCR, subcloned into pDONR221 and delivered into the pDEST-GFP, pDEST-Flag and the mCherry-LacR vectors using Gateway cloning technology (Invitrogen). Similarly, the coiled-coil domain of BRCA1 (residues 1363-1437) was amplified by PCR, subcloned into the pDONR221 vector and delivered into both mCherry-LacR and pDEST-GFP vectors. The N-terminal domain of PALB2 was amplified by PCR and introduced into the GST expression vector pET30-2-His-GST-TEV [31] using the EcoRI/XhoI sites. The coiled-coil domain of BRCA1 was cloned into pMAL-c2 using the BamHI/SalI sites. Truncated forms of PALB2 were obtained by introducing stop codons or deletions through site-directed mutagenesis. Full-length CtIP was amplified by PCR, subcloned into the pDONR221 and delivered into the lentiviral construct pCW57.1 (a gift of Dr. David Root; Addgene plasmid #41393) using Gateway cloning technology (Invitrogen). The USP11 cDNA was a gift of David Cortez and was amplified by PCR and cloned into the pDsRed2-C1 vector using the EcoRI/SalI sites. The bacterial codon-optimized coding sequence of pig USP11 (USP11) was subcloned into the 6×His-GST vector pETM-30-Htb using the BamHI/EcoRI sites. siRNA-resistant versions of PALB2, BRCA1 and USP11 constructs were generated as previously described [14]. Full-length CUL3 and RBX1 were amplified by PCR from a human pancreas cDNA library (Invitrogen) as previously described [32] and cloned into the dual expression pFBDM vector using NheI/XmaI and BssHII/NotI respectively. The NEDD8 cDNA was a gift of Dmitris Xirodimas and was fused to a double StrepII tag at its C-terminus in the pET17b vector (Millipore). Human DEN1 was amplified from a vector supplied by Aude Echalier and fused to a non-cleavable N-terminal StrepII2×tag by PCR and inserted into a pET17b vector. The pCOOL-mKEAP1 plasmid was a gift from Dr. Feng Shao. The pcDNA3-HA2-KEAP1 and pcDNA3-HA2-KEAP1ΔBTB were gifts from Dr. Yue Xiong (Addgene plasmids #21556 and 21593). gRNAs were synthesized and processed as described previously [33]. Annealed gRNAs were cloned into the Cas9-expressing vectors pSpCas9(BB)-2A-Puro (PX459) or pX330-U6-Chimeric_BB-CBh-hSpCas9, a gift from Feng Zhang (Addgene plasmids #48139 and 42230). The gRNAs targeting the LMNA or the PML locus and the mClover-tagged LMNA or PML are previously described [45] The lentiviral packaging vector psPAX2 and the envelope vector VSV-G were a gift from Didier Trono (Addgene plasmids #12260 and 12259). His$_6$-Ubiquitin was cloned into the pcDNA5-FRT/TO backbone using the XhoI/HindIII sites. All mutations were introduced by site-directed mutagenesis using QuikChange (Stratagene) and all plasmids were sequence-verified.

Cell Culture and Plasmid Transfection

All culture media were supplemented with 10% fetal bovine serum (FBS). U-2-OS (U2OS) cells were cultured in McCoy's medium (Gibco). 293T cells were cultured in DMEM (Gibco). Parental cells were tested for mycoplasma contamination and authenticated by STR DNA profiling. Plasmid transfections were carried out using Lipofectamine 2000 Transfection Reagent (Invitrogen) following the manufacturer's protocol. Lentiviral infection was carried out as previously described [18]. U2OS and 293T cells were purchased from ATCC. U2OS 256 cells were a gift from R. Greenberg.

Antibodies

The following antibodies were employed: rabbit anti-53BP1 (A300-273A, Bethyl), rabbit anti-53BP1 (sc-22760, Santa Cruz), mouse anti-53BP1 (#612523, BD Biosciences), mouse anti-γ-H2AX (clone JBW301, Millipore), rabbit anti-γ-H2AX (#2577, Cell Signaling Technologies), rabbit anti-KEAP1 (ab66620, Abcam), rabbit anti-NRF2 (ab62352, Abcam), mouse anti-Flag (clone M2, Sigma), mouse anti-tubulin (CP06, Calbiochem), mouse anti-GFP (#11814460001, Roche), mouse anti-CCNA (MONX10262, Monosan), rabbit anti-BRCA2 (ab9143, Abcam), mouse anti-BRCA2 (OP95, Calbiochem), rabbit anti-BRCA1 (#07-

434, Millipore), rabbit anti-USP11 (ab109232, Abcam), rabbit anti-USP11 (A301-613A, Bethyl), rabbit anti-RAD51 (#70-001, Bioacademia), mouse anti-BrdU (RPN202, GE Healthcare), mouse anti-F1(2 (BMLPW8810, Enzo), rabbit anti-PALB2 [34], rabbit anti-GST (sc-459, Santa Cruz), rabbit anti-CUL3 (A301-108A, Bethyl), mouse anti-MBP (E8032, NEB), mouse anti-HA (clone 12CA5, a gift of Dr. M. Tyers), rabbit anti-Ubiquitin (Z0458, Dako) and mouse anti-actin (CP01, Calbiochem). The following antibodies were used as secondary antibodies in immunofluorescence microscopy: Alexa Fluor 488 donkey anti-rabbit IgG, Alexa Fluor 488 donkey anti-goat IgG, Alexa Fluor 555 donkey anti-mouse IgG, Alexa Fluor 555 donkey anti-rabbit IgG, Alexa Fluor 647 donkey anti-mouse IgG, Alexa Fluor 647 donkey anti-human IgG, Alexa Fluor 647 donkey anti-goat IgG (Molecular Probes).

RNA Interference

All siRNAs employed in this study were single duplex siRNAs purchased from ThermoFisher. RNA interference (RNAi) transfections were performed using Lipofectamine RNAiMax (Invitrogen) in a forward transfection mode. The individual siRNA duplexes used were: BRCA1 (D-003461-05), PALB2 (D-012928-04), USP11 (D-006063-01), CUL1 (M-004086-01), CUL2 (M-007277-00), CUL3 (M-010224-02), CUL4A (M-012610-01), CUL4B (M-017965-01), CUL5 (M-019553-01), KEAP1 (D-12453-02), RAD51 (M-003530-04), CtIP/RBBP8 (M-001376-00), BRCA2 (D-003462-04), 53BP1 (D-003549-01) and non-targeting control siRNA (D-001210-02). Except when stated otherwise, siRNAs were transfected 48 h prior to cell processing.

Inhibitors and Fine Chemicals

The following drugs were employed at the indicated concentrations: cycloheximide (CHX; Sigma) at 100 ng/mL$^{-1}$, camptothecin (CPT; Sigma) at 0.2 µM, ATM inhibitor (KU55933; Selleck Chemicals) at 10 µM, ATR inhibitor (VE-821; gift of Philip Reaper) at 10 µM, DNA-PKcs inhibitor (NU7441; Genetex) at 10 µM, proteasome inhibitor MG132 (Sigma) at 2 µM, Lovastatin (S2061; Selleck Chemicals) at 40 µM, Doxycycline (#8634-1; Clontech), Nedd8-activating enzyme inhibitor (MLN4929; Active Biochem) at 5 µM and olaparib (Selleck) at the indicated concentrations.

Immunofluorescence Microscopy

In most cases, cells were grown on glass coverslips, fixed with 2% (w/v) paraformaldehyde in PBS for 20 min at room temperature, permeabilized with 0.3% (v/v) Triton X-100 for 20 min at room temperature and blocked with 5% BSA in PBS for 30 min at room temperature. Alternatively, cells were fixed with 100% cold methanol for 10 min at −20° C. and subsequently washed with PBS for 5 min at room temperature before PBS-BSA blocking. Cells were then incubated with the primary antibody diluted in PBS-BSA for 2 h at room temperature. Cells were next washed with PBS and then incubated with secondary antibodies diluted in PBS-BSA supplemented with 0.8 µg/ml of DAPI to stain DNA for 1 h at room temperature. The coverslips were mounted onto glass slides with Prolong Gold mounting agent (Invitrogen). Confocal images were taken using a Zeiss LSM780 laser-scanning microscope. For G1 vs. S/G2 analysis of the BRCA1-PALB2-BRCA2 axis, cells were first synchronized with a double-thymidine block, released to allow entry into S phase and exposed to 2 or 20 Gy of X-irradiation at 5 h and 12 h post-release and fixed at 1 to 5 hours post-treatment (where indicated). For the examination of DNA replication, cells were pre-incubated with 30 µM BrdU for 30 min before irradiation and processed as previously described.

CRISPR/Cas9 genome editing of USP11/KEAP1

293T and U2OS cells were transiently transfected with 3 distinct sgRNAs targeting either 53BP1, USP11 or KEAP1 and expressed from the pX459 vector containing Cas9 followed by the 2A-Puromycin cassette. The next day, cells were selected with puromycin for 2 days and subcloned to form single colonies or subpopulations. Clones were screened by immunoblot and/or immunofluorescence to verify the loss of 53BP1, USP11 or KEAP1 expression and subsequently characterized by PCR and sequencing. The genomic region targeted by the CRISPR/Cas9 was amplified by PCR using Turbo Pfu polymerase (Agilent) and the PCR product was cloned into the pCR2.1 TOPO vector (Invitrogen) before sequencing.

Olaparib Clonogenic Assay 293T cells were incubated with the indicated doses of olaparib (Selleck Chemicals) for 24 h, washed once with PBS and counted by trypan blue staining. Five-hundred cells were then plated in duplicate for each condition. The cell survival assay was performed as previously described [35].

Recombinant Protein Production

GST and MBP fusions proteins were produced as previously described [36, 37]. Briefly, MBP proteins expressed in *Escherichia coli* were purified on amylose resin (New England Biolabs) according to the batch method described by the manufacturer and stored in 1×PBS, 5% glycerol. GST proteins expressed in *E. coli* were purified on glutathione sepharose 4B (GE Healthcare) resin in 50 mM Tris HCl pH 7.5, 300 mM NaCl, 2 mM dithiothreitol (DTT), 1 mM EDTA, 15 µg/mL$^{-1}$ AEBSF and 1× Complete protease inhibitor cocktail (Roche). Upon elution from the resin using 50 mM glutathione in 50 mM Tris HCl pH 8, 2 mM DTT, the His$_6$-GST tag was cleaved off using His-tagged TEV protease (provided by F. Sicheri) in 50 mM Tris HCl pH 7.5, 150 mM NaCl, 10 mM glutathione, 10% glycerol, 2 mM sodium citrate and 2 mM β-mercaptoethanol. His$_6$-tagged proteins were depleted using Ni-NTA-agarose beads (Qiagen) in 50 mM Tris HCl pH 7.5, 300 mM NaCl, 20 mM imidazole, 5 mM glutathione, 10% glycerol, 1 mM sodium citrate and 2 mM β-mercaptoethanol followed by centrifugal concentration (Amicon centrifugal filters, Millipore). GST-mKEAP1 was purified as described previously [38], with an additional anion exchange step on a HiTrap Q HP column (GE Healthcare). The GST tag was left on the protein for in vitro experiments. Purification of CUL3 and RBX1 was performed as previously described [32]. Nedd8 and Den1 were expressed in *E. coli* BL21 grown in Terrific broth media and induced overnight with 0.5 mM isopropyl-β-D-thiogalactoside (IPTG) at 16° C. Cells were harvested and resuspended in wash buffer (400 mM NaCl, 50 mM Tris-HCl, pH 8, 5% glycerol, 2 mM DTT), supplemented with lysozyme, universal nuclease (Pierce), benzamidine, leupeptin, pepstatin, PMSF and Complete protease inhibitor cocktail (Roche), except for DEN1-expressing cells where the protease inhibitors were omitted. Cells were lysed by sonication and the lysate was cleared by centrifugation at 20,000 rpm for 50 min. The soluble supernatant was bound to a 5 ml Strep30 Tactin Superflow Cartridge with a flow rate of 3 ml/min$^{-1}$ using a peristaltic pump. The column was washed with 20 column volumes (CV) of washing buffer and eluted with 5 CV washing buffer, diluted 1:2 in water to reduce the final salt concentration, and supplemented with 2.5 mM desthiobiotin. The elution fractions were pooled and concentrated to a total volume of 4 ml using a 3 kDa cut-off Amicon concentrator. DEN1 was further purified over a Superdex 75 size exclusion column, buffer exchanged into 150 mM NaCl, HEPES, pH 7.6, 2% glycerol and 1 mM DTT. The C-terminal pro-peptide and StrepII2x-tag were removed by incubation with StrepII2x-DEN1 in 1:20 molar ratio for 1 hour at room temperature. The DEN1 cleavage reaction was buffer exchanged on a Zeba MWCO desalting column (Pierce), to remove the desthiobiotin, and passed through a Strep-Tactin Cartridge, which retains the C-terminal pro-peptide and DEN1. The GST-tagged *Sus scrofa* (pig) USP11 proteins were expressed in *E. coli* as described [39]. Cells were lysed by lysozyme treatment and sonication in 50 mM Tris pH 7.5, 300 mM NaCl, 1 mM EDTA, 1 mM AEBSF, 1× Protease Inhibitor mix (284 ng/ml leupeptin, 1.37 µg/ml$^{-1}$ pepstatin A, 170 µg/ml$^{-1}$ PMSF and 330 µg/ml$^{-1}$ benzamidine) and 5% glycerol. Cleared lysate was applied to a column packed with glutathione sepharose 4B (GE Healthcare), washed extensively with lysis buffer before elution in 50 mM Tris pH 7.5, 150 mM NaCl, 5% glycerol and 25 mM reduced glutathione. DUB activity was assayed on fluorogenic Ubiquitin-AMC (Enzo life sciences), measured using a Synergy Neo microplate reader (Biotek). His$_6$-TEV-Ubiquitin-G76C was purified on chelating HiTrap resin, following the manufacturers' instructions, followed by size exclusion chromatography on a S-75 column (GE healthcare). The protein was extensively dialysed in 1 mM acetic acid and lyophilised.

In Vitro Ubiquitylation and Deubiquitylation of PALB2

HA-tagged N-terminal fragments of PALB2 (1-103) (1 µM) were in vitro ubiquitylated using 50 µM wild-type (Ubi WT, Boston Biochem) or a lysine-less ubiquitin (Ubi K0, Boston Biochem), 100 nM human UBA1 (E1), 500 nM CDC34 (provided by F. Sicheri and D. Ceccarelli), 250 nM neddylated CUL3/RBX1, 375 nM GST-mKEAP1 and 1.5 mM ATP in a buffer containing 50 mM Tris HCl pH 7.5, 20 mM NaCl, 10 mM MgCl$_2$ and 0.5 mM DTT. Ubiquitylation reactions were carried out at 37° C. for 1 hour, unless stated otherwise. For USP11-mediated deubiquitylation assays, HA-PALB2 (1-103) was first ubiquitylated using lysine-less ubiquitin with enzyme concentrations as described above in 50 µL reactions in a buffer containing 25 mM HEPES pH 8, 150 mM NaCl, 10 mM MgCl$_2$, 0.5 mM DTT and 1.5 mM ATP for 1.5 h at 37° C. Reactions were stopped by the addition of 1 unit Apyrase (New England Biolabs). Reaction products were mixed at a 1:1 ratio with wild-type or catalytically inactive (C270S) USP11, or USP2 (provided by Dr. F. Sicheri and E. Zeqiraj) using final concentrations of 100 nM, 500 nM and 2500 nM (USP11) and 500 nM (USP2) and incubated for 2 h at 30° C. in a buffer containing 25 mM HEPES pH 8, 150 mM NaCl, 2 mM DTT, 0.1 mg/mL BSA, 0.03% Brij-35, 5 mM MgCl$_2$, 0.375 mM ATP.

Pulldown Experiments Between Purified PALB2 and BRCA1

PALB2 in vitro ubiquitylation reaction products were diluted in a buffer at final concentration of 50 mM Tris-HCl pH 7.5, 150 mM NaCl, 5 mM MgCl$_2$, 0.25 mM DTT and 0.1% NP-40. 20 µg MBP or MBP-BRCA1-CC was coupled to amylose resin (New England Biolabs) in the above buffer supplemented with 0.1% BSA prior to addition of the ubiquitylation products. Pulldown reactions were performed at 4° C. for 2 h, followed by extensive washing.

Co-Immunoprecipitation

Cells were collected by trypsinization, washed once with PBS and lysed in 500 µL of lysis buffer (20 mM Tris-HCl pH 8.0, 150 mM NaCl, 10% glycerol, 2 mM EDTA, 1% NP-40, Complete protease inhibitors cocktail (Roche), cocktail of phosphatase inhibitors (Sigma) and N-ethylmaleimide to inhibit deubiquitination) on ice. Lysates were centrifuged at 15 000 g for 10 min at 4° C. and protein concentration was evaluated using absorbance at 280 nm. Equivalent amounts of proteins (~0.5-1 mg) were incubated with 2 µg of rabbit anti-PALB2, rabbit anti-USP11 antibody, rabbit anti-GFP antibody or normal rabbit IgG for 5 h at 4° C. A mix of protein A/protein G-Sepharose beads (Thermo Scientific) was added for an additional hour. Beads were collected by centrifugation, washed twice with lysis buffer and once with PBS, and eluted by boiling in 2× Laemmli buffer before analysis by SDS-PAGE and immunoblotting. For MS analysis of Flag-PALB2, 150×10$^6$ transiently transfected HEK293T cells were lysed in high-salt lysis buffer (50 mM Tris-HCl pH 7.5, 300 mM NaCl, 1 mM EDTA, 1% Triton X100, 3 mM MgCl$_2$, 3 mM CaCl$_2$), supplemented with Complete protease inhibitor cocktail (Roche), 4 mM 1,10-Phenantroline, 50 U benzonase and 50 U micrococcal nuclease. Cleared lysates were incubated with Flag-M2 agarose (Sigma), followed by extensive washing in lysis buffer and 50 mM ammoniumbicarbonate.

Mass Spectrometry

After immunoprecipitation of transiently transfected Flag-PALB2 from siCTRL-transfected or USP11 siRNA-depleted 293T cells, cysteine residues were reduced and alkylated on beads using 10 mM DTT (30 min. at 56° C.) and 15 mM 2-chloroacetamide (1 h at room temperature), respectively. Proteins were digested using limited trypsin digestion on beads (1 µg trypsin (Worthington, N.J., USA) per sample, 20 min at 37° C.), and dried to completeness. For LCMS/MS analysis, peptides were reconstituted in 5% formic acid and loaded onto a 12 cm fused silica column with pulled tip packed in-house with 3.5 µm Zorbax C18 (Agilent Technologies, CA, USA). Samples were analyzed using an Orbitrap Velos (Thermo Scientific, MA, USA) coupled to an Eksigent nanoLC ultra (AB SCIEX, CA). Peptides were eluted from the column using a 90 min linear gradient from 2% to 35% acetonitrile in 0.1% formic acid. Tandem MS spectra were acquired in a data-dependent mode for the top two most abundant multiply charged peptides and included targeted scans for five specific N-terminal PALB2 tryptic digest peptides (charge state 1+, 2+, 3+), either in non-modified form or including a diGly-ubiquitin trypsin digestion remnant. Tandem MS spectra were acquired using collision-induced dissociation. Spectra were searched against the human Refseq_V53 database using Mascot, allowing up to 4 missed cleavages and including carbamidomethyl (C), deamidation (NQ), oxidation (M), GlyGly (K) and LeuArgGlyGly (K) [SEQ ID NO: 4] as variable modifications.

In vitro ubiquitylated HA-PALB2 (1-103) (50 µL total reaction mix) was run briefly onto an SD S-PAGE gel, followed by total lane excision, in-gel reduction using 10 mM DTT (30 min at 56° C.), alkylation using 50 mM 2-chloroacetamide and trypsin digestion for 16 h at 37° C. Digested peptides were mixed with 20 µL of a mix of 10 unique heavy isotope-labeled N-terminal PALB2 (AQUA) peptides (covering full or partial tryptic digests of regions surrounding Lys 16, 25, 30 or 43, either in non-modified or diG-modified form; 80-1,200 fmol µ l$^{-1}$ per peptide, based on individual peptide sensitivity testing) before loading 6 µL onto a 12 cm fused silica column with pulled tip packed in-house with 3.5 µm Zorbax C18. Samples were measured on an Orbitrap ELITE (Thermo Scientific, MA, USA) coupled to an Eksigent nanoLC ultra (AB SCIEX, CA, USA). Peptides were eluted from the column using a 180 min linear gradient from 2% to 35% acetonitrile in 0.1% fotinic acid. Tandem MS spectra were acquired in a data-dependent mode for the top two most abundant multiply charged ions and included targeted scans for ten specific N-terminal PALB2 tryptic digest peptides (charge states 1+, 2+, 3+), either in light or heavy isotope-labeled form. Tandem MS spectra were acquired using collision induced dissociation. Spectra were searched against the human Refseq_V53 database using Mascot, allowing up to 2 missed cleavages and including carbamidomethyl (C), deamidation (NQ), oxidation (M), GlyGly (K) and LeuArgGlyGly (K) [SEQ ID NO:4] as variable modifications, after which spectra were manually validated.

His-Ubiquitin Pull-Down

293 FLIP-IN cells stably expressing $His_6$-Ub were transfected with the indicated siRNA and treated with doxycycline (DOX) for 24 h to induce $His_6$-Ub expression. Cells were pre-treated with 10 mM N-ethylmaleimide for 30 min and lysed in denaturing lysis buffer (6 M guanidinium-HCl, 0.1 M $Na_2HPO_4$/$NaH_2PO_4$, 10 mM Tris-HCl, 5 mM imidazole, 0.01 M β-mercaptoethanol, complete protease inhibitor cocktail). Lysates were sonicated on ice twice for 10 sec with 1 min break and centrifuged at 15 000 g for 10 min at 4° C. The supernatant was incubated with Ni-NTA-agarose beads (Qiagen) for 4 h at 4° C. Beads were collected by centrifugation, washed once with denaturing lysis buffer, once with wash buffer (8 M Urea, 0.1 M $Na_2HPO_4$/$NaH_2PO_4$, 10 mM Tris-HCl, 5 mM imidazole, 0.01 M β-mercaptoethanol, complete protease inhibitor cocktail), and twice with wash buffer supplemented with 0.1% Triton X-100, and eluted in elution buffer (0.2 M imidazole, 0.15 M Tris-HCl, 30% glycerol, 0.72 M β-mercaptoethanol, 5% SDS) before analysis by SDS-PAGE and immunoblotting.

HR-Based Repair Assays

Parental U2OS cells and U2OS cells stably expressing wild-type CtIP or CtIP(T847E) mutant were transfected with the indicated siRNA and the PALB2-KR construct, synchronized with a single thymidine block, treated with doxycycline to induce CtIP expression and subsequently blocked in G1 phase by adding 40 µM Lovastatin. Cells were collected by trypsinization, washed once with PBS and electroporated with 2.5 µg of sgRNA plasmid and 2.5 µg of donor template using the Nucleofector technology (Lonza; protocol X-001). Cells were plated in medium supplemented with 40 µM Lovastatin and grown for 24 h before flow cytometry analysis.

PALB2 Chemical Ubiquitylation

PALB2 (1-103) polypeptides, engineered with only one cross-linkable cysteine, were ubiquitylated by cross-linking alkylation, as previously described [40, 41], with the following modifications. Purified PALB2 cysteine mutant (final concentration of 600 µM) was mixed with $His_6$-TEV-Ubiquitin G76C (350 µM) in 300 mM Tris pH 8.8, 120 mM NaCl and 5% glycerol. Tris(2-carboxyethyl)phosphine (TCEP) (Sigma-Aldrich) reducing agent was added to a final concentration of 6 mM to the mixture and incubated for 30 minutes at room temperature. The bi-reactive cysteine crosslinker, 1,3-dichloroacetone (Sigma-Aldrich), was dissolved in dimethylformamide and added to the protein mix to a final concentration of 5.25 mM. The reaction was allowed to proceed on ice for 1 h, before being quenched by the addition of 5 mM β-mercaptoethanol. $His_6$-TEV-Ubiquitin-conjugated PALB2 was enriched by passing over Ni-NTA-agarose beads (Qiagen).

The study and the results of the study are discussed below.

DNA repair by homologous recombination (HR) [1] is highly suppressed in G1 cells [2,3] to ensure that mitotic recombination occurs solely between sister chromatids [4,5]. Although many HR factors are cell cycle-regulated, the identity of the events that are both necessary and sufficient to suppress recombination in G1 cells is unknown. This study has found that the cell cycle tightly controls the interaction of BRCA1 with PALB2-BRCA2 to constrain BRCA2 function to the S/G2 phases. The BRCA1-interaction site on PALB2 is targeted by an E3 ubiquitin ligase composed of KEAP1, a PALB2-interacting protein [6], in complex with CUL3-RBX1 [7]. PALB2 ubiquitylation suppresses its interaction with BRCA1 and is counteracted by the deubiquitylase USP11, which is itself under cell cycle control. Restoration of the BRCA1-PALB2 interaction combined with the activation of DNA-end resection is sufficient to induce HR in G1, as measured by RAD51 recruitment, unscheduled DNA synthesis and a CRISPR/Cas9-based gene targeting assay. The mechanism prohibiting HR in G1 minimally consists of the suppression of DNA-end resection coupled with a multi-step block of the recruitment of BRCA2 to DNA damage sites that involves the inhibition of BRCA1-PALB2-BRCA2 complex assembly. The ability to induce HR in G1 cells with defined factors may be used in gene targeting applications in non-dividing cells.

The breast and ovarian tumour suppressors BRCA1, PALB2 and BRCA2 promote DNA double-strand break (DSB) repair by HR [8-10]. BRCA1 promotes DNA-end resection to produce the single-stranded (ss) DNA necessary for homology search and strand invasion [1], and it interacts with PALB2 [13-15] to direct the recruitment of BRCA2 [13] and RAD51 [16, 17] to DSB sites. The accumulation of BRCA1 on the chromatin that flanks DSB sites is suppressed in G1 cells [18], reminiscent of the potent inhibition of HR in this phase of the cell cycle. Since the inhibition of BRCA1 recruitment in G1 is dependent on the 53BP1 and RIF1 proteins [18, 19], two inhibitors of end-resection [18-22], this regulation of BRCA1 was originally viewed in light of its function in stimulating DNA-end processing.

Figure 1C:
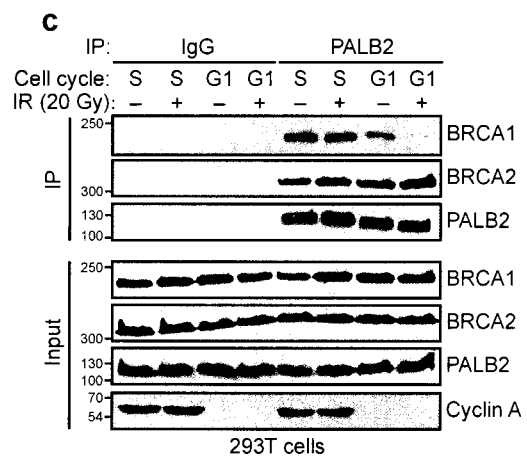

However, as BRCA1 is also involved in promoting the recruitment of BRCA2 through its interaction with PALB2 [13-15], this study investigated whether inducing BRCA1 recruitment to DSB sites in G1, through mutation of 53BP1 (also known as TP53BP1) by genome editing (53BP1Δ; FIG. 5a-c) also resulted in BRCA2 accumulation into ionizing radiation (IR)-induced foci. In contrast with BRCA1, neither BRCA2 nor PALB2 are recruited to G1 DSB sites in U-2-OS (U2OS) cells lacking 53BP1 at IR doses ranging from 2 to 20 Gy (Figure 1ab and FIG. 5d,e). Since BRCA1 and PALB2 interact directly [13,14], this result suggested that G1 cells may block BRCA2 recruitment by suppressing the BRCA1-PALB2 interaction. Indeed, while PALB2 interacts with BRCA2 irrespective of cell cycle position, it interacts efficiently with BRCA1 only during S phase (FIG. 1c). The presence of DNA damage led to the loss of the residual PALB2-BRCA1 interaction in G1 whereas it had little impact on the assembly of the BRCA1-PALB2-BRCA2 complex in S phase (FIG. 1c). Since all proteins were expressed in G1 (FIG. 1c), the results suggest that the assembly of the BRCA1-PALB2-BRCA2 complex is controlled during the cell cycle, possibly to restrict the accumulation of BRCA2 at DSB sites to the S/G2 phases.

Figures 6E, 6F:
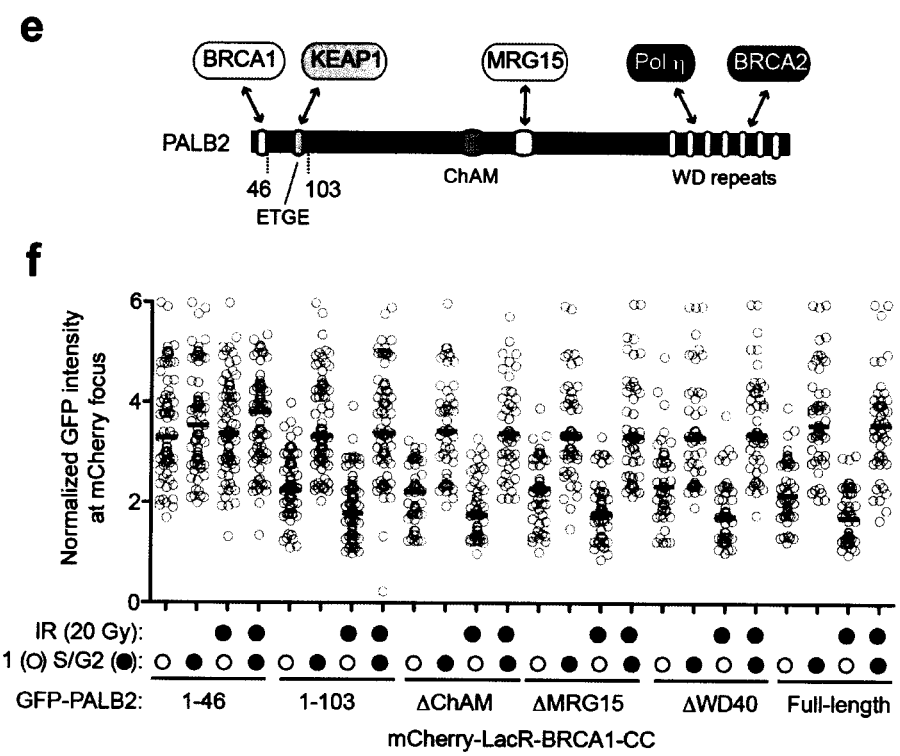
FIG. 6. The BRCA1-PALB2 interaction is cell cycle regulated. a, Schematic of the LacO/LacR chromatin-targeting system. b, U2OS 256 cells were transfected with the indicated mCherry-LacR and GFP-fusions. GFP fluorescence was measured at the site of the lacO array-localized mCherry focus. Each circle represents one cell analyzed and the bar is at the median. Cells were also stained with a cyclin A antibody to determine cell cycle position (N=3). IR, Ionizing radiation. c, Representative micrographs of U2OS 256 cells transfected with the indicated mCherry-LacR and GFP-fusions; data is quantified in d. d, Quantification of U2OS 256 cells transfected with the indicated mCherry-LacR and GFP-fusions to tether either BRCA1 or PALB2 to the lacO array (N=3). e, Schematic representation of PALB2 architecture and its major interacting proteins. f, Quantification of U2OS 256 cells transfected with the indicated GFP-PALB2 mutants and mCherry-LacR-BRCA1-CC. Cells were also stained with a cyclin A antibody to determine cell cycle position (N=3).

These results were confirmed using a single-cell assay assessing the co-localization, at an integrated LacO array [23], of a mCherry-tagged LacR-BRCA1 fusion protein with GFP-tagged PALB2 (FIG. 6a). This LacR/LacO system recapitulated the cell cycle-dependent and DNA damage-sensitive BRCA1-PALB2 interaction (FIG. 6b) and enabled the finding that sequences on PALB2, located outside its amino-terminal BRCA1-interaction domain (residues 1-50) were responsible for the cell cycle-dependent regulation of its association with BRCA1 (FIG. 6c,d). Further deletion mutagenesis identified a single region, encompassed within residues 46-103 in PALB2 (FIG. 6e,f) responsible for the cell cycle-dependent regulation of the BRCA1-PALB2 interaction. This region corresponds to the interaction site for KEAP1 [6], identifying this protein as a candidate regulator of the BRCA1-PALB2 interaction.

Figure 1D:
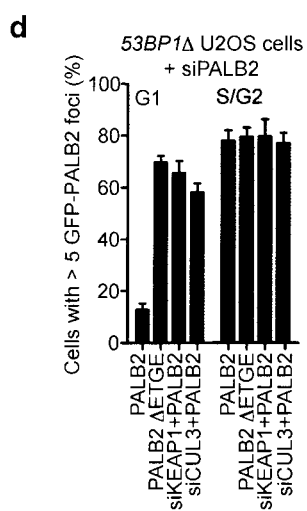
Figure 1E:
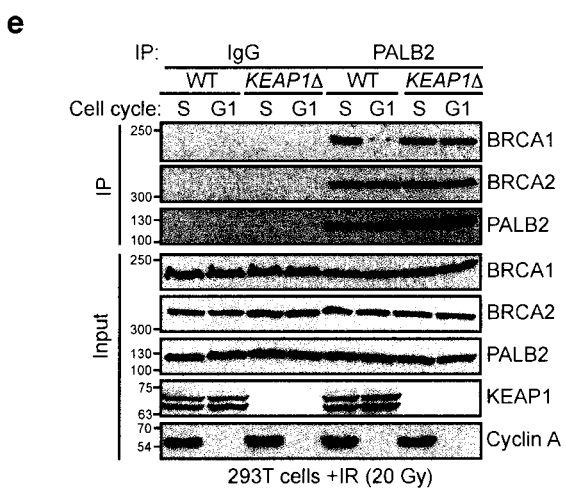

KEAP1 is a substrate adaptor for a CULLIN 3-RING ubiquitin (Ub) ligase (CRL3) that targets the antioxidant regulator NRF2 for proteasomal degradation [24] and recognizes an "ETGE" motif on both PALB2 and NRF2 through its KELCH domain [6]. Depletion of KEAP1 from 53BP1Δ cells, or deletion of the ETGE motif in full-length PALB2 (PALB2 ΔETGE) induced PALB2 IR-induced focus formation in G1 cells (FIG. 1d and FIG. 7a). Furthermore, in cells in which KEAP1 was inactivated by genome editing (KEAP1Δ, FIG. 7b) a stable BRCA1-PALB2-BRCA2 complex was detected in both G1 and S phases (FIG. 1e). KEAP1 is therefore an inhibitor of the BRCA1-PALB2 interaction.

CUL3 also interacts with PALB2 (FIG. 7c) and its depletion in 53BP1Δ U2OS cells de-repressed PALB2 IR-induced foci in G1 (FIG. 1d and FIG. 7a). Furthermore, in G1-synchronized KEAP1Δ cells, expression of a CUL3-binding deficient KEAP1 protein that lacks its BTB domain (ΔBTB) failed to suppress the BRCA1-PALB2 interaction, unlike its wild type counterpart (FIG. 7d). These results suggest that KEAP1 recruits CUL3 to PALB2 to suppress its interaction with BRCA1.

Figures 2A, 2B:
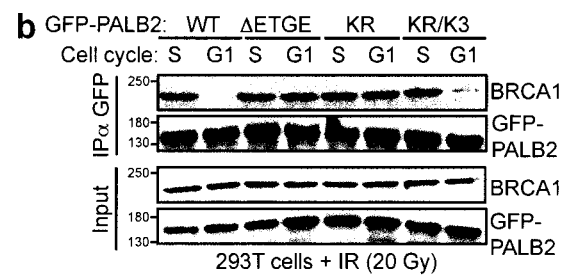
FIG. 2. Ubiquitylation of PALB2 prevents BRCA1-PALB2 interaction. a, Sequence of the PALB2 N terminus and mutants. [SEQ ID NOs: 1-3] b, GFP immunoprecipitation (IP) of extracts derived from G1- or S-phase synchronized 293T cells expressing the indicated GFP-PALB2 proteins. c, In vitro ubiquitylation of the indicated HA-tagged PALB2 proteins by CRL3-KEAP1. d, Pulldown assay of ubiquitylated HA-PALB2 (1-103) incubated with MBP or MBP-BRCA1-CC. I, input; FT, flow-through; PD, pulldown. The asterisk denotes a fragment of HA-PALB2 competent for BRCA1 binding. b-d, Numbers on left indicate kDa.

Using the LacR/LacO system and co-immunoprecipitation assays, a mutant of PALB2 lacking all 8 lysine residues in the BRCA1-interaction domain (PALB2-KR; FIG. 2a) was found to interact with BRCA1 irrespective of cell cycle position (FIG. 2b and FIG. 7e,f). Further mutagenesis identified residues 20, 25 and 30 in PALB2 as critical for the suppression of the BRCA1-PALB2 interaction since reintroduction of these lysines in the context of PALB2-KR (yielding PALB2-KR/K3; FIG. 2a) led to the suppression of BRCA1-PALB2-BRCA2 complex assembly in G1 cells (FIG. 2b and FIG. 7e). Together, these results suggested a model whereby PALB2-bound KEAP1 forms an active CRL3 complex that ubiquitylates the PALB2 N-terminus to suppress its interaction with BRCA1.

While PALB2 ubiquitylation can be detected in cells (FIG. 8a), the lysine-rich nature of the PALB2 N-terminus has so far precluded unambiguously mapping in vivo ubiquitylation sites on Lys 20, 25 or 30. However, ubiquitylation could be detected on Lys16 and Lys43 by mass spectrometry, indicating that the PALB2 N-terminus is ubiquitylated (FIG. 8b). In a complementary set of experiments, PALB2 targeted to the LacO array induced immunoreactivity to conjugated ubiquitin (FIG. 8c-e). Ub co-localization with PALB2 was highest in G1, and depended on the KEAP1-interaction motif and the presence of the Lys 20/25/30 residues (FIG. 8d-e), consistent with a model that PALB2 is ubiquitylated on those sites in G1 cells. Indeed, ubiquitylation of the N-terminus of PALB2 (residues 1-103; fused to a haemagglutinin (HA) epitope tag) could be readily reconstituted by recombinant CRL3-KEAP1, in a manner that depended on the KEAP1-interaction domain of PALB2 (FIG. 2c) and Lys25 and Lys30 were unambiguously identified as being ubiquitylated by KEAP1 in vitro by mass spectrometry.

Ubiquitylation of PALB2 by CRL3-KEAP1 inhibited its interaction with a BRCA1 fragment comprising residues 1363-1437 (BRCA1-CC), an inhibition that was more obvious with the highly modified forms of PALB2 due to the presence of ubiquitylated lysines outside the BRCA1-interaction domain (FIG. 2d). In order to specifically test whether ubiquitylation of a single lysine residue of the three identified as critical inhibited the interaction with BRCA1, chemical crosslinking was used to install a single ubiquitin moiety at position 20 or 45 (yielding PALB2-$K_C$20-Ub and PALB2-$K_C$45-Ub). Ubiquitylation of PALB2 at position 20 completely suppressed its interaction with BRCA1 whereas modification of residue 45 had no impact on the interaction (FIG. 9a), echoing the in vivo data (FIG. 7e). Together, these results indicate that ubiquitylation of PALB2 at specific sites on its N-terminus prevents its interaction with BRCA1.

Since neither the activity of the CRL3-KEAP1 E3 ligase (FIG. 9b) nor the interaction of CRL3-KEAP1 with PALB2 (FIG. 7c) are regulated by the cell cycle, it was possible that eubiquitylation of PALB2 might be regulated in a cell cycle-dependent manner. KEAP1 physically interacts with USP11 [25], a deubiquitylase that also interacts with BRCA2 [26] and PALB2 (FIG. 9c). USP11 depletion impairs gene conversion [27] (FIG. 9d) and results in hypersensitivity to PARP inhibition [27] identifying it as an HR regulator of unknown function. Co-immunoprecipitation experiments confirmed that USP11 and its catalytic activity were necessary for the formation of a stable BRCA1-PALB2-BRCA2 complex, especially in the presence of DNA damage (FIG. 3a and FIG. 9e,f).

If USP11 antagonizes PALB2 ubiquitylation by CRL3-KEAP1, then removal of KEAP1 (or CUL3) should reverse the phenotypes imparted by loss of USP11. Indeed, deletion of KEAP1 restored resistance to PARP inhibitors (PARPi) and the BRCA1-PALB2 interaction in USP11 knockout cells prepared by genome editing (USP11Δ) (FIG. 3b,c and FIG. 9e). Likewise, depletion of CUL3 or KEAP1 reversed the gene conversion defect of USP11-depleted cells (FIG. 10a). Introduction of the PALB2-KR mutant restored its interaction with BRCA1 and reversed PARPi sensitivity in USP11Δ cells in a manner that depended on Lys20/25/30 (FIG. 10b,c). Since recombinant USP11 can directly de-ubiquitylate PALB2 (1-103) (FIG. 3d), these results suggest that USP11 promotes the assembly of the BRCA1-PALB2-BRCA2 complex by reversing the inhibitory ubiquitylation on the PALB2 Lys20/25/30 residues.

Figure 11A:
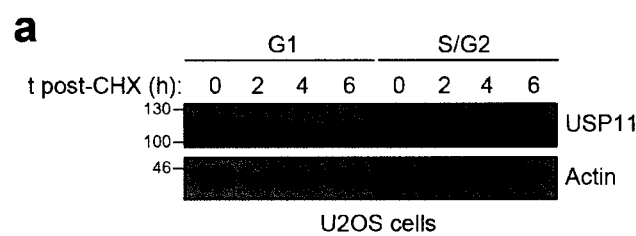
FIG. 11. Characterization of USP11 protein stability a, U2OS cells synchronized in G1 or S/G2 were treated with cyclohexamide (CHX) and processed at the indicated time points to monitor USP11 stability. b, Immunoprecipitation (IP) of PALB2 from extracts prepared from 293T cells that were synchronized in G1 or S phase and treated or not with IR (20 Gy). c, U2OS cells were irradiated with a dose of 2 or 20 Gy and processed for USP11 immunoblotting at the indicated times post-IR. Actin was used as a loading control. d, U2OS cells, mock-treated or incubated with the ATM inhibitor KU55933 (ATMi), ATR inhibitor VE-821 (ATRi) or DNA-PKcs inhibitor NU7441 (DNAPKi), were irradiated (20 Gy) and processed for USP11 and actin (loading control) immunoblotting. e, Similar experiment to d except that cells were exposed to ultraviolet (UV) radiation (50 mJ/cm$^{-2}$). f, U2OS cells, mock-treated or incubated with the proteasome inhibitor MG132, were irradiated (20 Gy) and processed for USP11 and actin (loading control) immunoblotting. g, U2OS cells, mock-treated or incubated with the Cullin inhibitor MLN4924, were irradiated (20 Gy) and processed for USP11 and actin (loading control) immunoblotting.
Figure 11B:
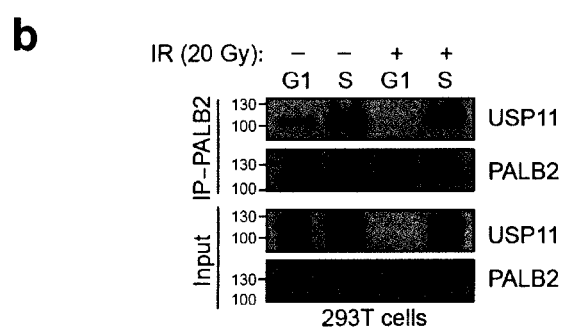
Figure 11C:
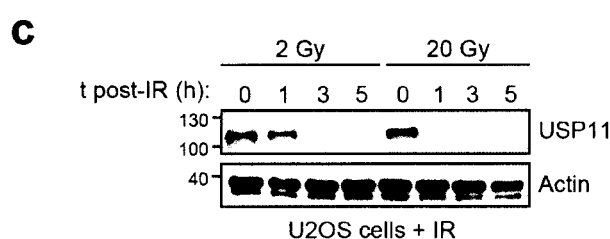
Figure 11D:
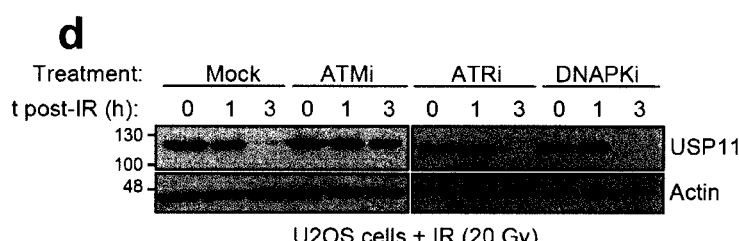
Figure 11E:
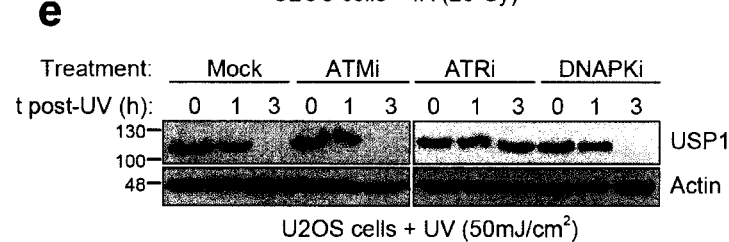
Figure 11F:
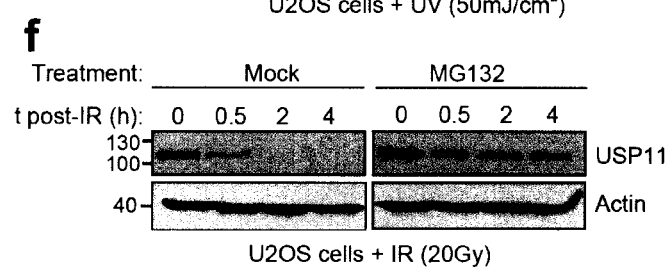
Figure 11G:
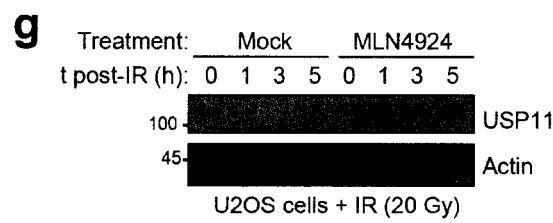

It was observed that USP11 turns over rapidly in G1 cells and interacts poorly with PALB2 in this phase of the cell cycle (FIG. 11a,b). Furthermore, there is a rapid loss of USP11 upon DNA damage induction, specifically in G1 phase (FIG. 3e and FIG. 11b,c). The destabilization of USP11 following IR treatment is dependent on ATM signalling, whereas it is ATR-dependent following UV irradiation (FIG. 11d,e). The drop in USP11 steady-state levels in G1 is the result of proteasomal degradation (FIG. 11f). A CRL4 E3 Ub ligase is most likely responsible for controlling the stability of USP11 as treatment with MLN4924, a pan-CRL inhibitor [28] (FIG. 11g), or depletion of CUL4 (FIG. 3f) protected USP11 from DNA damage-induced degradation. CUL4 depletion led to BRCA2 and PALB2 IR-induced focus formation in G1 53BP1Δ cells (FIG. 3g and FIG. 12a), consistent with the regulation of USP11 by a CRL4 complex acting as the upstream signal that ultimately controls BRCA1-PALB2-BRCA2 complex assembly.

Figure 4A:
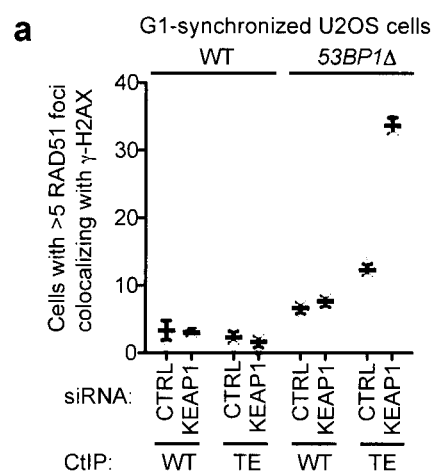
FIG. 4. Reactivation of HR in G1 phase. a, Quantitation of wild-type (WT) and 53BP1Δ U2OS cells co-transfected with non-targeting (CTRL) or KEAP1 siRNAs and vectors expressing wild-type CtIP or the T847E (TE) mutant that were synchronized in G1, irradiated (2 Gy) and processed for γ-H2AX and RAD51 immunofluorescence (mean±s.d., N=3). b, Representative micrographs from a. IR, ionizing radiation. c, Schematic of the gene-targeting assay. d, Gene-targeting efficiency at the LMNA locus in asynchronously dividing (ASN) and G1-arrested U2OS cells (mean±s.d., N=3). HR, homologous recombination; sgRNA, single guide RNA. e, Gene targeting at the LMNA locus in G1-arrested cells transfected with the indicated siRNA or a PALB2-KR expression vector (mean±s.d., N=3). f, Model of the cell-cycle regulation of homologous recombination.
Figure 4B:
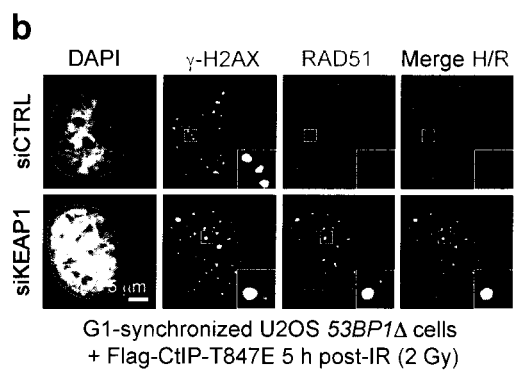

While deletion of 53BP1 produces low levels of ssDNA in G1 cells [29], combining the 53BP1Δ mutation with depletion of KEAP1 did not produce extraction-resistant RAD51 IR induced foci, suggesting little-to-no RAD51 nucleofilament formation (FIG. 12b). ssDNA formation remained insufficient in those cells and thus took advantage of the phosphomimetic T847E mutant of CtIP that promotes resection in G1 cells [30]. Unlike wild type CtIP, introduction of CtIP-T847E into 53BP1Δ cells depleted of KEAP1 induced RAD51 IR-induced focus formation in G1 cells (FIG. 4a,b and FIG. 12b,c) along with unscheduled DNA synthesis (FIG. 12d). These results suggested that the steps downstream of RAD51 nucleofilament formation, i.e. strand invasion, D-loop formation and DNA synthesis, could be activated in G1.

To test whether productive HR could also be activated in G1 a CRISPR/Cas9-stimulated gene targeting assay (Pinder J. et al, Nuclei Acids Res. 43, 9379-9392, 2015) was employed in which the insertion of the coding sequence for the mClover fluorescent protein at the 5' of the lamin A (LMNA) or PML genes was monitored by microscopy or flow cytometry (FIG. 4c and FIG. 12e,f), with the latter method enabling the gating of cells with a defined DNA content (such as G1 cells). Synchronization protocols were also established in which G1 cells obtained after release from a thymidine block were arrested in G1 by lovastatin treatment [2] for 24 h (FIG. 12g,h). Using this system, a concentration of donor template in the linear range of the assay was determined, and it was ascertained that gene targeting at the LMNA locus was dependent on BRCA1-PALB2-BRCA2 complex assembly (FIG. 13a,b). It was also confirmed that gene targeting by HR was highly suppressed in G1 (FIG. 4d).

The combined activation of resection and BRCA1 recruitment to DSB sites (i.e. in 53BP1Δ cells expressing CtIP (T847E) was insufficient to stimulate gene targeting at either the LMNA or the PML locus in G1 cells (FIG. 4e and FIG. 13c). However, when the BRCA1-PALB2 interaction was restored in resection-competent G1 cells using either KEAP1 depletion or expression of the PALB2-KR mutant, a robust increase in gene targeting events at both loci was detected (FIG. 4e and FIG. 13c). However, the gene-targeting frequencies of G1 cells remained lower than those of asynchronously dividing cells, suggesting an incomplete activation of HR. 53BP1 inactivation and the expression of CtIP(T847E) were both necessary for G1 HR (FIG. 13d,e), indicating that the simultaneous activation of end resection and BRCA2 recruitment to DSB sites were both necessary and sufficient to activate unscheduled recombination in this phase of the cell cycle.

In conclusion, the regulation of BRCA1-PALB2-BRCA2 complex assembly is a key node in the cell cycle control of DSB repair by HR. This regulation converges on the BRCA1-interaction site on PALB2 and is enforced by the opposing activities of the E3 ligase CRL3-KEAP1 and the deubiquitylase USP11, with the latter being antagonized in G1 by a CRL4 complex (FIG. 4D. In this model, the stabilization of USP11 in S phase licenses the recruitment of PALB2-BRCA2 and the subsequent loading of RAD51 at DSB sites. The studies also demonstrate that the suppression of HR in G1 cells is largely reversible and that it involves the combined suppression of end resection and BRCA2 recruitment to DSB sites (FIG. 4D. As most cells in the human body are not actively cycling and are thus refractory to HR, the manipulations described herein give rise to the development of genome editing methods that enable therapeutic gene targeting in a wider variety of tissues.

Example 2

Identification of DCAF10 as a Substrate Adaptor for the Degradation of USP11.

CUL4-RING-Ligase (CRL4) complexes are composed of CULLIN4 (CUL4), RBX1, DDB1, DDA1 and a substrate adaptor called a DCAF [42]. To search for the substrate adaptor that mediates the ubiquitylation of USP11, a focused siRNA library was assembled that depletes known and predicted DCAFs along with other CUL4-interacting proteins. This library was screened in a high content microscopy assay where USP11 levels were evaluated by immunofluorescence microscopy. Cells were treated either with ultraviolet light (UV) or ionizing radiation (IR) to induce USP11 degradation. Data was normalized to the non-irradiated condition and the mean of two independent experiments was used to plot values after UV- and IR-treatment. The data, shown in FIG. 14a shows that in addition to the expected stabilization of USP11 after CUL4 depletion, the depletion of DCAF10, DCA F15 and DCAF17 also led to USP11 stabilization. Since siRNA-mediated knockdown is prone to off-target effects, it was then assessed whether the knockdown of DCAF10, DCAF15 or DCAF17 by two independent siRNAs could stabilize USP11 in immunoblotting experiments. It was found that while stabilization of USP11 could only be observed with a single siRNA (FIG. 14b), depletion of DCAF10 with both siRNAs led to a robust stabilization of USP11 (FIG. 14b). Since CRL4 substrate adaptors bind to their substrates [42], it was next assessed whether DCAF10 or DCAF15 could interact with USP11 in co-immunoprecipitation assays. It was found that when Flag-tagged USP11 was immunoprecipitated from HEK293 cell extracts, it interacted with DCAF10 but not DCAF15 (FIG. 15a), strongly suggesting that DCAF10 is a bona fide substrate adaptor that targets USP11 for degradation. To further assess whether DCAF10 is indeed involved in the regulation of USP11, mouse embryo fibroblasts (MEFs) were generated from congenic wild type (Dcaf10$^{+/+}$), heterozygote (Dcaf10$^{+/+}$) and Dcaf10$^{-/-}$ mice and immunoblotted for USP11. Loss of DCAF10 resulted in higher steady-state levels of USP11 in mouse cells (FIG. 15b), consistent with DCAF10 being the adaptor of a CRL4 complex targeting USP11. Finally, it was assessed whether DCAF10 over-expression can suppress homologous recombination in a dominant manner using the direct repeat (DR)-GFP assay [43]. Overexpression of DCAF10, but not of DCAF15 led to a decrease in HR in the same magnitude as the depletion of USP11 and other core HR factors (FIG. 15c). Collectively, these data suggest that DCAF10 regulates HR through the control of USP11.

Example 3

A Genetically-Encoded Inhibitor of KEAP1 can Promote Homologous Recombination in G1 Cells.

Figure 16:
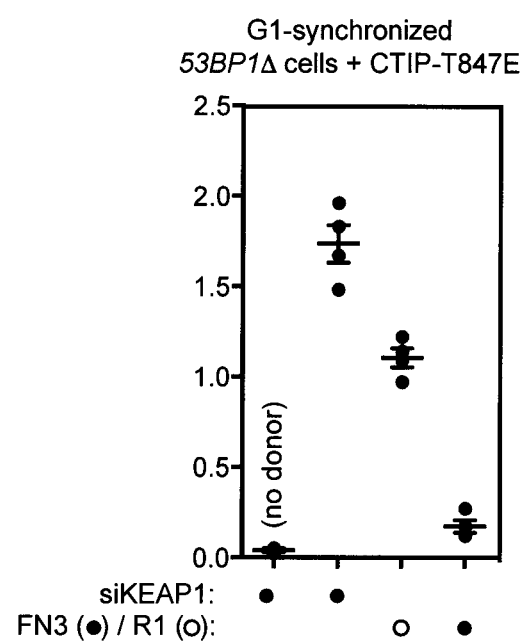
FIG. 16. KEAP1 inhibition can activate HR in G1 cells. Gene targeting at the LMNA locus in G1-arrested cells transfected with the indicated siRNA and vectors expressing either the R1 KEAP1 inhibitor or its FN3 scaffold control (mean±s.d., N=3).

The activation of gene targeting in G1 cells requires the removal of 53BP1, the introduction of CtIP-T847E and the interaction between PALB2 and BRCA1, which can be achieved by the removal of KEAP1. To develop a system that would enable activation of HR in G1 and non-dividing cells, it was determined whether KEAP1 siRNAs could be replaced with inhibitors of KEAP1. A recently described high-affinity genetically encoded inhibitor of KEAP1, named R1, which is based on fibronectin-3 (FN3) scaffold was selected [44]. The LMNA gene targeting assay [45] was carried out in 53BP1Δ U2OS cells synchronized in G1 phase and it was found that transfection of the R1 KEAP1 inhibitor, but not its FN3 control, led to a robust activation of gene-targeting, albeit less, and KEAP1 depletion (FIG. 16). Inhibition of KEAP1 can be a propitious route for the activation of HR in non-dividing cells.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methodologies, reagents, etc. which are reported therein which might be used in connection with the invention. Nothing herein is to be construed as an admission that the invention is not entitled to antedate such disclosure by virtue of prior invention.

TABLE 1

| Protein | NCBI Accession No. | SEQ ID NO. |
| --- | --- | --- |
| USP11 (ubiquitin carboxyl-terminal hydrolase 11) | NP_004642.2 | 5 |
| PALB2 (partner and localizer of BRCA2) | NP_078951.2 | 6 |
| BRCA1 (*Homo sapiens* breast cancer 1) | NG_005905.2 | 7 |
| BRCA2 (*Homo sapiens* breast cancer 2) | NG_012772.3 | 8 |
| KEAP1 (kelch-like ECH-associated protein 1) | NP_036421.2 | 9 |
| 53BP1 (tumor suppressor p53-binding protein 1 isoform 1) | NP_001135452.1 | 10 |
| 53BP1 (tumor suppressor p53-binding protein 1 isoform 2) | NP_001135451.1 | 11 |
| 53BP1 (tumor suppressor p53-binding protein 1 isoform 3) | NP_005648.1 | 12 |
| DCAF10 (DDB1- and CUL4-associated factor 10 isoform a) | NP_077321.3 | 13 |
| DCAF (DDB1- and CUL4-associated factor 10 isoform b) | NP_001273739.1 | 14 |
| RBX1(E3 ubiquitin-protein ligase RBX1) | NP_055063.1 | 15 |
| CUL3 (*Homo sapiens* cullin 3) | NG_032169.1 | 16 |
| CtIP/RBBP8 (*Homo sapiens* retinoblastoma binding protein 8) | NG_012121.1 | 17 |

FULL CITATIONS FOR PUBLICATIONS

1. Jasin, M. & Rothstein, R. Repair of strand breaks by homologous recombination. *Cold Spring Harb Perspect Biol* 5, a012740, doi:10.1101/cshperspect.a012740 (2013).
2. Hartlerode, A., Odate, S., Shim, I., Brown, J. & Scully, R. Cell cycle-dependent induction of homologous recombination by a tightly regulated I-SceI fusion protein. *PLoS One* 6, e16501, doi:10.1371/journal.pone.0016501 (2011).
3. Rothkamm, K., Kruger, I., Thompson, L. H. & Lobrich, M. Pathways of DNA doublestrand break repair during the mammalian cell cycle. *Mol Cell Biol* 23, 5706-5715 (2003).
4. Kasparek, T. R. & Humphrey, T. C. DNA double-strand break repair pathways, chromosomal rearrangements and cancer. *Semin Cell Dev Biol* 22, 886-897, doi:10.1016/j.semcdb.2011.10.007 (2011).
5. Panier, S. & Durocher, D. Push back to respond better: regulatory inhibition of the DNA double-strand break response. *Nature reviews. Molecular cell biology*, doi:10.1038/nrm3659 (2013).
6. Ma, J. et al. PALB2 interacts with KEAP1 to promote NRF2 nuclear accumulation and function. *Mol Cell Biol* 32, 1506-1517, doi:10.1128/MCB.06271-11 (2012).
7. Genschik, P., Sumara, I. & Lechner, E. The emerging family of CULLIN3-RING ubiquitin ligases (CRL3s): cellular functions and disease implications. *EMBO J* 32, 2307-2320, doi:10.1038/emboj.2013.173 (2013).
8. Roy, R., Chun, J. & Powell, S. N. BRCA1 and BRCA2: different roles in a common pathway of genome protection. *Nat Rev Cancer* 12, 68-78, doi:10.1038/nrc3181 nrc3181 [pii] (2011).
9. Li, M. L. & Greenberg, R. A. Links between genome integrity and BRCA1 tumor suppression. *Trends Biochem Sci*, doi:S0968-0004(12)00092-8 [pii] 10.1016/j.tibs.2012.06.007 (2012).
10. Park, J. Y., Zhang, F. & Andreassen, P. R. PALB2: The hub of a network of tumor suppressors involved in DNA damage responses. *Biochim Biophys Acta* 1846, 263-275, doi:10.1016/j.bbcan.2014.06.003 (2014).
11. Schlegel, B. P., Jodelka, F. M. & Nunez, R. BRCA1 promotes induction of ssDNA by ionizing radiation. *Cancer Res* 66, 5181-5189, doi: 66/10/5181 [pii] 10.1158/0008-5472.CAN-05-3209 (2006).
12. Stark, J. M., Pierce, A. J., Oh, J., Pastink, A. & Jasin, M. Genetic steps of mammalian homologous repair with distinct mutagenic consequences. *Mol Cell Biol* 24, 9305-9316, doi:24/21/9305 [pii] 10.1128/MCB.24.21.9305-9316.2004 (2004).
13. Zhang, F. et al. PALB2 links BRCA1 and BRCA2 in the DNA-damage response. *Curr Biol* 19, 524-529, doi: S0960-9822(09)00723-4 [pii] 10.1016/j.cub.2009.02.018 (2009).
14. Sy, S. M., Huen, M. S. & Chen, J. PALB2 is an integral component of the BRCA complex required for homologous recombination repair. *P Natl Acad Sci USA* 106, 7155-7160, doi:10.1073/pnas.0811159106 (2009).
15. Simhadri, S. et al. Male Fertility Defect Associated with Disrupted BRCA1-PALB2 Interaction in Mice. *J Biol Chem* 289, 24617-24629, doi:10.1074/jbc.M114.566141 (2014).
16. Bhattacharyya, A., Ear, U. S., Koller, B. H., Weichselbaum, R. R. & Bishop, D. K. The breast cancer susceptibility gene BRCA1 is required for subnuclear assembly of Rad51 and survival following treatment with the DNA cross-linking agent cisplatin. *J Biol Chem* 275, 23899-23903, doi:10.1074/jbc.0000276200 [pii] (2000).
17. Zhang, F., Bick, G., Park, J. Y. & Andreassen, P. R. MDC1 and RNF8 function in a pathway that directs BRCA1-dependent localization of PALB2 required for homologous recombination. *J Cell Sci* 125, 6049-6057, doi:10.1242/jcs.111872 (2012).
18. Escribano-Diaz, C. et al. A Cell Cycle-Dependent Regulatory Circuit Composed of 53BP1-RIF1 and BRCA1-CtIP Controls DNA Repair Pathway Choice. *Molecular cell* 49, 872-883, doi:10.1016/j.molce1.2013.01.001 (2013).
19. Feng, L., Fong, K. W., Wang, J., Wang, W. & Chen, J. RIF1 counteracts BRCA1-mediated end resection during DNA repair. The Journal of biological chemistry 288, 11135-11143, doi:10.1074/jbc.M113.457440 (2013).
20. Chapman, J. R. et al. RIF1 Is Essential for 53BP1-Dependent Nonhomologous End Joining and Suppression of DNA Double-Strand Break Resection. *Mol Cell*, doi: S1097-2765(13)00003-8 [pii] 10.1016/j.molce1.2013.01.002 (2013).
21. Bunting, S. F. et al. 53BP1 inhibits homologous recombination in Brca1-deficient cells by blocking resection of DNA breaks. Cell 141, 243-254, doi:S0092-8674(10) 00285-0[pii] 10.1016/j.cell.2010.03.012 (2010).
22. Zimmermann, M., Lottersberger, F., Buonomo, S. B., Sfeir, A. & de Lange, T. 53BP1Regulates DSB Repair Using Rifl to Control 5' End Resection. Science, doi: science.1231573 [pii]10.1126/science.1231573 (2013).
23. Tang, J. et al. Acetylation limits 53BP1 association with damaged chromatin to promote homologous recombination. *Nature structural & molecular biology*, doi:10.1038/nsmb.2499 (2013).
24. Taguchi, K., Motohashi, H. & Yamamoto, M. Molecular mechanisms of the Keap1-Nrf2 pathway in stress response and cancer evolution. *Genes Cells* 16, 123-140, doi:10.1111/j.1365-2443.2010.01473.x (2011).
25. Sowa, M. E., Bennett, E. J., Gygi, S. P. & Harper, J. W. Defining the human deubiquitinating enzyme interaction landscape. *Cell* 138, 389-403, doi:10.1016/j.cell.2009.04.042 (2009).
26. Schoenfeld, A. R., Apgar, S., Dolios, G., Wang, R. & Aaronson, S. A. BRCA2 is ubiquitinated in vivo and interacts with USP11, a deubiquitinating enzyme that exhibits prosurvival function in the cellular response to DNA damage. *Mol Cell Biol* 24, 7444-7455, doi:10.1128/MCB.24.17.7444-7455.2004 24/17/7444 [pii] (2004).
27. Wiltshire, T. D. et al. Sensitivity to poly(ADP-ribose) polymerase (PARP) inhibition identifies ubiquitin-specific peptidase 11 (USP11) as a regulator of DNA double-strand break repair. *J Biol Chem* 285, 14565-14571, doi:M110.104745 [pii] 10.1074/jbc.M110.104745 (2010).
28. Enchev, R. I., Schulman, B. A. & Peter, M. Protein neddylation: beyond cullin-RING ligases. *Nat Rev Mol Cell Biol* 16, 30-44, doi:10.1038/nrm3919 (2015).
29. Yamane, A. et al. RPA accumulation during class switch recombination represents 5'-3' DNA-end resection during the S-G2/M phase of the cell cycle. *Cell Rep* 3, 138-147, doi:10.1016/j.celrep.2012.12.006 (2013).
30. Huertas, P. & Jackson, S. P. Human CtIP mediates cell cycle control of DNA end resection and double strand break repair. *The Journal of biological chemistry* 284, 9558-9565, doi:10.1074/jbc.M808906200 (2009).
31. Fradet-Turcotte, A. et al. 53BP1 is a reader of the DNA-damage-induced H2A Lys 15 ubiquitin mark. *Nature* 499, 50-54, doi:10.1038/nature12318 (2013).
32. Enchev, R. I., Schreiber, A., Beuron, F. & Morris, E. P. Structural insights into the COP9 signalosome and its common architecture with the 26S proteasome lid and eIF3. Structure 18, 518-527, doi:10.1016/j.str.2010.02.008 (2010).
33. Ran, F. A. et al. Genome engineering using the CRISPR-Cas9 system. *Nat. Protocols* 8, 2281-2308, doi:10.1038/nprot.2013.143 (2013).
34. Xia, B. et al. Control of BRCA2 cellular and clinical functions by a nuclear partner, PALB2. *Mol Cell* 22, 719-729, doi:10.1016/j.molce1.2006.05.022 (2006).
35. Orthwein, A. et al. Mitosis inhibits DNA double-strand break repair to guard against telomere fusions. *Science* 344, 189-193, doi:10.1126/science.1248024 (2014).
36. Panier, S. et al. Tandem protein interaction modules organize the ubiquitin-dependent response to DNA double-strand breaks. *Molecular cell* 47, 383-395, doi: 10.1016/j.molce1.2012.05.045 (2012).
37. Juang, Y. C. et al. OTUB1 co-opts Lys48-linked ubiquitin recognition to suppress E2 enzyme function. *Mol Cell* 45, 384-397, doi:10.1016/j.molce1.2012.01.011 51097-2765(12)00077-9 [pii] (2012).
38. Cui, J. et al. Glutamine deamidation and dysfunction of ubiquitin/NEDD8 induced by abacterial effector family. *Science* 329, 1215-1218, doi:10.1126/science.1193844 (2010).
39. Hendriks, I. A., Schimmel, J., Eifler, K., Olsen, J. V. & Vertegaal, A. C. Ubiquitin-specific Protease 11 (USP11) Deubiquitinates Hybrid Small Ubiquitin-like Modifier (SUMO)-Ubiquitin Chains to Counteract RING Finger Protein 4 (RNF4). *J Biol Chem* 290, 15526-15537, doi: 10.1074/jbc.M114.618132 (2015).
40. Long, L., Furgason, M. & Yao, T. Generation of non-hydrolyzable ubiquitin-histone mimics. *Methods* 70, 134-138, doi:10.1016/j.ymeth.2014.07.006 (2014).
41. Yin, L., Krantz, B., Russell, N. S., Deshpande, S. & Wilkinson, K. D. Nonhydrolyzable diubiquitin analogues are inhibitors of ubiquitin conjugation and deconjugation. *Biochemistry* 39, 10001-10010 (2000).
42. Jackson, S., and Xiong, Y. (2009). CRL4s: the CUL4-RING E3 ubiquitin ligases. *Trends Biochem Sci* 34, 562-570.
43. Moynahan, M. E., Chiu, J. W., Koller, B. H., and Jasin, M. (1999). Brca1 controls homology-directed DNA repair. *Mol Cell* 4, 511-518.
44. Guntas, G., Lewis, S. M., Mulvaney, K. M., Cloer, E. W., Tripathy, A., Lane, T. R., Major, M. B., and Kuhlman, B. (2016). Engineering a genetically encoded competitive inhibitor of the KEAP1-NRF2 interaction via structure-based design and phage display. Protein engineering, design & selection: PEDS 29, 1-9.
45. Pinder, J., Salsman, J., and Dellaire, G. (2015). Nuclear domain 'knock-in' screen for the evaluation and identification of small molecule enhancers of CRISPR-based genome editing. Nucleic Acids Res. October 30; 43(19): 9379-92. doi: 10.1093/nar/gkv993. Epub 2015 Oct. 1.

What is claimed is:

1. An in vitro method for activating homologous recombination in a KEAP1 deficient cell in G1 phase of the cell cycle (G1) or G0 phase of the cell cycle (G0) to repair DNA double strand breaks comprising:

reconstituting or activating DNA end resection by i) inhibiting or removing 53BP1 by administering 53BP1 short interfering (si) RNA, short hairpin (sh) RNA or microRNAs (miRNAs) or administering a histone deacetylase (HDAC) inhibitor, and ii) administering a vector comprising a coding sequence for a CtIP-T847E mutant, thereby activating homologous recombination in the cell and repairing DNA double strand breaks in the cell.

2. The method of claim 1 wherein 53BP1 is inhibited by administering 53BP1 short interfering (si) RNA, short hairpin (sh) RNA or microRNAs (miRNAs).

3. The method of claim 1, wherein 53BP1 is inhibited by administering a histone deacetylase (HDAC) inhibitor.

4. The method of claim 3, wherein the HDAC inhibitor is trichostatin.

5. An in vitro method for activating homologous recombination in a cell in G1 phase of the cell cycle (G1) or G0 phase of the cell cycle (G0) to repair DNA double strand breaks comprising:

inhibiting or removing KEAP1 or CRL3-KEAP1 in the cell using siRNA, shRNA, a KEAP1 inhibitor, or a CUL3 protein; and reconstituting or activating DNA end resection by
i) inhibiting or removing 53BP1 by administering 53BP1 short interfering (si) RNA, short hairpin (sh) RNA, or microRNAs (miRNAs), or administering a histone deacetylase inhibitor, and
ii) upregulating or expressing a CtIP-T847E mutant by administering a vector comprising a coding sequence for CtIP-T847E, thereby activating homologous recombination in the cell and repairing DNA double strand breaks in the cell.

6. The method of claim 5 wherein 53BP1 is inhibited by administering 53BP1 short interfering (si) RNA, short hairpin (sh) RNA or microRNAs (miRNAs).

7. The method of claim 5, wherein 53BP1 is inhibited by administering a histone deacetylase (HDAC) inhibitor.

8. The method of claim 7, wherein the HDAC inhibitor is trichostatin.

9. The method of claim 5, wherein KEAP1 is inhibited or removed in the cell using KEAP1 siRNA and 53BP1 is inhibited or removed in the cell using 53BP1 siRNA.

10. The method of claim 1, wherein 53BP1 is inhibited or removed in the cell using 53BP1 siRNA.

* * * * *

SEQUENCE LISTING

<160> NUMBER OF SEQ ID NOS: 17

<210> SEQ ID NO 1

<211> LENGTH: 32
<212> TYPE: PRT
<213> ORGANISM: Homo sapiens

<400> SEQUENCE: 1

```
Lys Glu Lys Leu Lys Glu Lys Leu Ala Phe Leu Lys Arg Glu Tyr Ser
1               5                   10                  15
Lys Thr Leu Ala Arg Leu Gln Arg Ala Gln Arg Ala Glu Lys Ile Lys
                20                  25                  30
```

<210> SEQ ID NO 2
<211> LENGTH: 32
<212> TYPE: PRT
<213> ORGANISM: Homo sapiens

<400> SEQUENCE: 2

```
Arg Glu Arg Leu Arg Glu Arg Leu Ala Phe Leu Arg Arg Glu Tyr Ser
1               5                   10                  15
Arg Thr Leu Ala Arg Leu Gln Arg Ala Gln Arg Ala Glu Arg Ile Arg
                20                  25                  30
```

<210> SEQ ID NO 3
<211> LENGTH: 32
<212> TYPE: PRT
<213> ORGANISM: Homo sapiens

<400> SEQUENCE: 3

```
Arg Glu Arg Leu Arg Glu Lys Leu Ala Phe Leu Lys Arg Glu Tyr Ser
1               5                   10                  15
Lys Thr Leu Ala Arg Leu Gln Arg Ala Gln Arg Ala Glu Arg Ile Arg
                20                  25                  30
```

<210> SEQ ID NO 4
<211> LENGTH: 4
<212> TYPE: PRT
<213> ORGANISM: Homo sapiens

<400> SEQUENCE: 4

```
Leu Arg Gly Gly
1
```

<210> SEQ ID NO 5
<211> LENGTH: 963
<212> TYPE: PRT
<213> ORGANISM: Homo sapiens

<400> SEQUENCE: 5

```
Met Ala Val Ala Pro Arg Leu Phe Gly Gly Leu Cys Phe Arg Phe Arg
1               5                   10                  15
Asp Gln Asn Pro Glu Val Ala Val Glu Gly Arg Leu Pro Ile Ser His
                20                  25                  30
Ser Cys Val Gly Cys Arg Arg Glu Arg Thr Ala Met Ala Thr Val Ala
            35                  40                  45
Ala Asn Pro Ala Ala Ala Ala Ala Val Ala Ala Ala Ala Val
        50                  55                  60
Thr Glu Asp Arg Glu Pro Gln His Glu Glu Leu Pro Gly Leu Asp Ser
65                  70                  75                  80
Gln Trp Arg Gln Ile Glu Asn Gly Glu Ser Gly Arg Glu Arg Pro Leu
                85                  90                  95
Arg Ala Gly Glu Ser Trp Phe Leu Val Glu Lys His Trp Tyr Lys Gln
            100                 105                 110
```

```
Trp Glu Ala Tyr Val Gln Gly Gly Asp Gln Asp Ser Ser Thr Phe Pro
            115                 120                 125

Gly Cys Ile Asn Asn Ala Thr Leu Phe Gln Asp Glu Ile Asn Trp Arg
        130                 135                 140

Leu Lys Glu Gly Leu Val Glu Gly Glu Asp Tyr Val Leu Leu Pro Ala
145                 150                 155                 160

Ala Ala Trp His Tyr Leu Val Ser Trp Tyr Gly Leu Glu His Gly Gln
                165                 170                 175

Pro Pro Ile Glu Arg Lys Val Ile Glu Leu Pro Asn Ile Gln Lys Val
            180                 185                 190

Glu Val Tyr Pro Val Glu Leu Leu Val Arg His Asn Asp Leu Gly
            195                 200                 205

Lys Ser His Thr Val Gln Phe Ser His Thr Asp Ser Ile Gly Leu Val
        210                 215                 220

Leu Arg Thr Ala Arg Glu Arg Phe Leu Val Glu Pro Gln Glu Asp Thr
225                 230                 235                 240

Arg Leu Trp Ala Lys Asn Ser Glu Gly Ser Leu Asp Arg Leu Tyr Asp
                245                 250                 255

Thr His Ile Thr Val Leu Asp Ala Ala Leu Glu Thr Gly Gln Leu Ile
            260                 265                 270

Ile Met Glu Thr Arg Lys Lys Asp Gly Thr Trp Pro Ser Ala Gln Leu
        275                 280                 285

His Val Met Asn Asn Met Ser Glu Glu Asp Glu Asp Phe Lys Gly
        290                 295                 300

Gln Pro Gly Ile Cys Gly Leu Thr Asn Leu Gly Asn Thr Cys Phe Met
305                 310                 315                 320

Asn Ser Ala Leu Gln Cys Leu Ser Asn Val Pro Gln Leu Thr Glu Tyr
                325                 330                 335

Phe Leu Asn Asn Cys Tyr Leu Glu Glu Leu Asn Phe Arg Asn Pro Leu
            340                 345                 350

Gly Met Lys Gly Glu Ile Ala Glu Ala Tyr Ala Asp Leu Val Lys Gln
        355                 360                 365

Ala Trp Ser Gly His His Arg Ser Ile Val Pro His Val Phe Lys Asn
        370                 375                 380

Lys Val Gly His Phe Ala Ser Gln Phe Leu Gly Tyr Gln Gln His Asp
385                 390                 395                 400

Ser Gln Glu Leu Leu Ser Phe Leu Leu Asp Gly Leu His Glu Asp Leu
                405                 410                 415

Asn Arg Val Lys Lys Glu Tyr Val Glu Leu Cys Asp Ala Ala Gly
            420                 425                 430

Arg Pro Asp Gln Glu Val Ala Gln Glu Ala Trp Gln Asn His Lys Arg
        435                 440                 445

Arg Asn Asp Ser Val Ile Val Asp Thr Phe His Gly Leu Phe Lys Ser
450                 455                 460

Thr Leu Val Cys Pro Asp Cys Gly Asn Val Ser Val Thr Phe Asp Pro
465                 470                 475                 480

Phe Cys Tyr Leu Ser Val Pro Leu Pro Ile Ser His Lys Arg Val Leu
                485                 490                 495

Glu Val Phe Phe Ile Pro Met Asp Pro Arg Arg Lys Pro Glu Gln His
            500                 505                 510

Arg Leu Val Val Pro Lys Lys Gly Lys Ile Ser Asp Leu Cys Val Ala
        515                 520                 525
```

```
Leu Ser Lys His Thr Gly Ile Ser Pro Glu Arg Met Met Val Ala Asp
        530                 535                 540
Val Phe Ser His Arg Phe Tyr Lys Leu Tyr Gln Leu Glu Glu Pro Leu
545                 550                 555                 560
Ser Ser Ile Leu Asp Arg Asp Asp Ile Phe Val Tyr Glu Val Ser Gly
                565                 570                 575
Arg Ile Glu Ala Ile Glu Gly Ser Arg Glu Asp Ile Val Val Pro Val
            580                 585                 590
Tyr Leu Arg Glu Arg Thr Pro Ala Arg Asp Tyr Asn Asn Ser Tyr Tyr
        595                 600                 605
Gly Leu Met Leu Phe Gly His Pro Leu Leu Val Ser Val Pro Arg Asp
    610                 615                 620
Arg Phe Thr Trp Glu Gly Leu Tyr Asn Val Leu Met Tyr Arg Leu Ser
625                 630                 635                 640
Arg Tyr Val Thr Lys Pro Asn Ser Asp Asp Glu Asp Gly Asp Glu
                645                 650                 655
Lys Glu Asp Asp Glu Glu Asp Lys Asp Val Pro Gly Pro Ser Thr
                660                 665                 670
Gly Gly Ser Leu Arg Asp Pro Glu Pro Glu Gln Ala Gly Pro Ser Ser
        675                 680                 685
Gly Val Thr Asn Arg Cys Pro Phe Leu Leu Asp Asn Cys Leu Gly Thr
    690                 695                 700
Ser Gln Trp Pro Pro Arg Arg Arg Lys Gln Leu Phe Thr Leu Gln
705                 710                 715                 720
Thr Val Asn Ser Asn Gly Thr Ser Asp Arg Thr Thr Ser Pro Glu Glu
                725                 730                 735
Val His Ala Gln Pro Tyr Ile Ala Ile Asp Trp Glu Pro Glu Met Lys
            740                 745                 750
Lys Arg Tyr Tyr Asp Glu Val Glu Ala Glu Gly Tyr Val Lys His Asp
        755                 760                 765
Cys Val Gly Tyr Val Met Lys Lys Ala Pro Val Arg Leu Gln Glu Cys
770                 775                 780
Ile Glu Leu Phe Thr Thr Val Glu Thr Leu Glu Lys Glu Asn Pro Trp
785                 790                 795                 800
Tyr Cys Pro Ser Cys Lys Gln His Gln Leu Ala Thr Lys Lys Leu Asp
                805                 810                 815
Leu Trp Met Leu Pro Glu Ile Leu Ile Ile His Leu Lys Arg Phe Ser
        820                 825                 830
Tyr Thr Lys Phe Ser Arg Glu Lys Leu Asp Thr Leu Val Glu Phe Pro
        835                 840                 845
Ile Arg Asp Leu Asp Phe Ser Glu Phe Val Ile Gln Pro Gln Asn Glu
850                 855                 860
Ser Asn Pro Glu Leu Tyr Lys Tyr Asp Leu Ile Ala Val Ser Asn His
865                 870                 875                 880
Tyr Gly Gly Met Arg Asp Gly His Tyr Thr Thr Phe Ala Cys Asn Lys
                885                 890                 895
Asp Ser Gly Gln Trp His Tyr Phe Asp Asp Asn Ser Val Ser Pro Val
            900                 905                 910
Asn Glu Asn Gln Ile Glu Ser Lys Ala Ala Tyr Val Leu Phe Tyr Gln
        915                 920                 925
Arg Gln Asp Val Ala Arg Arg Leu Leu Ser Pro Ala Gly Ser Ser Gly
    930                 935                 940
Ala Pro Ala Ser Pro Ala Cys Ser Ser Pro Pro Ser Ser Glu Phe Met
```

```
945                 950                 955                 960

Asp Val Asn

<210> SEQ ID NO 6
<211> LENGTH: 1186
<212> TYPE: PRT
<213> ORGANISM: Homo sapiens

<400> SEQUENCE: 6

Met Asp Glu Pro Pro Gly Lys Pro Leu Ser Cys Glu Glu Lys Glu Lys
1               5                   10                  15

Leu Lys Glu Lys Leu Ala Phe Leu Lys Arg Glu Tyr Ser Lys Thr Leu
            20                  25                  30

Ala Arg Leu Gln Arg Ala Gln Arg Ala Glu Lys Ile Lys His Ser Ile
        35                  40                  45

Lys Lys Thr Val Glu Glu Gln Asp Cys Leu Ser Gln Gln Asp Leu Ser
    50                  55                  60

Pro Gln Leu Lys His Ser Glu Pro Lys Asn Lys Ile Cys Val Tyr Asp
65                  70                  75                  80

Lys Leu His Ile Lys Thr His Leu Asp Glu Glu Thr Gly Glu Lys Thr
                85                  90                  95

Ser Ile Thr Leu Asp Val Gly Pro Glu Ser Phe Asn Pro Gly Asp Gly
            100                 105                 110

Pro Gly Gly Leu Pro Ile Gln Arg Thr Asp Thr Gln Glu His Phe
        115                 120                 125

Pro His Arg Val Ser Asp Pro Ser Gly Glu Gln Lys Gln Lys Leu Pro
    130                 135                 140

Ser Arg Arg Lys Lys Gln Gln Lys Arg Thr Phe Ile Ser Gln Glu Arg
145                 150                 155                 160

Asp Cys Val Phe Gly Thr Asp Ser Leu Arg Leu Ser Gly Lys Arg Leu
                165                 170                 175

Lys Glu Gln Glu Glu Ile Ser Ser Lys Asn Pro Ala Arg Ser Pro Val
            180                 185                 190

Thr Glu Ile Arg Thr His Leu Leu Ser Leu Lys Ser Glu Leu Pro Asp
        195                 200                 205

Ser Pro Glu Pro Val Thr Glu Ile Asn Glu Asp Ser Val Leu Ile Pro
    210                 215                 220

Pro Thr Ala Gln Pro Glu Lys Gly Val Asp Thr Phe Leu Arg Arg Pro
225                 230                 235                 240

Asn Phe Thr Arg Ala Thr Thr Val Pro Leu Gln Thr Leu Ser Asp Ser
                245                 250                 255

Gly Ser Ser Gln His Leu Glu His Ile Pro Pro Lys Gly Ser Ser Glu
            260                 265                 270

Leu Thr Thr His Asp Leu Lys Asn Ile Arg Phe Thr Ser Pro Val Ser
        275                 280                 285

Leu Glu Ala Gln Gly Lys Lys Met Thr Val Ser Thr Asp Asn Leu Leu
    290                 295                 300

Val Asn Lys Ala Ile Ser Lys Ser Gly Gln Leu Pro Thr Ser Ser Asn
305                 310                 315                 320

Leu Glu Ala Asn Ile Ser Cys Ser Leu Asn Glu Leu Thr Tyr Asn Asn
                325                 330                 335

Leu Pro Ala Asn Glu Asn Gln Asn Leu Lys Glu Gln Asn Gln Thr Glu
            340                 345                 350

Lys Ser Leu Lys Ser Pro Ser Asp Thr Leu Asp Gly Arg Asn Glu Asn
```

```
                355                 360                 365
Leu Gln Glu Ser Glu Ile Leu Ser Gln Pro Lys Ser Leu Ser Leu Glu
    370                 375                 380
Ala Thr Ser Pro Leu Ser Ala Glu Lys His Ser Cys Thr Val Pro Glu
385                 390                 395                 400
Gly Leu Leu Phe Pro Ala Glu Tyr Tyr Val Arg Thr Thr Arg Ser Met
                405                 410                 415
Ser Asn Cys Gln Arg Lys Val Ala Val Glu Ala Ile Gln Ser His
            420                 425                 430
Leu Asp Val Lys Lys Gly Phe Lys Asn Lys Asn Lys Asp Ala Ser
        435                 440                 445
Lys Asn Leu Asn Leu Ser Asn Glu Glu Thr Asp Gln Ser Glu Ile Arg
    450                 455                 460
Met Ser Gly Thr Cys Thr Gly Gln Pro Ser Ser Arg Thr Ser Gln Lys
465                 470                 475                 480
Leu Leu Ser Leu Thr Lys Val Ser Ser Pro Ala Gly Pro Thr Glu Asp
                485                 490                 495
Asn Asp Leu Ser Arg Lys Ala Val Ala Gln Ala Pro Gly Arg Arg Tyr
            500                 505                 510
Thr Gly Lys Arg Lys Ser Ala Cys Thr Pro Ala Ser Asp His Cys Glu
        515                 520                 525
Pro Leu Leu Pro Thr Ser Leu Ser Ile Val Asn Arg Ser Lys Glu
    530                 535                 540
Glu Val Thr Ser His Lys Tyr Gln His Glu Lys Leu Phe Ile Gln Val
545                 550                 555                 560
Lys Gly Lys Lys Ser Arg His Gln Lys Glu Asp Ser Leu Ser Trp Ser
                565                 570                 575
Asn Ser Ala Tyr Leu Ser Leu Asp Asp Ala Phe Thr Ala Pro Phe
            580                 585                 590
His Arg Asp Gly Met Leu Ser Leu Lys Gln Leu Leu Ser Phe Leu Ser
        595                 600                 605
Ile Thr Asp Phe Gln Leu Pro Asp Glu Asp Phe Gly Pro Leu Lys Leu
    610                 615                 620
Glu Lys Val Lys Ser Cys Ser Glu Lys Pro Val Glu Pro Phe Glu Ser
625                 630                 635                 640
Lys Met Phe Gly Glu Arg His Leu Lys Glu Gly Ser Cys Ile Phe Pro
                645                 650                 655
Glu Glu Leu Ser Pro Lys Arg Met Asp Thr Glu Met Glu Asp Leu Glu
            660                 665                 670
Glu Asp Leu Ile Val Leu Pro Gly Lys Ser His Pro Lys Arg Pro Asn
        675                 680                 685
Ser Gln Ser Gln His Thr Lys Thr Gly Leu Ser Ser Ile Leu Leu
    690                 695                 700
Tyr Thr Pro Leu Asn Thr Val Ala Pro Asp Asp Asn Asp Arg Pro Thr
705                 710                 715                 720
Thr Asp Met Cys Ser Pro Ala Phe Pro Ile Leu Gly Thr Thr Pro Ala
                725                 730                 735
Phe Gly Pro Gln Gly Ser Tyr Glu Lys Ala Ser Thr Glu Val Ala Gly
            740                 745                 750
Arg Thr Cys Cys Thr Pro Gln Leu Ala His Leu Lys Asp Ser Val Cys
        755                 760                 765
Leu Ala Ser Asp Thr Lys Gln Phe Asp Ser Ser Gly Ser Pro Ala Lys
    770                 775                 780
```

```
Pro His Thr Thr Leu Gln Val Ser Gly Arg Gln Gly Gln Pro Thr Cys
785                 790                 795                 800

Asp Cys Asp Ser Val Pro Pro Gly Thr Pro Pro Ile Glu Ser Phe
            805                 810                 815

Thr Phe Lys Glu Asn Gln Leu Cys Arg Asn Thr Cys Gln Glu Leu His
            820                 825                 830

Lys His Ser Val Glu Gln Thr Glu Thr Ala Glu Leu Pro Ala Ser Asp
            835                 840                 845

Ser Ile Asn Pro Gly Asn Leu Gln Leu Val Ser Glu Leu Lys Asn Pro
850                 855                 860

Ser Gly Ser Cys Ser Val Asp Val Ser Ala Met Phe Trp Glu Arg Ala
865                 870                 875                 880

Gly Cys Lys Glu Pro Cys Ile Ile Thr Ala Cys Glu Asp Val Val Ser
                885                 890                 895

Leu Trp Lys Ala Leu Asp Ala Trp Gln Trp Glu Lys Leu Tyr Thr Trp
            900                 905                 910

His Phe Ala Glu Val Pro Val Leu Gln Ile Val Pro Val Pro Asp Val
            915                 920                 925

Tyr Asn Leu Val Cys Val Ala Leu Gly Asn Leu Glu Ile Arg Glu Ile
930                 935                 940

Arg Ala Leu Phe Cys Ser Ser Asp Asp Glu Ser Glu Lys Gln Val Leu
945                 950                 955                 960

Leu Lys Ser Gly Asn Ile Lys Ala Val Leu Gly Leu Thr Lys Arg Arg
                965                 970                 975

Leu Val Ser Ser Ser Gly Thr Leu Ser Asp Gln Val Glu Val Met
            980                 985                 990

Thr Phe Ala Glu Asp Gly Gly Gly Lys Glu Asn Gln Phe Leu Met Pro
            995                 1000                1005

Pro Glu Glu Thr Ile Leu Thr Phe Ala Glu Val Gln Gly Met Gln
    1010                1015                1020

Glu Ala Leu Leu Gly Thr Thr Ile Met Asn Asn Ile Val Ile Trp
    1025                1030                1035

Asn Leu Lys Thr Gly Gln Leu Leu Lys Lys Met His Ile Asp Asp
    1040                1045                1050

Ser Tyr Gln Ala Ser Val Cys His Lys Ala Tyr Ser Glu Met Gly
    1055                1060                1065

Leu Leu Phe Ile Val Leu Ser His Pro Cys Ala Lys Glu Ser Glu
    1070                1075                1080

Ser Leu Arg Ser Pro Val Phe Gln Leu Ile Val Ile Asn Pro Lys
    1085                1090                1095

Thr Thr Leu Ser Val Gly Val Met Leu Tyr Cys Leu Pro Pro Gly
    1100                1105                1110

Gln Ala Gly Arg Phe Leu Glu Gly Asp Val Lys Asp His Cys Ala
    1115                1120                1125

Ala Ala Ile Leu Thr Ser Gly Thr Ile Ala Ile Trp Asp Leu Leu
    1130                1135                1140

Leu Gly Gln Cys Thr Ala Leu Leu Pro Pro Val Ser Asp Gln His
    1145                1150                1155

Trp Ser Phe Val Lys Trp Ser Gly Thr Asp Ser His Leu Leu Ala
    1160                1165                1170

Gly Gln Lys Asp Gly Asn Ile Phe Val Tyr His Tyr Ser
    1175                1180                1185
```

<210> SEQ ID NO 7
<211> LENGTH: 1863
<212> TYPE: PRT
<213> ORGANISM: Homo sapiens

<400> SEQUENCE: 7

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380
```

```
Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
            405                 410                 415

Asn Glu Val Asp Glu Tyr Ser Gly Ser Ser Glu Lys Ile Asp Leu Leu
        420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800
```

-continued

Cys Val Ser Gln Cys Ala Ala Phe Glu Asn Pro Lys Gly Leu Ile His
            805                 810                 815

Gly Cys Ser Lys Asp Asn Arg Asn Asp Thr Glu Gly Phe Lys Tyr Pro
        820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
            885                 890                 895

Pro Lys Val Thr Phe Glu Cys Glu Gln Lys Glu Glu Asn Gln Gly Lys
        900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
            965                 970                 975

Pro Tyr Arg Ile Pro Pro Leu Phe Pro Ile Lys Ser Phe Val Lys Thr
        980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
        1010                1015                1020

Ser Thr Ile Ser Arg Asn Asn Ile Arg Glu Asn Val Phe Lys Glu
        1025                1030                1035

Ala Ser Ser Ser Asn Ile Asn Glu Val Gly Ser Ser Thr Asn Glu
        1040                1045                1050

Val Gly Ser Ser Ile Asn Glu Ile Gly Ser Ser Asp Glu Asn Ile
        1055                1060                1065

Gln Ala Glu Leu Gly Arg Asn Arg Gly Pro Lys Leu Asn Ala Met
        1070                1075                1080

Leu Arg Leu Gly Val Leu Gln Pro Glu Val Tyr Lys Gln Ser Leu
        1085                1090                1095

Pro Gly Ser Asn Cys Lys His Pro Glu Ile Lys Lys Gln Glu Tyr
        1100                1105                1110

Glu Glu Val Val Gln Thr Val Asn Thr Asp Phe Ser Pro Tyr Leu
        1115                1120                1125

Ile Ser Asp Asn Leu Glu Gln Pro Met Gly Ser Ser His Ala Ser
        1130                1135                1140

Gln Val Cys Ser Glu Thr Pro Asp Asp Leu Leu Asp Asp Gly Glu
        1145                1150                1155

Ile Lys Glu Asp Thr Ser Phe Ala Glu Asn Asp Ile Lys Glu Ser
        1160                1165                1170

Ser Ala Val Phe Ser Lys Ser Val Gln Lys Gly Glu Leu Ser Arg
        1175                1180                1185

Ser Pro Ser Pro Phe Thr His Thr His Leu Ala Gln Gly Tyr Arg
        1190                1195                1200

Arg Gly Ala Lys Lys Leu Glu Ser Ser Glu Glu Asn Leu Ser Ser

```
            1205                1210                1215

Glu Asp Glu Glu Leu Pro Cys Phe Gln His Leu Leu Phe Gly Lys
            1220                1225                1230

Val Asn Asn Ile Pro Ser Gln Ser Thr Arg His Ser Thr Val Ala
            1235                1240                1245

Thr Glu Cys Leu Ser Lys Asn Thr Glu Glu Asn Leu Leu Ser Leu
            1250                1255                1260

Lys Asn Ser Leu Asn Asp Cys Ser Asn Gln Val Ile Leu Ala Lys
            1265                1270                1275

Ala Ser Gln Glu His His Leu Ser Glu Glu Thr Lys Cys Ser Ala
            1280                1285                1290

Ser Leu Phe Ser Ser Gln Cys Ser Glu Leu Glu Asp Leu Thr Ala
            1295                1300                1305

Asn Thr Asn Thr Gln Asp Pro Phe Leu Ile Gly Ser Ser Lys Gln
            1310                1315                1320

Met Arg His Gln Ser Glu Ser Gln Gly Val Gly Leu Ser Asp Lys
            1325                1330                1335

Glu Leu Val Ser Asp Asp Glu Glu Arg Gly Thr Gly Leu Glu Glu
            1340                1345                1350

Asn Asn Gln Glu Glu Gln Ser Met Asp Ser Asn Leu Gly Glu Ala
            1355                1360                1365

Ala Ser Gly Cys Glu Ser Glu Thr Ser Val Ser Glu Asp Cys Ser
            1370                1375                1380

Gly Leu Ser Ser Gln Ser Asp Ile Leu Thr Thr Gln Gln Arg Asp
            1385                1390                1395

Thr Met Gln His Asn Leu Ile Lys Leu Gln Gln Glu Met Ala Glu
            1400                1405                1410

Leu Glu Ala Val Leu Glu Gln His Gly Ser Gln Pro Ser Asn Ser
            1415                1420                1425

Tyr Pro Ser Ile Ile Ser Asp Ser Ser Ala Leu Glu Asp Leu Arg
            1430                1435                1440

Asn Pro Glu Gln Ser Thr Ser Glu Lys Ala Val Leu Thr Ser Gln
            1445                1450                1455

Lys Ser Ser Glu Tyr Pro Ile Ser Gln Asn Pro Glu Gly Leu Ser
            1460                1465                1470

Ala Asp Lys Phe Glu Val Ser Ala Asp Ser Ser Thr Ser Lys Asn
            1475                1480                1485

Lys Glu Pro Gly Val Glu Arg Ser Ser Pro Ser Lys Cys Pro Ser
            1490                1495                1500

Leu Asp Asp Arg Trp Tyr Met His Ser Cys Ser Gly Ser Leu Gln
            1505                1510                1515

Asn Arg Asn Tyr Pro Ser Gln Glu Glu Leu Ile Lys Val Val Asp
            1520                1525                1530

Val Glu Glu Gln Gln Leu Glu Glu Ser Gly Pro His Asp Leu Thr
            1535                1540                1545

Glu Thr Ser Tyr Leu Pro Arg Gln Asp Leu Glu Gly Thr Pro Tyr
            1550                1555                1560

Leu Glu Ser Gly Ile Ser Leu Phe Ser Asp Asp Pro Glu Ser Asp
            1565                1570                1575

Pro Ser Glu Asp Arg Ala Pro Glu Ser Ala Arg Val Gly Asn Ile
            1580                1585                1590

Pro Ser Ser Thr Ser Ala Leu Lys Val Pro Gln Leu Lys Val Ala
            1595                1600                1605
```

```
Glu Ser Ala Gln Ser Pro Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650

Val Ser Gly Leu Thr Pro Glu Phe Met Leu Val Tyr Lys Phe
    1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
    1685                1690                1695

Arg Thr Leu Lys Tyr Phe Leu Gly Ile Ala Gly Gly Lys Trp Val
    1700                1705                1710

Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly
    1730                1735                1740

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860

<210> SEQ ID NO 8
<211> LENGTH: 3418
<212> TYPE: PRT
<213> ORGANISM: Homo sapiens

<400> SEQUENCE: 8

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
                20                  25                  30

Glu Glu Leu Ser Ser Glu Ala Pro Pro Tyr Asn Ser Glu Pro Ala Glu
            35                  40                  45

Glu Ser Glu His Lys Asn Asn Asn Tyr Glu Pro Asn Leu Phe Lys Thr
        50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
```

```
              100                 105                 110
Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
        130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
                180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
        210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
        290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala Asn Gln Lys Pro Phe Glu Ser Gly Ser Asp Lys Ile Ser
        370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
            405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
            435                 440                 445

Ile Ser Ser Leu Pro Lys Ser Glu Lys Pro Leu Asn Glu Glu Thr Val
        450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
        500                 505                 510

Lys Glu Thr Phe Asn Ala Ser Phe Ser Gly His Met Thr Asp Pro Asn
        515                 520                 525
```

```
Phe Lys Lys Glu Thr Glu Ala Ser Glu Ser Gly Leu Glu Ile His Thr
    530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
                580                 585                 590

Ala Ile His Asp Glu Thr Ser Tyr Lys Gly Lys Lys Ile Pro Lys Asp
            595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
                660                 665                 670

Asn Glu Thr Cys Ser Asn Asn Thr Val Ile Ser Gln Asp Leu Asp Tyr
            675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Val Leu Ala Ala
                725                 730                 735

Ala Cys His Pro Val Gln His Ser Lys Val Glu Tyr Ser Asp Thr Asp
                740                 745                 750

Phe Gln Ser Gln Lys Ser Leu Leu Tyr Asp His Glu Asn Ala Ser Thr
            755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
                820                 825                 830

Leu Leu Pro Pro Glu Lys Tyr Met Arg Val Ala Ser Pro Ser Arg Lys
            835                 840                 845

Val Gln Phe Asn Gln Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
                900                 905                 910

Asp Leu Thr Cys Val Asn Glu Pro Ile Phe Lys Asn Ser Thr Met Val
            915                 920                 925

Leu Tyr Gly Asp Thr Gly Asp Lys Gln Ala Thr Gln Val Ser Ile Lys
    930                 935                 940
```

-continued

```
Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
            965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
            995                 1000                1005

Phe Arg Thr Ala Ser Asn Lys Glu Ile Lys Leu Ser Glu His Asn
    1010                1015                1020

Ile Lys Lys Ser Lys Met Phe Phe Lys Asp Ile Glu Glu Gln Tyr
    1025                1030                1035

Pro Thr Ser Leu Ala Cys Val Glu Ile Val Asn Thr Leu Ala Leu
    1040                1045                1050

Asp Asn Gln Lys Lys Leu Ser Lys Pro Gln Ser Ile Asn Thr Val
    1055                1060                1065

Ser Ala His Leu Gln Ser Ser Val Val Val Ser Asp Cys Lys Asn
    1070                1075                1080

Ser His Ile Thr Pro Gln Met Leu Phe Ser Lys Gln Asp Phe Asn
    1085                1090                1095

Ser Asn His Asn Leu Thr Pro Ser Gln Lys Ala Glu Ile Thr Glu
    1100                1105                1110

Leu Ser Thr Ile Leu Glu Glu Ser Gly Ser Gln Phe Glu Phe Thr
    1115                1120                1125

Gln Phe Arg Lys Pro Ser Tyr Ile Leu Gln Lys Ser Thr Phe Glu
    1130                1135                1140

Val Pro Glu Asn Gln Met Thr Ile Leu Lys Thr Thr Ser Glu Glu
    1145                1150                1155

Cys Arg Asp Ala Asp Leu His Val Ile Met Asn Ala Pro Ser Ile
    1160                1165                1170

Gly Gln Val Asp Ser Ser Lys Gln Phe Glu Gly Thr Val Glu Ile
    1175                1180                1185

Lys Arg Lys Phe Ala Gly Leu Leu Lys Asn Asp Cys Asn Lys Ser
    1190                1195                1200

Ala Ser Gly Tyr Leu Thr Asp Glu Asn Glu Val Gly Phe Arg Gly
    1205                1210                1215

Phe Tyr Ser Ala His Gly Thr Lys Leu Asn Val Ser Thr Glu Ala
    1220                1225                1230

Leu Gln Lys Ala Val Lys Leu Phe Ser Asp Ile Glu Asn Ile Ser
    1235                1240                1245

Glu Glu Thr Ser Ala Glu Val His Pro Ile Ser Leu Ser Ser Ser
    1250                1255                1260

Lys Cys His Asp Ser Val Val Ser Met Phe Lys Ile Glu Asn His
    1265                1270                1275

Asn Asp Lys Thr Val Ser Glu Lys Asn Asn Lys Cys Gln Leu Ile
    1280                1285                1290

Leu Gln Asn Asn Ile Glu Met Thr Thr Gly Thr Phe Val Glu Glu
    1295                1300                1305

Ile Thr Glu Asn Tyr Lys Arg Asn Thr Glu Asn Glu Asp Asn Lys
    1310                1315                1320

Tyr Thr Ala Ala Ser Arg Asn Ser His Asn Leu Glu Phe Asp Gly
    1325                1330                1335

Ser Asp Ser Ser Lys Asn Asp Thr Val Cys Ile His Lys Asp Glu
```

```
            1340                1345                1350

Thr Asp Leu Leu Phe Thr Asp Gln His Asn Ile Cys Leu Lys Leu
    1355                1360                1365

Ser Gly Gln Phe Met Lys Glu Gly Asn Thr Gln Ile Lys Glu Asp
    1370                1375                1380

Leu Ser Asp Leu Thr Phe Leu Glu Val Ala Lys Ala Gln Glu Ala
    1385                1390                1395

Cys His Gly Asn Thr Ser Asn Lys Glu Gln Leu Thr Ala Thr Lys
    1400                1405                1410

Thr Glu Gln Asn Ile Lys Asp Phe Glu Thr Ser Asp Thr Phe Phe
    1415                1420                1425

Gln Thr Ala Ser Gly Lys Asn Ile Ser Val Ala Lys Glu Ser Phe
    1430                1435                1440

Asn Lys Ile Val Asn Phe Phe Asp Gln Lys Pro Glu Glu Leu His
    1445                1450                1455

Asn Phe Ser Leu Asn Ser Glu Leu His Ser Asp Ile Arg Lys Asn
    1460                1465                1470

Lys Met Asp Ile Leu Ser Tyr Glu Glu Thr Asp Ile Val Lys His
    1475                1480                1485

Lys Ile Leu Lys Glu Ser Val Pro Val Gly Thr Gly Asn Gln Leu
    1490                1495                1500

Val Thr Phe Gln Gly Gln Pro Glu Arg Asp Glu Lys Ile Lys Glu
    1505                1510                1515

Pro Thr Leu Leu Gly Phe His Thr Ala Ser Gly Lys Lys Val Lys
    1520                1525                1530

Ile Ala Lys Glu Ser Leu Asp Lys Val Lys Asn Leu Phe Asp Glu
    1535                1540                1545

Lys Glu Gln Gly Thr Ser Glu Ile Thr Ser Phe Ser His Gln Trp
    1550                1555                1560

Ala Lys Thr Leu Lys Tyr Arg Glu Ala Cys Lys Asp Leu Glu Leu
    1565                1570                1575

Ala Cys Glu Thr Ile Glu Ile Thr Ala Ala Pro Lys Cys Lys Glu
    1580                1585                1590

Met Gln Asn Ser Leu Asn Asn Asp Lys Asn Leu Val Ser Ile Glu
    1595                1600                1605

Thr Val Val Pro Pro Lys Leu Leu Ser Asp Asn Leu Cys Arg Gln
    1610                1615                1620

Thr Glu Asn Leu Lys Thr Ser Lys Ser Ile Phe Leu Lys Val Lys
    1625                1630                1635

Val His Glu Asn Val Glu Lys Glu Thr Ala Lys Ser Pro Ala Thr
    1640                1645                1650

Cys Tyr Thr Asn Gln Ser Pro Tyr Ser Val Ile Glu Asn Ser Ala
    1655                1660                1665

Leu Ala Phe Tyr Thr Ser Cys Ser Arg Lys Thr Ser Val Ser Gln
    1670                1675                1680

Thr Ser Leu Leu Glu Ala Lys Lys Trp Leu Arg Glu Gly Ile Phe
    1685                1690                1695

Asp Gly Gln Pro Glu Arg Ile Asn Thr Ala Asp Tyr Val Gly Asn
    1700                1705                1710

Tyr Leu Tyr Glu Asn Asn Ser Asn Ser Thr Ile Ala Glu Asn Asp
    1715                1720                1725

Lys Asn His Leu Ser Glu Lys Gln Asp Thr Tyr Leu Ser Asn Ser
    1730                1735                1740
```

```
Ser Met Ser Asn Ser Tyr Ser Tyr His Ser Asp Glu Val Tyr Asn
    1745            1750            1755

Asp Ser Gly Tyr Leu Ser Lys Asn Lys Leu Asp Ser Gly Ile Glu
    1760            1765            1770

Pro Val Leu Lys Asn Val Glu Asp Gln Lys Asn Thr Ser Phe Ser
    1775            1780            1785

Lys Val Ile Ser Asn Val Lys Asp Ala Asn Ala Tyr Pro Gln Thr
    1790            1795            1800

Val Asn Glu Asp Ile Cys Val Glu Leu Val Thr Ser Ser Ser
    1805            1810            1815

Pro Cys Lys Asn Lys Asn Ala Ala Ile Lys Leu Ser Ile Ser Asn
    1820            1825            1830

Ser Asn Asn Phe Glu Val Gly Pro Pro Ala Phe Arg Ile Ala Ser
    1835            1840            1845

Gly Lys Ile Val Cys Val Ser His Glu Thr Ile Lys Lys Val Lys
    1850            1855            1860

Asp Ile Phe Thr Asp Ser Phe Ser Lys Val Ile Lys Glu Asn Asn
    1865            1870            1875

Glu Asn Lys Ser Lys Ile Cys Gln Thr Lys Ile Met Ala Gly Cys
    1880            1885            1890

Tyr Glu Ala Leu Asp Asp Ser Glu Asp Ile Leu His Asn Ser Leu
    1895            1900            1905

Asp Asn Asp Glu Cys Ser Thr His Ser His Lys Val Phe Ala Asp
    1910            1915            1920

Ile Gln Ser Glu Glu Ile Leu Gln His Asn Gln Asn Met Ser Gly
    1925            1930            1935

Leu Glu Lys Val Ser Lys Ile Ser Pro Cys Asp Val Ser Leu Glu
    1940            1945            1950

Thr Ser Asp Ile Cys Lys Cys Ser Ile Gly Lys Leu His Lys Ser
    1955            1960            1965

Val Ser Ser Ala Asn Thr Cys Gly Ile Phe Ser Thr Ala Ser Gly
    1970            1975            1980

Lys Ser Val Gln Val Ser Asp Ala Ser Leu Gln Asn Ala Arg Gln
    1985            1990            1995

Val Phe Ser Glu Ile Glu Asp Ser Thr Lys Gln Val Phe Ser Lys
    2000            2005            2010

Val Leu Phe Lys Ser Asn Glu His Ser Asp Gln Leu Thr Arg Glu
    2015            2020            2025

Glu Asn Thr Ala Ile Arg Thr Pro Glu His Leu Ile Ser Gln Lys
    2030            2035            2040

Gly Phe Ser Tyr Asn Val Val Asn Ser Ser Ala Phe Ser Gly Phe
    2045            2050            2055

Ser Thr Ala Ser Gly Lys Gln Val Ser Ile Leu Glu Ser Ser Leu
    2060            2065            2070

His Lys Val Lys Gly Val Leu Glu Glu Phe Asp Leu Ile Arg Thr
    2075            2080            2085

Glu His Ser Leu His Tyr Ser Pro Thr Ser Arg Gln Asn Val Ser
    2090            2095            2100

Lys Ile Leu Pro Arg Val Asp Lys Arg Asn Pro Glu His Cys Val
    2105            2110            2115

Asn Ser Glu Met Glu Lys Thr Cys Ser Lys Glu Phe Lys Leu Ser
    2120            2125            2130
```

```
Asn Asn Leu Asn Val Glu Gly Gly Ser Ser Glu Asn Asn His Ser
    2135            2140                2145

Ile Lys Val Ser Pro Tyr Leu Ser Gln Phe Gln Gln Asp Lys Gln
    2150            2155                2160

Gln Leu Val Leu Gly Thr Lys Val Ser Leu Val Glu Asn Ile His
    2165            2170                2175

Val Leu Gly Lys Glu Gln Ala Ser Pro Lys Asn Val Lys Met Glu
    2180            2185                2190

Ile Gly Lys Thr Glu Thr Phe Ser Asp Val Pro Val Lys Thr Asn
    2195            2200                2205

Ile Glu Val Cys Ser Thr Tyr Ser Lys Asp Ser Glu Asn Tyr Phe
    2210            2215                2220

Glu Thr Glu Ala Val Glu Ile Ala Lys Ala Phe Met Glu Asp Asp
    2225            2230                2235

Glu Leu Thr Asp Ser Lys Leu Pro Ser His Ala Thr His Ser Leu
    2240            2245                2250

Phe Thr Cys Pro Glu Asn Glu Glu Met Val Leu Ser Asn Ser Arg
    2255            2260                2265

Ile Gly Lys Arg Arg Gly Glu Pro Leu Ile Leu Val Gly Glu Pro
    2270            2275                2280

Ser Ile Lys Arg Asn Leu Leu Asn Glu Phe Asp Arg Ile Ile Glu
    2285            2290                2295

Asn Gln Glu Lys Ser Leu Lys Ala Ser Lys Ser Thr Pro Asp Gly
    2300            2305                2310

Thr Ile Lys Asp Arg Arg Leu Phe Met His His Val Ser Leu Glu
    2315            2320                2325

Pro Ile Thr Cys Val Pro Phe Arg Thr Thr Lys Glu Arg Gln Glu
    2330            2335                2340

Ile Gln Asn Pro Asn Phe Thr Ala Pro Gly Gln Glu Phe Leu Ser
    2345            2350                2355

Lys Ser His Leu Tyr Glu His Leu Thr Leu Glu Lys Ser Ser Ser
    2360            2365                2370

Asn Leu Ala Val Ser Gly His Pro Phe Tyr Gln Val Ser Ala Thr
    2375            2380                2385

Arg Asn Glu Lys Met Arg His Leu Ile Thr Thr Gly Arg Pro Thr
    2390            2395                2400

Lys Val Phe Val Pro Pro Phe Lys Thr Lys Ser His Phe His Arg
    2405            2410                2415

Val Glu Gln Cys Val Arg Asn Ile Asn Leu Glu Glu Asn Arg Gln
    2420            2425                2430

Lys Gln Asn Ile Asp Gly His Gly Ser Asp Asp Ser Lys Asn Lys
    2435            2440                2445

Ile Asn Asp Asn Glu Ile His Gln Phe Asn Lys Asn Asn Ser Asn
    2450            2455                2460

Gln Ala Ala Ala Val Thr Phe Thr Lys Cys Glu Glu Glu Pro Leu
    2465            2470                2475

Asp Leu Ile Thr Ser Leu Gln Asn Ala Arg Asp Ile Gln Asp Met
    2480            2485                2490

Arg Ile Lys Lys Lys Gln Arg Gln Arg Val Phe Pro Gln Pro Gly
    2495            2500                2505

Ser Leu Tyr Leu Ala Lys Thr Ser Thr Leu Pro Arg Ile Ser Leu
    2510            2515                2520

Lys Ala Ala Val Gly Gly Gln Val Pro Ser Ala Cys Ser His Lys
```

```
                2525                2530                2535

Gln Leu Tyr Thr Tyr Gly Val Ser Lys His Cys Ile Lys Ile Asn
    2540                2545                2550

Ser Lys Asn Ala Glu Ser Phe Gln Phe His Thr Glu Asp Tyr Phe
    2555                2560                2565

Gly Lys Glu Ser Leu Trp Thr Gly Lys Gly Ile Gln Leu Ala Asp
    2570                2575                2580

Gly Gly Trp Leu Ile Pro Ser Asn Asp Gly Lys Ala Gly Lys Glu
    2585                2590                2595

Glu Phe Tyr Arg Ala Leu Cys Asp Thr Pro Gly Val Asp Pro Lys
    2600                2605                2610

Leu Ile Ser Arg Ile Trp Val Tyr Asn His Tyr Arg Trp Ile Ile
    2615                2620                2625

Trp Lys Leu Ala Ala Met Glu Cys Ala Phe Pro Lys Glu Phe Ala
    2630                2635                2640

Asn Arg Cys Leu Ser Pro Glu Arg Val Leu Leu Gln Leu Lys Tyr
    2645                2650                2655

Arg Tyr Asp Thr Glu Ile Asp Arg Ser Arg Arg Ser Ala Ile Lys
    2660                2665                2670

Lys Ile Met Glu Arg Asp Asp Thr Ala Ala Lys Thr Leu Val Leu
    2675                2680                2685

Cys Val Ser Asp Ile Ile Ser Leu Ser Ala Asn Ile Ser Glu Thr
    2690                2695                2700

Ser Ser Asn Lys Thr Ser Ser Ala Asp Thr Gln Lys Val Ala Ile
    2705                2710                2715

Ile Glu Leu Thr Asp Gly Trp Tyr Ala Val Lys Ala Gln Leu Asp
    2720                2725                2730

Pro Pro Leu Leu Ala Val Leu Lys Asn Gly Arg Leu Thr Val Gly
    2735                2740                2745

Gln Lys Ile Ile Leu His Gly Ala Glu Leu Val Gly Ser Pro Asp
    2750                2755                2760

Ala Cys Thr Pro Leu Glu Ala Pro Glu Ser Leu Met Leu Lys Ile
    2765                2770                2775

Ser Ala Asn Ser Thr Arg Pro Ala Arg Trp Tyr Thr Lys Leu Gly
    2780                2785                2790

Phe Phe Pro Asp Pro Arg Pro Phe Pro Leu Pro Leu Ser Ser Leu
    2795                2800                2805

Phe Ser Asp Gly Gly Asn Val Gly Cys Val Asp Val Ile Ile Gln
    2810                2815                2820

Arg Ala Tyr Pro Ile Gln Trp Met Glu Lys Thr Ser Ser Gly Leu
    2825                2830                2835

Tyr Ile Phe Arg Asn Glu Arg Glu Glu Glu Lys Glu Ala Ala Lys
    2840                2845                2850

Tyr Val Glu Ala Gln Gln Lys Arg Leu Glu Ala Leu Phe Thr Lys
    2855                2860                2865

Ile Gln Glu Glu Phe Glu Glu His Glu Glu Asn Thr Thr Lys Pro
    2870                2875                2880

Tyr Leu Pro Ser Arg Ala Leu Thr Arg Gln Gln Val Arg Ala Leu
    2885                2890                2895

Gln Asp Gly Ala Glu Leu Tyr Glu Ala Val Lys Asn Ala Ala Asp
    2900                2905                2910

Pro Ala Tyr Leu Glu Gly Tyr Phe Ser Glu Glu Gln Leu Arg Ala
    2915                2920                2925
```

```
Leu Asn Asn His Arg Gln Met Leu Asn Asp Lys Lys Gln Ala Gln
    2930            2935                2940

Ile Gln Leu Glu Ile Arg Lys Ala Met Glu Ser Ala Glu Gln Lys
    2945            2950                2955

Glu Gln Gly Leu Ser Arg Asp Val Thr Thr Val Trp Lys Leu Arg
    2960            2965                2970

Ile Val Ser Tyr Ser Lys Lys Glu Lys Asp Ser Val Ile Leu Ser
    2975            2980                2985

Ile Trp Arg Pro Ser Ser Asp Leu Tyr Ser Leu Leu Thr Glu Gly
    2990            2995                3000

Lys Arg Tyr Arg Ile Tyr His Leu Ala Thr Ser Lys Ser Lys Ser
    3005            3010                3015

Lys Ser Glu Arg Ala Asn Ile Gln Leu Ala Ala Thr Lys Lys Thr
    3020            3025                3030

Gln Tyr Gln Gln Leu Pro Val Ser Asp Glu Ile Leu Phe Gln Ile
    3035            3040                3045

Tyr Gln Pro Arg Glu Pro Leu His Phe Ser Lys Phe Leu Asp Pro
    3050            3055                3060

Asp Phe Gln Pro Ser Cys Ser Glu Val Asp Leu Ile Gly Phe Val
    3065            3070                3075

Val Ser Val Val Lys Lys Thr Gly Leu Ala Pro Phe Val Tyr Leu
    3080            3085                3090

Ser Asp Glu Cys Tyr Asn Leu Leu Ala Ile Lys Phe Trp Ile Asp
    3095            3100                3105

Leu Asn Glu Asp Ile Ile Lys Pro His Met Leu Ile Ala Ala Ser
    3110            3115                3120

Asn Leu Gln Trp Arg Pro Glu Ser Lys Ser Gly Leu Leu Thr Leu
    3125            3130                3135

Phe Ala Gly Asp Phe Ser Val Phe Ser Ala Ser Pro Lys Glu Gly
    3140            3145                3150

His Phe Gln Glu Thr Phe Asn Lys Met Lys Asn Thr Val Glu Asn
    3155            3160                3165

Ile Asp Ile Leu Cys Asn Glu Ala Glu Asn Lys Leu Met His Ile
    3170            3175                3180

Leu His Ala Asn Asp Pro Lys Trp Ser Thr Pro Thr Lys Asp Cys
    3185            3190                3195

Thr Ser Gly Pro Tyr Thr Ala Gln Ile Ile Pro Gly Thr Gly Asn
    3200            3205                3210

Lys Leu Leu Met Ser Ser Pro Asn Cys Glu Ile Tyr Tyr Gln Ser
    3215            3220                3225

Pro Leu Ser Leu Cys Met Ala Lys Arg Lys Ser Val Ser Thr Pro
    3230            3235                3240

Val Ser Ala Gln Met Thr Ser Lys Ser Cys Lys Gly Glu Lys Glu
    3245            3250                3255

Ile Asp Asp Gln Lys Asn Cys Lys Lys Arg Arg Ala Leu Asp Phe
    3260            3265                3270

Leu Ser Arg Leu Pro Leu Pro Pro Pro Val Ser Pro Ile Cys Thr
    3275            3280                3285

Phe Val Ser Pro Ala Ala Gln Lys Ala Phe Gln Pro Pro Arg Ser
    3290            3295                3300

Cys Gly Thr Lys Tyr Glu Thr Pro Ile Lys Lys Lys Glu Leu Asn
    3305            3310                3315
```

Ser Pro Gln Met Thr Pro Phe Lys Lys Phe Asn Glu Ile Ser Leu
3320                3325                3330

Leu Glu Ser Asn Ser Ile Ala Asp Glu Glu Leu Ala Leu Ile Asn
    3335                3340                3345

Thr Gln Ala Leu Leu Ser Gly Ser Thr Gly Glu Lys Gln Phe Ile
3350                3355                3360

Ser Val Ser Glu Ser Thr Arg Thr Ala Pro Thr Ser Ser Glu Asp
3365                3370                3375

Tyr Leu Arg Leu Lys Arg Arg Cys Thr Thr Ser Leu Ile Lys Glu
3380                3385                3390

Gln Glu Ser Ser Gln Ala Ser Thr Glu Glu Cys Glu Lys Asn Lys
3395                3400                3405

Gln Asp Thr Ile Thr Thr Lys Lys Tyr Ile
3410                3415

<210> SEQ ID NO 9
<211> LENGTH: 624
<212> TYPE: PRT
<213> ORGANISM: Homo sapiens

<400> SEQUENCE: 9

Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
                20                  25                  30

Tyr Ala Ser Thr Glu Cys Lys Ala Glu Val Thr Pro Ser Gln His Gly
            35                  40                  45

Asn Arg Thr Phe Ser Tyr Thr Leu Glu Asp His Thr Lys Gln Ala Phe
    50                  55                  60

Gly Ile Met Asn Glu Leu Arg Leu Ser Gln Gln Leu Cys Asp Val Thr
65                  70                  75                  80

Leu Gln Val Lys Tyr Gln Asp Ala Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Val Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
                245                 250                 255

Cys Glu Gln Arg Arg Phe Tyr Val Gln Ala Leu Leu Arg Ala Val Arg
            260                 265                 270

Cys His Ser Leu Thr Pro Asn Phe Leu Gln Met Gln Leu Gln Lys Cys
        275                 280                 285

Glu Ile Leu Gln Ser Asp Ser Arg Cys Lys Asp Tyr Leu Val Lys Ile
        290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asp Gly Thr Trp
                340                 345                 350

Leu Arg Leu Ala Asp Leu Gln Val Pro Arg Ser Gly Leu Ala Gly Cys
                355                 360                 365

Val Val Gly Gly Leu Leu Tyr Ala Val Gly Gly Arg Asn Asn Ser Pro
        370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
                405                 410                 415

Gly Val Gly Val Ile Asp Gly His Ile Tyr Ala Val Gly Gly Ser His
                420                 425                 430

Gly Cys Ile His His Asn Ser Val Glu Arg Tyr Glu Pro Glu Arg Asp
                435                 440                 445

Glu Trp His Leu Val Ala Pro Met Leu Thr Arg Arg Ile Gly Val Gly
                450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Ala Met Asn Thr Ile Arg Ser Gly Ala Gly Val
                500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
        530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
                565                 570                 575

Phe Leu Asp Ser Val Glu Cys Tyr Asp Pro Asp Thr Asp Thr Trp Ser
                580                 585                 590

Glu Val Thr Arg Met Thr Ser Gly Arg Ser Gly Val Gly Val Ala Val
                595                 600                 605

Thr Met Glu Pro Cys Arg Lys Gln Ile Asp Gln Gln Asn Cys Thr Cys
610                 615                 620

<210> SEQ ID NO 10
<211> LENGTH: 1977
<212> TYPE: PRT
<213> ORGANISM: Homo sapiens

<400> SEQUENCE: 10

Met Pro Gly Glu Gln Met Asp Pro Thr Gly Ser Gln Leu Asp Ser Asp
1                   5                   10                  15

Phe Ser Gln Gln Asp Thr Pro Cys Leu Ile Ile Glu Asp Ser Gln Pro

```
                20                  25                  30
Glu Ser Gln Val Leu Glu Asp Asp Ser Gly Ser His Phe Ser Met Leu
            35                  40                  45
Ser Arg His Leu Pro Asn Leu Gln Thr His Lys Glu Asn Pro Val Leu
        50                  55                  60
Asp Val Val Ser Asn Pro Glu Gln Thr Ala Gly Glu Arg Gly Asp
65                  70                  75                  80
Gly Asn Ser Gly Phe Asn Glu His Leu Lys Glu Asn Lys Val Ala Asp
                85                  90                  95
Pro Val Asp Ser Ser Asn Leu Asp Thr Cys Gly Ser Ile Ser Gln Val
            100                 105                 110
Ile Glu Gln Leu Pro Gln Pro Asn Arg Thr Ser Ser Val Leu Gly Met
        115                 120                 125
Ser Val Glu Ser Ala Pro Ala Val Glu Glu Lys Gly Glu Glu Leu
        130                 135                 140
Glu Gln Lys Glu Lys Glu Lys Glu Glu Asp Thr Ser Gly Asn Thr Thr
145                 150                 155                 160
His Ser Leu Gly Ala Glu Asp Thr Ala Ser Ser Gln Leu Gly Phe Gly
            165                 170                 175
Val Leu Glu Leu Ser Gln Ser Gln Asp Val Glu Asn Thr Val Pro
        180                 185                 190
Tyr Glu Val Asp Lys Glu Gln Leu Gln Ser Val Thr Thr Asn Ser Gly
            195                 200                 205
Tyr Thr Arg Leu Ser Asp Val Asp Ala Asn Thr Ala Ile Lys His Glu
        210                 215                 220
Glu Gln Ser Asn Glu Asp Ile Pro Ile Ala Glu Gln Ser Ser Lys Asp
225                 230                 235                 240
Ile Pro Val Thr Ala Gln Pro Ser Lys Asp Val His Val Val Lys Glu
            245                 250                 255
Gln Asn Pro Pro Pro Ala Arg Ser Glu Asp Met Pro Phe Ser Pro Lys
            260                 265                 270
Ala Ser Val Ala Ala Met Glu Ala Lys Glu Gln Leu Ser Ala Gln Glu
            275                 280                 285
Leu Met Glu Ser Gly Leu Gln Ile Gln Lys Ser Pro Glu Pro Glu Val
        290                 295                 300
Leu Ser Thr Gln Glu Asp Leu Phe Asp Gln Ser Asn Lys Thr Val Ser
305                 310                 315                 320
Ser Asp Gly Cys Ser Thr Pro Ser Arg Glu Glu Gly Gly Cys Ser Leu
            325                 330                 335
Ala Ser Thr Pro Ala Thr Thr Leu His Leu Leu Gln Leu Ser Gly Gln
            340                 345                 350
Arg Ser Leu Val Gln Asp Ser Leu Ser Thr Asn Ser Ser Asp Leu Val
        355                 360                 365
Ala Pro Ser Pro Asp Ala Phe Arg Ser Thr Pro Phe Ile Val Pro Ser
        370                 375                 380
Ser Pro Thr Glu Gln Glu Gly Arg Gln Asp Lys Pro Met Asp Thr Ser
385                 390                 395                 400
Val Leu Ser Glu Glu Gly Gly Glu Pro Phe Lys Lys Leu Gln Ser
            405                 410                 415
Gly Glu Pro Val Glu Leu Glu Asn Pro Pro Leu Leu Pro Glu Ser Thr
            420                 425                 430
Val Ser Pro Gln Ala Ser Thr Pro Ile Ser Gln Ser Thr Pro Val Phe
            435                 440                 445
```

```
Pro Pro Gly Ser Leu Pro Ile Pro Ser Gln Pro Gln Phe Ser His Asp
    450                 455                 460
Ile Phe Ile Pro Ser Pro Ser Leu Glu Glu Gln Ser Asn Asp Gly Lys
465                 470                 475                 480
Lys Asp Gly Asp Met His Ser Ser Leu Thr Val Glu Cys Ser Lys
                    485                 490                 495
Thr Ser Glu Ile Glu Pro Lys Asn Ser Pro Glu Asp Leu Gly Leu Ser
                500                 505                 510
Leu Thr Gly Asp Ser Cys Lys Leu Met Leu Ser Thr Ser Glu Tyr Ser
            515                 520                 525
Gln Ser Pro Lys Met Glu Ser Leu Ser Ser His Arg Ile Asp Glu Asp
    530                 535                 540
Gly Glu Asn Thr Gln Ile Glu Asp Thr Glu Pro Met Ser Pro Val Leu
545                 550                 555                 560
Asn Ser Lys Phe Val Pro Ala Glu Asn Asp Ser Ile Leu Met Asn Pro
                565                 570                 575
Ala Gln Asp Gly Glu Val Gln Leu Ser Gln Asn Asp Asp Lys Thr Lys
                580                 585                 590
Gly Asp Asp Thr Asp Thr Arg Asp Asp Ile Ser Ile Leu Ala Thr Gly
            595                 600                 605
Cys Lys Gly Arg Glu Glu Thr Val Ala Glu Asp Val Cys Ile Asp Leu
    610                 615                 620
Thr Cys Asp Ser Gly Ser Gln Ala Val Pro Ser Pro Ala Thr Arg Ser
625                 630                 635                 640
Glu Ala Leu Ser Ser Val Leu Asp Gln Glu Glu Ala Met Glu Ile Lys
                645                 650                 655
Glu His His Pro Glu Glu Gly Ser Ser Gly Ser Glu Val Glu Glu Ile
                660                 665                 670
Pro Glu Thr Pro Cys Glu Ser Gln Gly Glu Glu Leu Lys Glu Glu Asn
            675                 680                 685
Met Glu Ser Val Pro Leu His Leu Ser Leu Thr Glu Thr Gln Ser Gln
690                 695                 700
Gly Leu Cys Leu Gln Lys Glu Met Pro Lys Lys Glu Cys Ser Glu Ala
705                 710                 715                 720
Met Glu Val Glu Thr Ser Val Ile Ser Ile Asp Ser Pro Gln Lys Leu
                725                 730                 735
Ala Ile Leu Asp Gln Glu Leu Glu His Lys Glu Gln Glu Ala Trp Glu
                740                 745                 750
Glu Ala Thr Ser Glu Asp Ser Val Val Ile Val Asp Val Lys Glu
            755                 760                 765
Pro Ser Pro Arg Val Asp Val Ser Cys Glu Pro Leu Glu Gly Val Glu
    770                 775                 780
Lys Cys Ser Asp Ser Gln Ser Trp Glu Asp Ile Ala Pro Glu Ile Glu
785                 790                 795                 800
Pro Cys Ala Glu Asn Arg Leu Asp Thr Lys Glu Lys Ser Val Glu
                805                 810                 815
Tyr Glu Gly Asp Leu Lys Ser Gly Thr Ala Glu Thr Glu Pro Val Glu
                820                 825                 830
Gln Asp Ser Ser Gln Pro Ser Leu Pro Leu Val Arg Ala Asp Asp Pro
            835                 840                 845
Leu Arg Leu Asp Gln Glu Leu Gln Gln Pro Gln Thr Gln Glu Lys Thr
    850                 855                 860
```

```
Ser Asn Ser Leu Thr Glu Asp Ser Lys Met Ala Asn Ala Lys Gln Leu
865                 870                 875                 880

Ser Ser Asp Ala Glu Ala Gln Lys Leu Gly Lys Pro Ser Ala His Ala
            885                 890                 895

Ser Gln Ser Phe Cys Glu Ser Ser Ser Glu Thr Pro Phe His Phe Thr
        900                 905                 910

Leu Pro Lys Glu Gly Asp Ile Ile Pro Pro Leu Thr Gly Ala Thr Pro
    915                 920                 925

Pro Leu Ile Gly His Leu Lys Leu Glu Pro Lys Arg His Ser Thr Pro
    930                 935                 940

Ile Gly Ile Ser Asn Tyr Pro Glu Ser Thr Ile Ala Thr Ser Asp Val
945                 950                 955                 960

Met Ser Glu Ser Met Val Glu Thr His Asp Pro Ile Leu Gly Ser Gly
            965                 970                 975

Lys Gly Asp Ser Gly Ala Ala Pro Asp Val Asp Asp Lys Leu Cys Leu
            980                 985                 990

Arg Met Lys Leu Val Ser Pro Glu Thr Glu Ala Ser Glu Glu Ser Leu
        995                 1000                1005

Gln Phe Asn Leu Glu Lys Pro Ala Thr Gly Glu Arg Lys Asn Gly
    1010                1015                1020

Ser Thr Ala Val Ala Glu Ser Val Ala Ser Pro Gln Lys Thr Met
    1025                1030                1035

Ser Val Leu Ser Cys Ile Cys Glu Ala Arg Gln Glu Asn Glu Ala
    1040                1045                1050

Arg Ser Glu Asp Pro Pro Thr Thr Pro Ile Arg Gly Asn Leu Leu
    1055                1060                1065

His Phe Pro Ser Ser Gln Gly Glu Glu Lys Glu Lys Leu Glu
    1070                1075                1080

Gly Asp His Thr Ile Arg Gln Ser Gln Pro Met Lys Pro Ile
    1085                1090                1095

Ser Pro Val Lys Asp Pro Val Ser Pro Ala Ser Gln Lys Met Val
    1100                1105                1110

Ile Gln Gly Pro Ser Ser Pro Gln Gly Glu Ala Met Val Thr Asp
    1115                1120                1125

Val Leu Glu Asp Gln Lys Glu Gly Arg Ser Thr Asn Lys Glu Asn
    1130                1135                1140

Pro Ser Lys Ala Leu Ile Glu Arg Pro Ser Gln Asn Asn Ile Gly
    1145                1150                1155

Ile Gln Thr Met Glu Cys Ser Leu Arg Val Pro Glu Thr Val Ser
    1160                1165                1170

Ala Ala Thr Gln Thr Ile Lys Asn Val Cys Glu Gln Gly Thr Ser
    1175                1180                1185

Thr Val Asp Gln Asn Phe Gly Lys Gln Asp Ala Thr Val Gln Thr
    1190                1195                1200

Glu Arg Gly Ser Gly Glu Lys Pro Val Ser Ala Pro Gly Asp Asp
    1205                1210                1215

Thr Glu Ser Leu His Ser Gln Gly Glu Glu Phe Asp Met Pro
    1220                1225                1230

Gln Pro Pro His Gly His Val Leu His Arg His Met Arg Thr Ile
    1235                1240                1245

Arg Glu Val Arg Thr Leu Val Thr Arg Val Ile Thr Asp Val Tyr
    1250                1255                1260

Tyr Val Asp Gly Thr Glu Val Glu Arg Lys Val Thr Glu Glu Thr
```

```
            1265                1270                1275

Glu Glu Pro Ile Val Glu Cys Gln Glu Cys Thr Glu Val Ser
        1280                1285                1290

Pro Ser Gln Thr Gly Gly Ser Ser Gly Asp Leu Gly Asp Ile Ser
    1295                1300                1305

Ser Phe Ser Ser Lys Ala Ser Ser Leu His Arg Thr Ser Ser Gly
    1310                1315                1320

Thr Ser Leu Ser Ala Met His Ser Ser Gly Ser Ser Gly Lys Gly
    1325                1330                1335

Ala Gly Pro Leu Arg Gly Lys Thr Ser Gly Thr Glu Pro Ala Asp
    1340                1345                1350

Phe Ala Leu Pro Ser Ser Arg Gly Gly Pro Gly Lys Leu Ser Pro
    1355                1360                1365

Arg Lys Gly Val Ser Gln Thr Gly Thr Pro Val Cys Glu Glu Asp
    1370                1375                1380

Gly Asp Ala Gly Leu Gly Ile Arg Gln Gly Gly Lys Ala Pro Val
    1385                1390                1395

Thr Pro Arg Gly Arg Gly Arg Gly Arg Gly Arg Pro Pro Ser Arg Thr
    1400                1405                1410

Thr Gly Thr Arg Glu Thr Ala Val Pro Gly Pro Leu Gly Ile Glu
    1415                1420                1425

Asp Ile Ser Pro Asn Leu Ser Pro Asp Asp Lys Ser Phe Ser Arg
    1430                1435                1440

Val Val Pro Arg Val Pro Asp Ser Thr Arg Arg Thr Asp Val Gly
    1445                1450                1455

Ala Gly Ala Leu Arg Arg Ser Asp Ser Pro Glu Ile Pro Phe Gln
    1460                1465                1470

Ala Ala Ala Gly Pro Ser Asp Gly Leu Asp Ala Ser Ser Pro Gly
    1475                1480                1485

Asn Ser Phe Val Gly Leu Arg Val Val Ala Lys Trp Ser Ser Asn
    1490                1495                1500

Gly Tyr Phe Tyr Ser Gly Lys Ile Thr Arg Asp Val Gly Ala Gly
    1505                1510                1515

Lys Tyr Lys Leu Leu Phe Asp Asp Gly Tyr Glu Cys Asp Val Leu
    1520                1525                1530

Gly Lys Asp Ile Leu Leu Cys Asp Pro Ile Pro Leu Asp Thr Glu
    1535                1540                1545

Val Thr Ala Leu Ser Glu Asp Glu Tyr Phe Ser Ala Gly Val Val
    1550                1555                1560

Lys Gly His Arg Lys Glu Ser Gly Glu Leu Tyr Tyr Ser Ile Glu
    1565                1570                1575

Lys Glu Gly Gln Arg Lys Trp Tyr Lys Arg Met Ala Val Ile Leu
    1580                1585                1590

Ser Leu Glu Gln Gly Asn Arg Leu Arg Glu Gln Tyr Gly Leu Gly
    1595                1600                1605

Pro Tyr Glu Ala Val Thr Pro Leu Thr Lys Ala Ala Asp Ile Ser
    1610                1615                1620

Leu Asp Asn Leu Val Glu Gly Lys Arg Lys Arg Arg Ser Asn Val
    1625                1630                1635

Ser Ser Pro Ala Thr Pro Thr Ala Ser Ser Ser Ser Thr Thr
    1640                1645                1650

Pro Thr Arg Lys Ile Thr Glu Ser Pro Arg Ala Ser Met Gly Val
    1655                1660                1665
```

```
Leu Ser Gly Lys Arg Lys Leu Ile Thr Ser Glu Glu Glu Arg Ser
    1670            1675                1680

Pro Ala Lys Arg Gly Arg Lys Ser Ala Thr Val Lys Pro Gly Ala
    1685            1690                1695

Val Gly Ala Gly Glu Phe Val Ser Pro Cys Glu Ser Gly Asp Asn
    1700            1705                1710

Thr Gly Glu Pro Ser Ala Leu Glu Glu Gln Arg Gly Pro Leu Pro
    1715            1720                1725

Leu Asn Lys Thr Leu Phe Leu Gly Tyr Ala Phe Leu Leu Thr Met
    1730            1735                1740

Ala Thr Thr Ser Asp Lys Leu Ala Ser Arg Ser Lys Leu Pro Asp
    1745            1750                1755

Gly Pro Thr Gly Ser Ser Glu Glu Glu Glu Phe Leu Glu Ile
    1760            1765                1770

Pro Pro Phe Asn Lys Gln Tyr Thr Glu Ser Gln Leu Arg Ala Gly
    1775            1780                1785

Ala Gly Tyr Ile Leu Glu Asp Phe Asn Glu Ala Gln Cys Asn Thr
    1790            1795                1800

Ala Tyr Gln Cys Leu Leu Ile Ala Asp Gln His Cys Arg Thr Arg
    1805            1810                1815

Lys Tyr Phe Leu Cys Leu Ala Ser Gly Ile Pro Cys Val Ser His
    1820            1825                1830

Val Trp Val His Asp Ser Cys His Ala Asn Gln Leu Gln Asn Tyr
    1835            1840                1845

Arg Asn Tyr Leu Leu Pro Ala Gly Tyr Ser Leu Glu Glu Gln Arg
    1850            1855                1860

Ile Leu Asp Trp Gln Pro Arg Glu Asn Pro Phe Gln Asn Leu Lys
    1865            1870                1875

Val Leu Leu Val Ser Asp Gln Gln Asn Phe Leu Glu Leu Trp
    1880            1885                1890

Ser Glu Ile Leu Met Thr Gly Gly Ala Ala Ser Val Lys Gln His
    1895            1900                1905

His Ser Ser Ala His Asn Lys Asp Ile Ala Leu Gly Val Phe Asp
    1910            1915                1920

Val Val Val Thr Asp Pro Ser Cys Pro Ala Ser Val Leu Lys Cys
    1925            1930                1935

Ala Glu Ala Leu Gln Leu Pro Val Val Ser Gln Glu Trp Val Ile
    1940            1945                1950

Gln Cys Leu Ile Val Gly Glu Arg Ile Gly Phe Lys Gln His Pro
    1955            1960                1965

Lys Tyr Lys His Asp Tyr Val Ser His
    1970            1975

<210> SEQ ID NO 11
<211> LENGTH: 1975
<212> TYPE: PRT
<213> ORGANISM: Homo sapiens

<400> SEQUENCE: 11

Met Pro Gly Glu Gln Met Asp Pro Thr Gly Ser Gln Leu Asp Ser Asp
1               5                   10                  15

Phe Ser Gln Gln Asp Thr Pro Cys Leu Ile Ile Glu Asp Ser Gln Pro
                20                  25                  30

Glu Ser Gln Val Leu Glu Asp Asp Ser Gly Ser His Phe Ser Met Leu
```

```
            35                  40                  45
Ser Arg His Leu Pro Asn Leu Gln Thr His Lys Glu Asn Pro Val Leu
 50                  55                  60

Asp Val Val Ser Asn Pro Glu Gln Thr Ala Gly Glu Arg Gly Asp
 65                  70                  75                  80

Gly Asn Ser Gly Phe Asn Glu His Leu Lys Glu Asn Lys Val Ala Asp
                 85                  90                  95

Pro Val Asp Ser Ser Asn Leu Asp Thr Cys Gly Ser Ile Ser Gln Val
                100                 105                 110

Ile Glu Gln Leu Pro Gln Pro Asn Arg Thr Ser Ser Val Leu Gly Met
                115                 120                 125

Ser Val Glu Ser Ala Pro Ala Val Glu Glu Lys Gly Glu Glu Leu
130                 135                 140

Glu Gln Lys Glu Lys Glu Lys Glu Glu Asp Thr Ser Gly Asn Thr Thr
145                 150                 155                 160

His Ser Leu Gly Ala Glu Asp Thr Ala Ser Ser Gln Leu Gly Phe Gly
                165                 170                 175

Val Leu Glu Leu Ser Gln Ser Gln Asp Val Glu Glu Asn Thr Val Pro
                180                 185                 190

Tyr Glu Val Asp Lys Glu Gln Leu Gln Ser Val Thr Thr Asn Ser Gly
                195                 200                 205

Tyr Thr Arg Leu Ser Asp Val Asp Ala Asn Thr Ala Ile Lys His Glu
                210                 215                 220

Glu Gln Ser Asn Glu Asp Ile Pro Ile Ala Glu Gln Ser Ser Lys Asp
225                 230                 235                 240

Ile Pro Val Thr Ala Gln Pro Ser Lys Asp Val His Val Val Lys Glu
                245                 250                 255

Gln Asn Pro Pro Pro Ala Arg Ser Glu Asp Met Pro Phe Ser Pro Lys
                260                 265                 270

Ala Ser Val Ala Ala Met Glu Ala Lys Glu Gln Leu Ser Ala Gln Glu
                275                 280                 285

Leu Met Glu Ser Gly Leu Gln Ile Gln Lys Ser Pro Glu Pro Glu Val
                290                 295                 300

Leu Ser Thr Gln Glu Asp Leu Phe Asp Gln Ser Asn Lys Thr Val Ser
305                 310                 315                 320

Ser Asp Gly Cys Ser Thr Pro Ser Arg Glu Glu Gly Gly Cys Ser Leu
                325                 330                 335

Ala Ser Thr Pro Ala Thr Thr Leu His Leu Leu Gln Leu Ser Gly Gln
                340                 345                 350

Arg Ser Leu Val Gln Asp Ser Leu Ser Thr Asn Ser Ser Asp Leu Val
                355                 360                 365

Ala Pro Ser Pro Asp Ala Phe Arg Ser Thr Pro Phe Ile Val Pro Ser
                370                 375                 380

Ser Pro Thr Glu Gln Glu Gly Arg Gln Asp Lys Pro Met Asp Thr Ser
385                 390                 395                 400

Val Leu Ser Glu Glu Gly Gly Glu Pro Phe Gln Lys Lys Leu Gln Ser
                405                 410                 415

Gly Glu Pro Val Glu Leu Glu Asn Pro Pro Leu Leu Pro Glu Ser Thr
                420                 425                 430

Val Ser Pro Gln Ala Ser Thr Pro Ile Ser Gln Ser Thr Pro Val Phe
                435                 440                 445

Pro Pro Gly Ser Leu Pro Ile Pro Ser Gln Pro Gln Phe Ser His Asp
                450                 455                 460
```

-continued

```
Ile Phe Ile Pro Ser Pro Ser Leu Glu Glu Gln Ser Asn Asp Gly Lys
465                 470                 475                 480

Lys Asp Gly Asp Met His Ser Ser Leu Thr Val Glu Cys Ser Lys
                485                 490                 495

Thr Ser Glu Ile Glu Pro Lys Asn Ser Pro Glu Asp Leu Gly Leu Ser
            500                 505                 510

Leu Thr Gly Asp Ser Cys Lys Leu Met Leu Ser Thr Ser Glu Tyr Ser
                515                 520                 525

Gln Ser Pro Lys Met Glu Ser Leu Ser Ser His Arg Ile Asp Glu Asp
            530                 535                 540

Gly Glu Asn Thr Gln Ile Glu Asp Thr Glu Pro Met Ser Pro Val Leu
545                 550                 555                 560

Asn Ser Lys Phe Val Pro Ala Glu Asn Asp Ser Ile Leu Met Asn Pro
                565                 570                 575

Ala Gln Asp Gly Glu Val Gln Leu Ser Gln Asn Asp Asp Lys Thr Lys
                580                 585                 590

Gly Asp Asp Thr Asp Thr Arg Asp Asp Ile Ser Ile Leu Ala Thr Gly
                595                 600                 605

Cys Lys Gly Arg Glu Glu Thr Val Ala Glu Asp Val Cys Ile Asp Leu
610                 615                 620

Thr Cys Asp Ser Gly Ser Gln Ala Val Pro Ser Pro Ala Thr Arg Ser
625                 630                 635                 640

Glu Ala Leu Ser Ser Val Leu Asp Gln Glu Glu Ala Met Glu Ile Lys
                645                 650                 655

Glu His His Pro Glu Glu Gly Ser Gly Ser Glu Val Glu Glu Ile
                660                 665                 670

Pro Glu Thr Pro Cys Glu Ser Gln Gly Glu Glu Leu Lys Glu Glu Asn
                675                 680                 685

Met Glu Ser Val Pro Leu His Leu Ser Leu Thr Glu Thr Gln Ser Gln
                690                 695                 700

Gly Leu Cys Leu Gln Lys Glu Met Pro Lys Lys Glu Cys Ser Glu Ala
705                 710                 715                 720

Met Glu Val Glu Thr Ser Val Ile Ser Ile Asp Ser Pro Gln Lys Leu
                725                 730                 735

Ala Ile Leu Asp Gln Glu Leu Glu His Lys Glu Gln Glu Ala Trp Glu
                740                 745                 750

Glu Ala Thr Ser Glu Asp Ser Ser Val Val Ile Val Asp Val Lys Glu
                755                 760                 765

Pro Ser Pro Arg Val Asp Val Ser Cys Glu Pro Leu Glu Gly Val Glu
                770                 775                 780

Lys Cys Ser Asp Ser Gln Ser Trp Glu Asp Ile Ala Pro Glu Ile Glu
785                 790                 795                 800

Pro Cys Ala Glu Asn Arg Leu Asp Thr Lys Glu Glu Lys Ser Val Glu
                805                 810                 815

Tyr Glu Gly Asp Leu Lys Ser Gly Thr Ala Glu Thr Glu Pro Val Glu
                820                 825                 830

Gln Asp Ser Ser Gln Pro Ser Leu Pro Leu Val Arg Ala Asp Asp Pro
                835                 840                 845

Leu Arg Leu Asp Gln Glu Leu Gln Gln Pro Gln Thr Gln Glu Lys Thr
                850                 855                 860

Ser Asn Ser Leu Thr Glu Asp Ser Lys Met Ala Asn Ala Lys Gln Leu
865                 870                 875                 880
```

```
Ser Ser Asp Ala Glu Ala Gln Lys Leu Gly Lys Pro Ser Ala His Ala
            885                 890                 895

Ser Gln Ser Phe Cys Glu Ser Ser Glu Thr Pro Phe His Phe Thr
        900                 905                 910

Leu Pro Lys Glu Gly Asp Ile Ile Pro Pro Leu Thr Gly Ala Thr Pro
            915                 920                 925

Pro Leu Ile Gly His Leu Lys Leu Glu Pro Lys Arg His Ser Thr Pro
        930                 935                 940

Ile Gly Ile Ser Asn Tyr Pro Glu Ser Thr Ile Ala Thr Ser Asp Val
945                 950                 955                 960

Met Ser Glu Ser Met Val Glu Thr His Asp Pro Ile Leu Gly Ser Gly
            965                 970                 975

Lys Gly Asp Ser Gly Ala Ala Pro Asp Val Asp Asp Lys Leu Cys Leu
        980                 985                 990

Arg Met Lys Leu Val Ser Pro Glu Thr Glu Ala Ser Glu Glu Ser Leu
        995                 1000                1005

Gln Phe Asn Leu Glu Lys Pro Ala Thr Gly Glu Arg Lys Asn Gly
    1010                1015                1020

Ser Thr Ala Val Ala Glu Ser Val Ala Ser Pro Gln Lys Thr Met
    1025                1030                1035

Ser Val Leu Ser Cys Ile Cys Glu Ala Arg Gln Glu Asn Glu Ala
    1040                1045                1050

Arg Ser Glu Asp Pro Pro Thr Thr Pro Ile Arg Gly Asn Leu Leu
    1055                1060                1065

His Phe Pro Ser Ser Gln Gly Glu Glu Lys Glu Lys Leu Glu
    1070                1075                1080

Gly Asp His Thr Ile Arg Gln Ser Gln Gln Pro Met Lys Pro Ile
    1085                1090                1095

Ser Pro Val Lys Asp Pro Val Ser Pro Ala Ser Gln Lys Met Val
    1100                1105                1110

Ile Gln Gly Pro Ser Ser Pro Gln Gly Glu Ala Met Val Thr Asp
    1115                1120                1125

Val Leu Glu Asp Gln Lys Glu Gly Arg Ser Thr Asn Lys Glu Asn
    1130                1135                1140

Pro Ser Lys Ala Leu Ile Glu Arg Pro Ser Gln Asn Asn Ile Gly
    1145                1150                1155

Ile Gln Thr Met Glu Cys Ser Leu Arg Val Pro Glu Thr Val Ser
    1160                1165                1170

Ala Ala Thr Gln Thr Ile Lys Asn Val Cys Glu Gln Gly Thr Ser
    1175                1180                1185

Thr Val Asp Gln Asn Phe Gly Lys Gln Asp Ala Thr Val Gln Thr
    1190                1195                1200

Glu Arg Gly Ser Gly Glu Lys Pro Val Ser Ala Pro Gly Asp Asp
    1205                1210                1215

Thr Glu Ser Leu His Ser Gln Gly Glu Glu Glu Phe Asp Met Pro
    1220                1225                1230

Gln Pro Pro His Gly His Val Leu His Arg His Met Arg Thr Ile
    1235                1240                1245

Arg Glu Val Arg Thr Leu Val Thr Arg Val Ile Thr Asp Val Tyr
    1250                1255                1260

Tyr Val Asp Gly Thr Glu Val Glu Arg Lys Val Thr Glu Glu Thr
    1265                1270                1275

Glu Glu Pro Ile Val Glu Cys Gln Glu Cys Glu Thr Glu Val Ser
```

-continued

```
            1280                1285                1290

Pro Ser Gln Thr Gly Gly Ser Ser Gly Asp Leu Gly Asp Ile Ser
        1295                1300                1305

Ser Phe Ser Ser Lys Ala Ser Ser Leu His Arg Thr Ser Ser Gly
        1310                1315                1320

Thr Ser Leu Ser Ala Met His Ser Ser Gly Ser Ser Gly Lys Gly
        1325                1330                1335

Ala Gly Pro Leu Arg Gly Lys Thr Ser Gly Thr Glu Pro Ala Asp
        1340                1345                1350

Phe Ala Leu Pro Ser Ser Arg Gly Gly Pro Gly Lys Leu Ser Pro
        1355                1360                1365

Arg Lys Gly Val Ser Gln Thr Gly Thr Pro Val Cys Glu Glu Asp
        1370                1375                1380

Gly Asp Ala Gly Leu Gly Ile Arg Gln Gly Gly Lys Ala Pro Val
        1385                1390                1395

Thr Pro Arg Gly Arg Gly Arg Arg Gly Arg Pro Pro Ser Arg Thr
        1400                1405                1410

Thr Gly Thr Arg Glu Thr Ala Val Pro Gly Pro Leu Gly Ile Glu
        1415                1420                1425

Asp Ile Ser Pro Asn Leu Ser Pro Asp Asp Lys Ser Phe Ser Arg
        1430                1435                1440

Val Val Pro Arg Val Pro Asp Ser Thr Arg Arg Thr Asp Val Gly
        1445                1450                1455

Ala Gly Ala Leu Arg Arg Ser Asp Ser Pro Glu Ile Pro Phe Gln
        1460                1465                1470

Ala Ala Ala Gly Pro Ser Asp Gly Leu Asp Ala Ser Ser Pro Gly
        1475                1480                1485

Asn Ser Phe Val Gly Leu Arg Val Val Ala Lys Trp Ser Ser Asn
        1490                1495                1500

Gly Tyr Phe Tyr Ser Gly Lys Ile Thr Arg Asp Val Gly Ala Gly
        1505                1510                1515

Lys Tyr Lys Leu Leu Phe Asp Gly Tyr Glu Cys Asp Val Leu
        1520                1525                1530

Gly Lys Asp Ile Leu Leu Cys Asp Pro Ile Pro Leu Asp Thr Glu
        1535                1540                1545

Val Thr Ala Leu Ser Glu Asp Glu Tyr Phe Ser Ala Gly Val Val
        1550                1555                1560

Lys Gly His Arg Lys Glu Ser Gly Glu Leu Tyr Tyr Ser Ile Glu
        1565                1570                1575

Lys Glu Gly Gln Arg Lys Trp Tyr Lys Arg Met Ala Val Ile Leu
        1580                1585                1590

Ser Leu Glu Gln Gly Asn Arg Leu Arg Glu Gln Tyr Gly Leu Gly
        1595                1600                1605

Pro Tyr Glu Ala Val Thr Pro Leu Thr Lys Ala Ala Asp Ile Ser
        1610                1615                1620

Leu Asp Asn Leu Val Glu Gly Lys Arg Lys Arg Arg Ser Asn Val
        1625                1630                1635

Ser Ser Pro Ala Thr Pro Thr Ala Ser Ser Ser Ser Thr Thr
        1640                1645                1650

Pro Thr Arg Lys Ile Thr Glu Ser Pro Arg Ala Ser Met Gly Val
        1655                1660                1665

Leu Ser Gly Lys Arg Lys Leu Ile Thr Ser Glu Glu Glu Arg Ser
        1670                1675                1680
```

```
Pro Ala Lys Arg Gly Arg Lys Ser Ala Thr Val Lys Pro Val Gly
    1685            1690                1695

Ala Gly Glu Phe Val Ser Pro Cys Glu Ser Gly Asp Asn Thr Gly
    1700            1705                1710

Glu Pro Ser Ala Leu Glu Glu Gln Arg Gly Pro Leu Pro Leu Asn
    1715            1720                1725

Lys Thr Leu Phe Leu Gly Tyr Ala Phe Leu Leu Thr Met Ala Thr
    1730            1735                1740

Thr Ser Asp Lys Leu Ala Ser Arg Ser Lys Leu Pro Asp Gly Pro
    1745            1750                1755

Thr Gly Ser Ser Glu Glu Glu Glu Phe Leu Glu Ile Pro Pro
    1760            1765                1770

Phe Asn Lys Gln Tyr Thr Glu Ser Gln Leu Arg Ala Gly Ala Gly
    1775            1780                1785

Tyr Ile Leu Glu Asp Phe Asn Glu Ala Gln Cys Asn Thr Ala Tyr
    1790            1795                1800

Gln Cys Leu Leu Ile Ala Asp Gln His Cys Arg Thr Arg Lys Tyr
    1805            1810                1815

Phe Leu Cys Leu Ala Ser Gly Ile Pro Cys Val Ser His Val Trp
    1820            1825                1830

Val His Asp Ser Cys His Ala Asn Gln Leu Gln Asn Tyr Arg Asn
    1835            1840                1845

Tyr Leu Leu Pro Ala Gly Tyr Ser Leu Glu Glu Gln Arg Ile Leu
    1850            1855                1860

Asp Trp Gln Pro Arg Glu Asn Pro Phe Gln Asn Leu Lys Val Leu
    1865            1870                1875

Leu Val Ser Asp Gln Gln Gln Asn Phe Leu Glu Leu Trp Ser Glu
    1880            1885                1890

Ile Leu Met Thr Gly Gly Ala Ala Ser Val Lys Gln His His Ser
    1895            1900                1905

Ser Ala His Asn Lys Asp Ile Ala Leu Gly Val Phe Asp Val Val
    1910            1915                1920

Val Thr Asp Pro Ser Cys Pro Ala Ser Val Leu Lys Cys Ala Glu
    1925            1930                1935

Ala Leu Gln Leu Pro Val Val Ser Gln Glu Trp Val Ile Gln Cys
    1940            1945                1950

Leu Ile Val Gly Glu Arg Ile Gly Phe Lys Gln His Pro Lys Tyr
    1955            1960                1965

Lys His Asp Tyr Val Ser His
    1970            1975

<210> SEQ ID NO 12
<211> LENGTH: 1972
<212> TYPE: PRT
<213> ORGANISM: Homo sapiens

<400> SEQUENCE: 12

Met Asp Pro Thr Gly Ser Gln Leu Asp Ser Asp Phe Ser Gln Asp
1               5                   10                  15

Thr Pro Cys Leu Ile Ile Glu Asp Ser Gln Pro Glu Ser Gln Val Leu
                20                  25                  30

Glu Asp Asp Ser Gly Ser His Phe Ser Met Leu Ser Arg His Leu Pro
            35                  40                  45

Asn Leu Gln Thr His Lys Glu Asn Pro Val Leu Asp Val Val Ser Asn
```

-continued

```
                50                  55                  60
Pro Glu Gln Thr Ala Gly Glu Arg Gly Asp Gly Asn Ser Gly Phe
 65                  70                  75                  80

Asn Glu His Leu Lys Glu Asn Lys Val Ala Asp Pro Val Asp Ser Ser
                 85                  90                  95

Asn Leu Asp Thr Cys Gly Ser Ile Ser Gln Val Ile Glu Gln Leu Pro
            100                 105                 110

Gln Pro Asn Arg Thr Ser Ser Val Leu Gly Met Ser Val Glu Ser Ala
            115                 120                 125

Pro Ala Val Glu Glu Glu Lys Gly Glu Glu Leu Glu Gln Lys Glu Lys
            130                 135                 140

Glu Lys Glu Glu Asp Thr Ser Gly Asn Thr Thr His Ser Leu Gly Ala
145                 150                 155                 160

Glu Asp Thr Ala Ser Ser Gln Leu Gly Phe Gly Val Leu Glu Leu Ser
                165                 170                 175

Gln Ser Gln Asp Val Glu Glu Asn Thr Val Pro Tyr Glu Val Asp Lys
            180                 185                 190

Glu Gln Leu Gln Ser Val Thr Thr Asn Ser Gly Tyr Thr Arg Leu Ser
            195                 200                 205

Asp Val Asp Ala Asn Thr Ala Ile Lys His Glu Glu Gln Ser Asn Glu
            210                 215                 220

Asp Ile Pro Ile Ala Glu Gln Ser Ser Lys Asp Ile Pro Val Thr Ala
225                 230                 235                 240

Gln Pro Ser Lys Asp Val His Val Val Lys Glu Gln Asn Pro Pro Pro
                245                 250                 255

Ala Arg Ser Glu Asp Met Pro Phe Ser Pro Lys Ala Ser Val Ala Ala
            260                 265                 270

Met Glu Ala Lys Glu Gln Leu Ser Ala Gln Glu Leu Met Glu Ser Gly
            275                 280                 285

Leu Gln Ile Gln Lys Ser Pro Glu Pro Glu Val Leu Ser Thr Gln Glu
            290                 295                 300

Asp Leu Phe Asp Gln Ser Asn Lys Thr Val Ser Ser Asp Gly Cys Ser
305                 310                 315                 320

Thr Pro Ser Arg Glu Glu Gly Gly Cys Ser Leu Ala Ser Thr Pro Ala
                325                 330                 335

Thr Thr Leu His Leu Leu Gln Leu Ser Gly Gln Arg Ser Leu Val Gln
            340                 345                 350

Asp Ser Leu Ser Thr Asn Ser Ser Asp Leu Val Ala Pro Ser Pro Asp
            355                 360                 365

Ala Phe Arg Ser Thr Pro Phe Ile Val Pro Ser Ser Pro Thr Glu Gln
            370                 375                 380

Glu Gly Arg Gln Asp Lys Pro Met Asp Thr Ser Val Leu Ser Glu Glu
385                 390                 395                 400

Gly Gly Glu Pro Phe Gln Lys Lys Leu Gln Ser Gly Glu Pro Val Glu
                405                 410                 415

Leu Glu Asn Pro Pro Leu Leu Pro Glu Ser Thr Val Ser Pro Gln Ala
            420                 425                 430

Ser Thr Pro Ile Ser Gln Ser Thr Pro Val Phe Pro Pro Gly Ser Leu
            435                 440                 445

Pro Ile Pro Ser Gln Pro Gln Phe Ser His Asp Ile Phe Ile Pro Ser
            450                 455                 460

Pro Ser Leu Glu Glu Gln Ser Asn Asp Gly Lys Lys Asp Gly Asp Met
465                 470                 475                 480
```

```
His Ser Ser Ser Leu Thr Val Glu Cys Ser Lys Thr Ser Glu Ile Glu
                485                 490                 495

Pro Lys Asn Ser Pro Glu Asp Leu Gly Leu Ser Leu Thr Gly Asp Ser
            500                 505                 510

Cys Lys Leu Met Leu Ser Thr Ser Glu Tyr Ser Gln Ser Pro Lys Met
            515                 520                 525

Glu Ser Leu Ser Ser His Arg Ile Asp Glu Asp Gly Glu Asn Thr Gln
            530                 535                 540

Ile Glu Asp Thr Glu Pro Met Ser Pro Val Leu Asn Ser Lys Phe Val
545                 550                 555                 560

Pro Ala Glu Asn Asp Ser Ile Leu Met Asn Pro Ala Gln Asp Gly Glu
            565                 570                 575

Val Gln Leu Ser Gln Asn Asp Asp Lys Thr Lys Gly Asp Asp Thr Asp
            580                 585                 590

Thr Arg Asp Asp Ile Ser Ile Leu Ala Thr Gly Cys Lys Gly Arg Glu
            595                 600                 605

Glu Thr Val Ala Glu Asp Val Cys Ile Asp Leu Thr Cys Asp Ser Gly
            610                 615                 620

Ser Gln Ala Val Pro Ser Pro Ala Thr Arg Ser Glu Ala Leu Ser Ser
625                 630                 635                 640

Val Leu Asp Gln Glu Glu Ala Met Glu Ile Lys Glu His His Pro Glu
            645                 650                 655

Glu Gly Ser Ser Gly Ser Glu Val Glu Glu Ile Pro Glu Thr Pro Cys
            660                 665                 670

Glu Ser Gln Gly Glu Glu Leu Lys Glu Glu Asn Met Glu Ser Val Pro
            675                 680                 685

Leu His Leu Ser Leu Thr Glu Thr Gln Ser Gln Gly Leu Cys Leu Gln
            690                 695                 700

Lys Glu Met Pro Lys Lys Glu Cys Ser Glu Ala Met Glu Val Glu Thr
705                 710                 715                 720

Ser Val Ile Ser Ile Asp Ser Pro Gln Lys Leu Ala Ile Leu Asp Gln
            725                 730                 735

Glu Leu Glu His Lys Glu Gln Glu Ala Trp Glu Glu Ala Thr Ser Glu
            740                 745                 750

Asp Ser Ser Val Val Ile Val Asp Val Lys Glu Pro Ser Pro Arg Val
            755                 760                 765

Asp Val Ser Cys Glu Pro Leu Glu Gly Val Glu Lys Cys Ser Asp Ser
            770                 775                 780

Gln Ser Trp Glu Asp Ile Ala Pro Glu Ile Glu Pro Cys Ala Glu Asn
785                 790                 795                 800

Arg Leu Asp Thr Lys Glu Glu Lys Ser Val Glu Tyr Glu Gly Asp Leu
            805                 810                 815

Lys Ser Gly Thr Ala Glu Thr Glu Pro Val Glu Gln Asp Ser Ser Gln
            820                 825                 830

Pro Ser Leu Pro Leu Val Arg Ala Asp Asp Pro Leu Arg Leu Asp Gln
            835                 840                 845

Glu Leu Gln Gln Pro Gln Thr Gln Glu Lys Thr Ser Asn Ser Leu Thr
850                 855                 860

Glu Asp Ser Lys Met Ala Asn Ala Lys Gln Leu Ser Ser Asp Ala Glu
865                 870                 875                 880

Ala Gln Lys Leu Gly Lys Pro Ser Ala His Ala Ser Gln Ser Phe Cys
            885                 890                 895
```

```
Glu Ser Ser Ser Glu Thr Pro Phe His Phe Thr Leu Pro Lys Glu Gly
                900                 905                 910

Asp Ile Ile Pro Pro Leu Thr Gly Ala Thr Pro Leu Ile Gly His
        915                 920                 925

Leu Lys Leu Glu Pro Lys Arg His Ser Thr Pro Ile Gly Ile Ser Asn
    930                 935                 940

Tyr Pro Glu Ser Thr Ile Ala Thr Ser Asp Val Met Ser Glu Ser Met
945                 950                 955                 960

Val Glu Thr His Asp Pro Ile Leu Gly Ser Gly Lys Gly Asp Ser Gly
                965                 970                 975

Ala Ala Pro Asp Val Asp Asp Lys Leu Cys Leu Arg Met Lys Leu Val
            980                 985                 990

Ser Pro Glu Thr Glu Ala Ser Glu  Glu Ser Leu Gln Phe  Asn Leu Glu
            995                 1000                1005

Lys Pro  Ala Thr Gly Glu Arg  Lys Asn Gly Ser Thr  Ala Val Ala
    1010                1015                1020

Glu Ser  Val Ala Ser Pro Gln  Lys Thr Met Ser Val  Leu Ser Cys
    1025                1030                1035

Ile Cys  Glu Ala Arg Gln Glu  Asn Glu Ala Arg Ser  Glu Asp Pro
    1040                1045                1050

Pro Thr  Thr Pro Ile Arg Gly  Asn Leu Leu His Phe  Pro Ser Ser
    1055                1060                1065

Gln Gly  Glu Glu Lys Glu  Lys Leu Glu Gly Asp  His Thr Ile
    1070                1075                1080

Arg Gln  Ser Gln Gln Pro Met  Lys Pro Ile Ser Pro  Val Lys Asp
    1085                1090                1095

Pro Val  Ser Pro Ala Ser Gln  Lys Met Val Ile Gln  Gly Pro Ser
    1100                1105                1110

Ser Pro  Gln Gly Glu Ala Met  Val Thr Asp Val Leu  Glu Asp Gln
    1115                1120                1125

Lys Glu  Gly Arg Ser Thr Asn  Lys Glu Asn Pro Ser  Lys Ala Leu
    1130                1135                1140

Ile Glu  Arg Pro Ser Gln Asn  Asn Ile Gly Ile Gln  Thr Met Glu
    1145                1150                1155

Cys Ser  Leu Arg Val Pro Glu  Thr Val Ser Ala Ala  Thr Gln Thr
    1160                1165                1170

Ile Lys  Asn Val Cys Glu Gln  Gly Thr Ser Thr Val  Asp Gln Asn
    1175                1180                1185

Phe Gly  Lys Gln Asp Ala Thr  Val Gln Thr Glu Arg  Gly Ser Gly
    1190                1195                1200

Glu Lys  Pro Val Ser Ala Pro  Gly Asp Asp Thr Glu  Ser Leu His
    1205                1210                1215

Ser Gln  Gly Glu Glu Glu Phe  Asp Met Pro Gln Pro  Pro His Gly
    1220                1225                1230

His Val  Leu His Arg His Met  Arg Thr Ile Arg Glu  Val Arg Thr
    1235                1240                1245

Leu Val  Thr Arg Val Ile Thr  Asp Val Tyr Tyr Val  Asp Gly Thr
    1250                1255                1260

Glu Val  Glu Arg Lys Val Thr  Glu Glu Thr Glu Glu  Pro Ile Val
    1265                1270                1275

Glu Cys  Gln Glu Cys Glu Thr  Glu Val Ser Pro Ser  Gln Thr Gly
    1280                1285                1290

Gly Ser  Ser Gly Asp Leu Gly  Asp Ile Ser Ser Phe  Ser Ser Lys
```

```
                1295                1300                1305
Ala  Ser  Ser  Leu  His  Arg  Thr  Ser  Ser  Gly  Thr  Ser  Leu  Ser  Ala
         1310                1315                1320
Met  His  Ser  Ser  Gly  Ser  Ser  Gly  Lys  Gly  Ala  Gly  Pro  Leu  Arg
    1325                1330                1335
Gly  Lys  Thr  Ser  Gly  Thr  Glu  Pro  Ala  Asp  Phe  Ala  Leu  Pro  Ser
         1340                1345                1350
Ser  Arg  Gly  Gly  Pro  Gly  Lys  Leu  Ser  Pro  Arg  Lys  Gly  Val  Ser
         1355                1360                1365
Gln  Thr  Gly  Thr  Pro  Val  Cys  Glu  Glu  Asp  Gly  Asp  Ala  Gly  Leu
         1370                1375                1380
Gly  Ile  Arg  Gln  Gly  Gly  Lys  Ala  Pro  Val  Thr  Pro  Arg  Gly  Arg
         1385                1390                1395
Gly  Arg  Arg  Gly  Arg  Pro  Pro  Ser  Arg  Thr  Thr  Gly  Thr  Arg  Glu
         1400                1405                1410
Thr  Ala  Val  Pro  Gly  Pro  Leu  Gly  Ile  Glu  Asp  Ile  Ser  Pro  Asn
         1415                1420                1425
Leu  Ser  Pro  Asp  Asp  Lys  Ser  Phe  Ser  Arg  Val  Val  Pro  Arg  Val
         1430                1435                1440
Pro  Asp  Ser  Thr  Arg  Arg  Thr  Asp  Val  Gly  Ala  Gly  Ala  Leu  Arg
         1445                1450                1455
Arg  Ser  Asp  Ser  Pro  Glu  Ile  Pro  Phe  Gln  Ala  Ala  Ala  Gly  Pro
         1460                1465                1470
Ser  Asp  Gly  Leu  Asp  Ala  Ser  Ser  Pro  Gly  Asn  Ser  Phe  Val  Gly
         1475                1480                1485
Leu  Arg  Val  Val  Ala  Lys  Trp  Ser  Ser  Asn  Gly  Tyr  Phe  Tyr  Ser
         1490                1495                1500
Gly  Lys  Ile  Thr  Arg  Asp  Val  Gly  Ala  Gly  Lys  Tyr  Lys  Leu  Leu
         1505                1510                1515
Phe  Asp  Asp  Gly  Tyr  Glu  Cys  Asp  Val  Leu  Gly  Lys  Asp  Ile  Leu
         1520                1525                1530
Leu  Cys  Asp  Pro  Ile  Pro  Leu  Asp  Thr  Glu  Val  Thr  Ala  Leu  Ser
         1535                1540                1545
Glu  Asp  Glu  Tyr  Phe  Ser  Ala  Gly  Val  Val  Lys  Gly  His  Arg  Lys
         1550                1555                1560
Glu  Ser  Gly  Glu  Leu  Tyr  Tyr  Ser  Ile  Glu  Lys  Glu  Gly  Gln  Arg
         1565                1570                1575
Lys  Trp  Tyr  Lys  Arg  Met  Ala  Val  Ile  Leu  Ser  Leu  Glu  Gln  Gly
         1580                1585                1590
Asn  Arg  Leu  Arg  Glu  Gln  Tyr  Gly  Leu  Gly  Pro  Tyr  Glu  Ala  Val
         1595                1600                1605
Thr  Pro  Leu  Thr  Lys  Ala  Ala  Asp  Ile  Ser  Leu  Asp  Asn  Leu  Val
         1610                1615                1620
Glu  Gly  Lys  Arg  Lys  Arg  Arg  Ser  Asn  Val  Ser  Ser  Pro  Ala  Thr
         1625                1630                1635
Pro  Thr  Ala  Ser  Ser  Ser  Ser  Thr  Thr  Pro  Thr  Arg  Lys  Ile
         1640                1645                1650
Thr  Glu  Ser  Pro  Arg  Ala  Ser  Met  Gly  Val  Leu  Ser  Gly  Lys  Arg
         1655                1660                1665
Lys  Leu  Ile  Thr  Ser  Glu  Glu  Arg  Ser  Pro  Ala  Lys  Arg  Gly
         1670                1675                1680
Arg  Lys  Ser  Ala  Thr  Val  Lys  Pro  Gly  Ala  Val  Gly  Ala  Gly  Glu
         1685                1690                1695
```

```
Phe Val Ser Pro Cys Glu Ser Gly Asp Asn Thr Gly Glu Pro Ser
    1700                1705                1710

Ala Leu Glu Glu Gln Arg Gly Pro Leu Pro Leu Asn Lys Thr Leu
    1715                1720                1725

Phe Leu Gly Tyr Ala Phe Leu Leu Thr Met Ala Thr Thr Ser Asp
    1730                1735                1740

Lys Leu Ala Ser Arg Ser Lys Leu Pro Asp Gly Pro Thr Gly Ser
    1745                1750                1755

Ser Glu Glu Glu Glu Glu Phe Leu Glu Ile Pro Pro Phe Asn Lys
    1760                1765                1770

Gln Tyr Thr Glu Ser Gln Leu Arg Ala Gly Ala Gly Tyr Ile Leu
    1775                1780                1785

Glu Asp Phe Asn Glu Ala Gln Cys Asn Thr Ala Tyr Gln Cys Leu
    1790                1795                1800

Leu Ile Ala Asp Gln His Cys Arg Thr Arg Lys Tyr Phe Leu Cys
    1805                1810                1815

Leu Ala Ser Gly Ile Pro Cys Val Ser His Val Trp Val His Asp
    1820                1825                1830

Ser Cys His Ala Asn Gln Leu Gln Asn Tyr Arg Asn Tyr Leu Leu
    1835                1840                1845

Pro Ala Gly Tyr Ser Leu Glu Glu Gln Arg Ile Leu Asp Trp Gln
    1850                1855                1860

Pro Arg Glu Asn Pro Phe Gln Asn Leu Lys Val Leu Leu Val Ser
    1865                1870                1875

Asp Gln Gln Gln Asn Phe Leu Glu Leu Trp Ser Glu Ile Leu Met
    1880                1885                1890

Thr Gly Gly Ala Ala Ser Val Lys Gln His His Ser Ser Ala His
    1895                1900                1905

Asn Lys Asp Ile Ala Leu Gly Val Phe Asp Val Val Thr Asp
    1910                1915                1920

Pro Ser Cys Pro Ala Ser Val Leu Lys Cys Ala Glu Ala Leu Gln
    1925                1930                1935

Leu Pro Val Val Ser Gln Glu Trp Val Ile Gln Cys Leu Ile Val
    1940                1945                1950

Gly Glu Arg Ile Gly Phe Lys Gln His Pro Lys Tyr Lys His Asp
    1955                1960                1965

Tyr Val Ser His
    1970

<210> SEQ ID NO 13
<211> LENGTH: 559
<212> TYPE: PRT
<213> ORGANISM: Homo sapiens

<400> SEQUENCE: 13

Met Phe Pro Phe Gly Pro His Ser Pro Gly Gly Asp Gly Ser Ala Gly
1               5                   10                  15

Ala Gly Ala Glu Glu Pro Thr Pro His Glu Gly Gln Ala Ala Ala Thr
            20                  25                  30

Gly Pro Pro Ser Pro Leu His Pro Gly Ala Asp Ala Thr His Pro Pro
        35                  40                  45

Pro Pro Ala Arg Ser Pro Arg Arg Pro Gly Ala Pro Ser Leu Ser Pro
    50                  55                  60

Ala Pro Arg Ser Gly Glu Leu Gly Leu Pro Gly Ala Pro Glu Ser Ser
```

```
                65                  70                  75                  80
Thr Ala Ser Ala Pro Gly Glu Pro Ser Pro Pro Ser Pro Pro Cys Arg
                    85                  90                  95

Arg Pro Gly Pro Asp Cys Arg Ala Lys Ser Arg Gly Arg His Gly Leu
                    100                 105                 110

Gly Ala Gly Leu Gly Gly Pro Gly Ala Arg Leu Phe Gly Trp Leu Lys
                    115                 120                 125

Glu Arg Ser Leu Gly Arg Gly Leu Phe Val Asp Pro Ala Arg Asp Asn
                    130                 135                 140

Phe Arg Thr Met Thr Ser Leu Tyr Gly Ser Ile His Pro Ala Asp Ser
145                 150                 155                 160

Val Tyr Leu Ser Thr Arg Thr His Gly Ala Val Phe Asn Leu Glu Tyr
                    165                 170                 175

Ser Pro Asp Gly Ser Val Leu Thr Val Ala Cys Glu Gln Thr Glu Val
                    180                 185                 190

Leu Leu Phe Asp Pro Ile Ser Ser Lys His Ile Lys Thr Leu Ser Glu
                    195                 200                 205

Ala His Glu Asp Cys Val Asn Asn Ile Arg Phe Leu Asp Asn Arg Leu
                    210                 215                 220

Phe Ala Thr Cys Ser Asp Asp Thr Thr Ile Ala Leu Trp Asp Leu Arg
225                 230                 235                 240

Lys Leu Asn Thr Lys Val Cys Thr Leu His Gly His Thr Ser Trp Val
                    245                 250                 255

Lys Asn Ile Glu Tyr Asp Thr Asn Thr Arg Leu Leu Val Thr Ser Gly
                    260                 265                 270

Phe Asp Gly Asn Val Ile Ile Trp Asp Thr Asn Arg Tyr Thr Glu Asp
                    275                 280                 285

Gly Cys Pro His Lys Lys Phe Phe His Thr Arg Phe Leu Met Arg Met
                    290                 295                 300

Arg Leu Thr Pro Asp Cys Ser Lys Met Leu Ile Ser Thr Ser Ser Gly
305                 310                 315                 320

Tyr Leu Leu Ile Leu His Asp Leu Asp Leu Thr Lys Ser Leu Glu Val
                    325                 330                 335

Gly Ser Tyr Pro Ile Leu Arg Ala Arg Arg Thr Thr Ser Ser Ser Asp
                    340                 345                 350

Leu Thr Thr Ser Ser Ser Ser Ser Gly Pro Arg Val Ser Gly Ser Pro
                    355                 360                 365

Cys His His Ser Asp Ser Asn Ser Ser Glu Lys His Met Ser Arg Ala
                    370                 375                 380

Ser Gln Arg Glu Gly Val Ser Pro Arg Asn Ser Leu Glu Val Val Thr
385                 390                 395                 400

Pro Glu Val Leu Gly Glu Ser Asp His Gly Asn Cys Ile Thr Ser Leu
                    405                 410                 415

Gln Leu His Pro Lys Gly Trp Ala Thr Leu Leu Arg Cys Ser Ser Asn
                    420                 425                 430

Ser Asp Asp Glu Glu Cys Thr Cys Val Tyr Glu Phe Gln Glu Gly Ala
                    435                 440                 445

Pro Val Arg Pro Val Ser Pro Arg Cys Ser Leu Arg Leu Thr His Tyr
                    450                 455                 460

Ile Glu Glu Ala Asn Val Gly Arg Gly Tyr Ile Lys Glu Leu Cys Phe
465                 470                 475                 480

Ser Pro Asp Gly Arg Met Ile Ser Ser Pro His Gly Tyr Gly Ile Arg
                    485                 490                 495
```

-continued

```
Leu Leu Gly Phe Asp Lys Gln Cys Ser Glu Leu Val Asp Cys Leu Pro
                500                 505                 510
Lys Glu Ala Ser Pro Leu Arg Val Ile Arg Ser Leu Tyr Ser His Asn
            515                 520                 525
Asp Val Val Leu Thr Thr Lys Phe Ser Pro Thr His Cys Gln Ile Ala
530                 535                 540
Ser Gly Cys Leu Ser Gly Arg Val Ser Leu Tyr Gln Pro Lys Phe
545                 550                 555

<210> SEQ ID NO 14
<211> LENGTH: 386
<212> TYPE: PRT
<213> ORGANISM: Homo sapiens

<400> SEQUENCE: 14

Met Leu Ser Arg Ser His Arg Ser Val Leu Thr Val Ala Cys Glu Gln
1               5                   10                  15
Thr Glu Val Leu Leu Phe Asp Pro Ile Ser Ser Lys His Ile Lys Thr
                20                  25                  30
Leu Ser Glu Ala His Glu Asp Cys Val Asn Asn Ile Arg Phe Leu Asp
            35                  40                  45
Asn Arg Leu Phe Ala Thr Cys Ser Asp Asp Thr Thr Ile Ala Leu Trp
50                  55                  60
Asp Leu Arg Lys Leu Asn Thr Lys Val Cys Thr Leu His Gly His Thr
65                  70                  75                  80
Ser Trp Val Lys Asn Ile Glu Tyr Asp Thr Asn Thr Arg Leu Leu Val
                85                  90                  95
Thr Ser Gly Phe Asp Gly Asn Val Ile Ile Trp Asp Thr Asn Arg Tyr
                100                 105                 110
Thr Glu Asp Gly Cys Pro His Lys Lys Phe Phe His Thr Arg Phe Leu
            115                 120                 125
Met Arg Met Arg Leu Thr Pro Asp Cys Ser Lys Met Leu Ile Ser Thr
130                 135                 140
Ser Ser Gly Tyr Leu Leu Ile Leu His Asp Leu Asp Leu Thr Lys Ser
145                 150                 155                 160
Leu Glu Val Gly Ser Tyr Pro Ile Leu Arg Ala Arg Arg Thr Thr Ser
                165                 170                 175
Ser Ser Asp Leu Thr Thr Ser Ser Ser Ser Gly Pro Arg Val Ser
            180                 185                 190
Gly Ser Pro Cys His His Ser Asp Ser Asn Ser Ser Glu Lys His Met
            195                 200                 205
Ser Arg Ala Ser Gln Arg Glu Gly Val Ser Pro Arg Asn Ser Leu Glu
210                 215                 220
Val Val Thr Pro Glu Val Leu Gly Glu Ser Asp His Gly Asn Cys Ile
225                 230                 235                 240
Thr Ser Leu Gln Leu His Pro Lys Gly Trp Ala Thr Leu Leu Arg Cys
                245                 250                 255
Ser Ser Asn Ser Asp Asp Glu Cys Thr Cys Val Tyr Glu Phe Gln
                260                 265                 270
Glu Gly Ala Pro Val Arg Pro Val Ser Pro Arg Cys Ser Leu Arg Leu
            275                 280                 285
Thr His Tyr Ile Glu Glu Ala Asn Val Gly Arg Gly Tyr Ile Lys Glu
290                 295                 300
Leu Cys Phe Ser Pro Asp Gly Arg Met Ile Ser Ser Pro His Gly Tyr
```

```
                 305                 310                 315                 320
Gly Ile Arg Leu Leu Gly Phe Asp Lys Gln Cys Ser Glu Leu Val Asp
                325                 330                 335
Cys Leu Pro Lys Glu Ala Ser Pro Leu Arg Val Ile Arg Ser Leu Tyr
                340                 345                 350
Ser His Asn Asp Val Val Leu Thr Thr Lys Phe Ser Pro Thr His Cys
                355                 360                 365
Gln Ile Ala Ser Gly Cys Leu Ser Gly Arg Val Ser Leu Tyr Gln Pro
                370                 375                 380
Lys Phe
385

<210> SEQ ID NO 15
<211> LENGTH: 108
<212> TYPE: PRT
<213> ORGANISM: Homo sapiens

<400> SEQUENCE: 15

Met Ala Ala Ala Met Asp Val Asp Thr Pro Ser Gly Thr Asn Ser Gly
1               5                   10                  15
Ala Gly Lys Lys Arg Phe Glu Val Lys Lys Trp Asn Ala Val Ala Leu
                20                  25                  30
Trp Ala Trp Asp Ile Val Val Asp Asn Cys Ala Ile Cys Arg Asn His
            35                  40                  45
Ile Met Asp Leu Cys Ile Glu Cys Gln Ala Asn Gln Ala Ser Ala Thr
        50                  55                  60
Ser Glu Glu Cys Thr Val Ala Trp Gly Val Cys Asn His Ala Phe His
65                  70                  75                  80
Phe His Cys Ile Ser Arg Trp Leu Lys Thr Arg Gln Val Cys Pro Leu
                85                  90                  95
Asp Asn Arg Glu Trp Glu Phe Gln Lys Tyr Gly His
            100                 105

<210> SEQ ID NO 16
<211> LENGTH: 768
<212> TYPE: PRT
<213> ORGANISM: Homo sapiens

<400> SEQUENCE: 16

Met Ser Asn Leu Ser Lys Gly Thr Gly Ser Arg Lys Asp Thr Lys Met
1               5                   10                  15
Arg Ile Arg Ala Phe Pro Met Thr Met Asp Glu Lys Tyr Val Asn Ser
                20                  25                  30
Ile Trp Asp Leu Leu Lys Asn Ala Ile Gln Glu Ile Gln Arg Lys Asn
            35                  40                  45
Asn Ser Gly Leu Ser Phe Glu Glu Leu Tyr Arg Asn Ala Tyr Thr Met
        50                  55                  60
Val Leu His Lys His Gly Glu Lys Leu Tyr Thr Gly Leu Arg Glu Val
65                  70                  75                  80
Val Thr Glu His Leu Ile Asn Lys Val Arg Glu Asp Val Leu Asn Ser
                85                  90                  95
Leu Asn Asn Asn Phe Leu Gln Thr Leu Asn Gln Ala Trp Asn Asp His
            100                 105                 110
Gln Thr Ala Met Val Met Ile Arg Asp Ile Leu Met Tyr Met Asp Arg
        115                 120                 125
Val Tyr Val Gln Gln Asn Asn Val Glu Asn Val Tyr Asn Leu Gly Leu
```

```
            130                 135                 140
Ile Ile Phe Arg Asp Gln Val Arg Tyr Gly Cys Ile Arg Asp His
145                 150                 155                 160

Leu Arg Gln Thr Leu Leu Asp Met Ile Ala Arg Glu Arg Lys Gly Glu
                165                 170                 175

Val Val Asp Arg Gly Ala Ile Arg Asn Ala Cys Gln Met Leu Met Ile
            180                 185                 190

Leu Gly Leu Glu Gly Arg Ser Val Tyr Glu Glu Asp Phe Glu Ala Pro
        195                 200                 205

Phe Leu Glu Met Ser Ala Glu Phe Phe Gln Met Glu Ser Gln Lys Phe
        210                 215                 220

Leu Ala Glu Asn Ser Ala Ser Val Tyr Ile Lys Lys Val Glu Ala Arg
225                 230                 235                 240

Ile Asn Glu Glu Ile Glu Arg Val Met His Cys Leu Asp Lys Ser Thr
                245                 250                 255

Glu Glu Pro Ile Val Lys Val Val Glu Arg Glu Leu Ile Ser Lys His
            260                 265                 270

Met Lys Thr Ile Val Glu Met Glu Asn Ser Gly Leu Val His Met Leu
        275                 280                 285

Lys Asn Gly Lys Thr Glu Asp Leu Gly Cys Met Tyr Lys Leu Phe Ser
290                 295                 300

Arg Val Pro Asn Gly Leu Lys Thr Met Cys Glu Cys Met Ser Ser Tyr
305                 310                 315                 320

Leu Arg Glu Gln Gly Lys Ala Leu Val Ser Glu Glu Gly Glu Gly Lys
                325                 330                 335

Asn Pro Val Asp Tyr Ile Gln Gly Leu Leu Asp Leu Lys Ser Arg Phe
            340                 345                 350

Asp Arg Phe Leu Leu Glu Ser Phe Asn Asn Asp Arg Leu Phe Lys Gln
        355                 360                 365

Thr Ile Ala Gly Asp Phe Glu Tyr Phe Leu Asn Leu Asn Ser Arg Ser
        370                 375                 380

Pro Glu Tyr Leu Ser Leu Phe Ile Asp Asp Lys Leu Lys Lys Gly Val
385                 390                 395                 400

Lys Gly Leu Thr Glu Gln Glu Val Glu Thr Ile Leu Asp Lys Ala Met
                405                 410                 415

Val Leu Phe Arg Phe Met Gln Glu Lys Asp Val Phe Glu Arg Tyr Tyr
            420                 425                 430

Lys Gln His Leu Ala Arg Arg Leu Leu Thr Asn Lys Ser Val Ser Asp
        435                 440                 445

Asp Ser Glu Lys Asn Met Ile Ser Lys Leu Lys Thr Glu Cys Gly Cys
450                 455                 460

Gln Phe Thr Ser Lys Leu Glu Gly Met Phe Arg Asp Met Ser Ile Ser
465                 470                 475                 480

Asn Thr Thr Met Asp Glu Phe Arg Gln His Leu Gln Ala Thr Gly Val
                485                 490                 495

Ser Leu Gly Gly Val Asp Leu Thr Val Arg Val Leu Thr Thr Gly Tyr
            500                 505                 510

Trp Pro Thr Gln Ser Ala Thr Pro Lys Cys Asn Ile Pro Pro Ala Pro
        515                 520                 525

Arg His Ala Phe Glu Ile Phe Arg Arg Phe Tyr Leu Ala Lys His Ser
        530                 535                 540

Gly Arg Gln Leu Thr Leu Gln His His Met Gly Ser Ala Asp Leu Asn
545                 550                 555                 560
```

-continued

Ala Thr Phe Tyr Gly Pro Val Lys Lys Glu Asp Gly Ser Glu Val Gly
            565                 570                 575

Val Gly Gly Ala Gln Val Thr Gly Ser Asn Thr Arg Lys His Ile Leu
        580                 585                 590

Gln Val Ser Thr Phe Gln Met Thr Ile Leu Met Leu Phe Asn Asn Arg
    595                 600                 605

Glu Lys Tyr Thr Phe Glu Glu Ile Gln Gln Glu Thr Asp Ile Pro Glu
610                 615                 620

Arg Glu Leu Val Arg Ala Leu Gln Ser Leu Ala Cys Gly Lys Pro Thr
625                 630                 635                 640

Gln Arg Val Leu Thr Lys Glu Pro Lys Ser Lys Glu Ile Glu Asn Gly
                645                 650                 655

His Ile Phe Thr Val Asn Asp Gln Phe Thr Ser Lys Leu His Arg Val
            660                 665                 670

Lys Ile Gln Thr Val Ala Ala Lys Gln Gly Glu Ser Asp Pro Glu Arg
        675                 680                 685

Lys Glu Thr Arg Gln Lys Val Asp Asp Arg Lys His Glu Ile Glu
    690                 695                 700

Ala Ala Ile Val Arg Ile Met Lys Ser Arg Lys Lys Met Gln His Asn
705                 710                 715                 720

Val Leu Val Ala Glu Val Thr Gln Gln Leu Lys Ala Arg Phe Leu Pro
                725                 730                 735

Ser Pro Val Val Ile Lys Lys Arg Ile Glu Gly Leu Ile Glu Arg Glu
            740                 745                 750

Tyr Leu Ala Arg Thr Pro Glu Asp Arg Lys Val Tyr Thr Tyr Val Ala
        755                 760                 765

<210> SEQ ID NO 17
<211> LENGTH: 897
<212> TYPE: PRT
<213> ORGANISM: Homo sapiens

<400> SEQUENCE: 17

Met Asn Ile Ser Gly Ser Ser Cys Gly Ser Pro Asn Ser Ala Asp Thr
1               5                   10                  15

Ser Ser Asp Phe Lys Asp Leu Trp Thr Lys Leu Lys Glu Cys His Asp
            20                  25                  30

Arg Glu Val Gln Gly Leu Gln Val Lys Val Thr Lys Leu Lys Gln Glu
        35                  40                  45

Arg Ile Leu Asp Ala Gln Arg Leu Glu Glu Phe Phe Thr Lys Asn Gln
    50                  55                  60

Gln Leu Arg Glu Gln Gln Lys Val Leu His Glu Thr Ile Lys Val Leu
65                  70                  75                  80

Glu Asp Arg Leu Arg Ala Gly Leu Cys Asp Arg Cys Ala Val Thr Glu
                85                  90                  95

Glu His Met Arg Lys Lys Gln Gln Glu Phe Glu Asn Ile Arg Gln Gln
            100                 105                 110

Asn Leu Lys Leu Ile Thr Glu Leu Met Asn Glu Arg Asn Thr Leu Gln
        115                 120                 125

Glu Glu Asn Lys Lys Leu Ser Glu Gln Leu Gln Lys Ile Glu Asn
    130                 135                 140

Asp Gln Gln His Gln Ala Ala Glu Leu Glu Cys Glu Glu Asp Val Ile
145                 150                 155                 160

Pro Asp Ser Pro Ile Thr Ala Phe Ser Phe Ser Gly Val Asn Arg Leu

-continued

```
                165                 170                 175
Arg Arg Lys Glu Asn Pro His Val Arg Tyr Ile Glu Gln Thr His Thr
                180                 185                 190
Lys Leu Glu His Ser Val Cys Ala Asn Glu Met Arg Lys Val Ser Lys
                195                 200                 205
Ser Ser Thr His Pro Gln His Asn Pro Asn Glu Asn Glu Ile Leu Val
                210                 215                 220
Ala Asp Thr Tyr Asp Gln Ser Gln Ser Pro Met Ala Lys Ala His Gly
225                 230                 235                 240
Thr Ser Ser Tyr Thr Pro Asp Lys Ser Ser Phe Asn Leu Ala Thr Val
                245                 250                 255
Val Ala Glu Thr Leu Gly Leu Gly Val Gln Glu Ser Glu Thr Gln
                260                 265                 270
Gly Pro Met Ser Pro Leu Gly Asp Glu Leu Tyr His Cys Leu Glu Gly
                275                 280                 285
Asn His Lys Lys Gln Pro Phe Glu Ser Thr Arg Asn Thr Glu Asp
                290                 295                 300
Ser Leu Arg Phe Ser Asp Ser Thr Ser Lys Thr Pro Gln Glu Glu
305                 310                 315                 320
Leu Pro Thr Arg Val Ser Ser Pro Val Phe Gly Ala Thr Ser Ser Ile
                325                 330                 335
Lys Ser Gly Leu Asp Leu Asn Thr Ser Leu Ser Pro Ser Leu Leu Gln
                340                 345                 350
Pro Gly Lys Lys Lys His Leu Lys Thr Leu Pro Phe Ser Asn Thr Cys
                355                 360                 365
Ile Ser Arg Leu Glu Lys Thr Arg Ser Lys Ser Glu Asp Ser Ala Leu
                370                 375                 380
Phe Thr His His Ser Leu Gly Ser Glu Val Asn Lys Ile Ile Ile Gln
385                 390                 395                 400
Ser Ser Asn Lys Gln Ile Leu Ile Asn Lys Asn Ile Ser Glu Ser Leu
                405                 410                 415
Gly Glu Gln Asn Arg Thr Glu Tyr Gly Lys Asp Ser Asn Thr Asp Lys
                420                 425                 430
His Leu Glu Pro Leu Lys Ser Leu Gly Gly Arg Thr Ser Lys Arg Lys
                435                 440                 445
Lys Thr Glu Glu Glu Ser Glu His Glu Val Ser Cys Pro Gln Ala Ser
                450                 455                 460
Phe Asp Lys Glu Asn Ala Phe Pro Phe Pro Met Asp Asn Gln Phe Ser
465                 470                 475                 480
Met Asn Gly Asp Cys Val Met Asp Lys Pro Leu Asp Leu Ser Asp Arg
                485                 490                 495
Phe Ser Ala Ile Gln Arg Gln Glu Lys Ser Gln Gly Ser Glu Thr Ser
                500                 505                 510
Lys Asn Lys Phe Arg Gln Val Thr Leu Tyr Glu Ala Leu Lys Thr Ile
                515                 520                 525
Pro Lys Gly Phe Ser Ser Ser Arg Lys Ala Ser Asp Gly Asn Cys Thr
                530                 535                 540
Leu Pro Lys Asp Ser Pro Gly Glu Pro Cys Ser Gln Glu Cys Ile Ile
545                 550                 555                 560
Leu Gln Pro Leu Asn Lys Cys Ser Pro Asp Asn Lys Pro Ser Leu Gln
                565                 570                 575
Ile Lys Glu Glu Asn Ala Val Phe Lys Ile Pro Leu Arg Pro Arg Glu
                580                 585                 590
```

```
Ser Leu Glu Thr Glu Asn Val Leu Asp Asp Ile Lys Ser Ala Gly Ser
        595                 600                 605

His Glu Pro Ile Lys Ile Gln Thr Arg Ser Asp His Gly Gly Cys Glu
        610                 615                 620

Leu Ala Ser Val Leu Gln Leu Asn Pro Cys Arg Thr Gly Lys Ile Lys
625                 630                 635                 640

Ser Leu Gln Asn Asn Gln Asp Val Ser Phe Glu Asn Ile Gln Trp Ser
                645                 650                 655

Ile Asp Pro Gly Ala Asp Leu Ser Gln Tyr Lys Met Asp Val Thr Val
                660                 665                 670

Ile Asp Thr Lys Asp Gly Ser Gln Ser Lys Leu Gly Gly Glu Thr Val
        675                 680                 685

Asp Met Asp Cys Thr Leu Val Ser Glu Thr Val Leu Leu Lys Met Lys
        690                 695                 700

Lys Gln Glu Gln Lys Gly Glu Lys Ser Ser Asn Glu Glu Arg Lys Met
705                 710                 715                 720

Asn Asp Ser Leu Glu Asp Met Phe Asp Arg Thr Thr His Glu Glu Tyr
                725                 730                 735

Glu Ser Cys Leu Ala Asp Ser Phe Ser Gln Ala Ala Asp Glu Glu Glu
                740                 745                 750

Glu Leu Ser Thr Ala Thr Lys Lys Leu His Thr His Gly Asp Lys Gln
                755                 760                 765

Asp Lys Val Lys Gln Lys Ala Phe Val Glu Pro Tyr Phe Lys Gly Asp
        770                 775                 780

Glu Arg Glu Thr Ser Leu Gln Asn Phe Pro His Ile Glu Val Val Arg
785                 790                 795                 800

Lys Lys Glu Glu Arg Arg Lys Leu Leu Gly His Thr Cys Lys Glu Cys
                805                 810                 815

Glu Ile Tyr Tyr Ala Asp Met Pro Ala Glu Glu Arg Glu Lys Lys Leu
                820                 825                 830

Ala Ser Cys Ser Arg His Arg Phe Arg Tyr Ile Pro Pro Asn Thr Pro
        835                 840                 845

Glu Asn Phe Trp Glu Val Gly Phe Pro Ser Thr Gln Thr Cys Met Glu
        850                 855                 860

Arg Gly Tyr Ile Lys Glu Asp Leu Asp Pro Cys Pro Arg Pro Lys Arg
865                 870                 875                 880

Arg Gln Pro Tyr Asn Ala Ile Phe Ser Pro Lys Gly Lys Glu Gln Lys
                885                 890                 895

Thr
```